(12) United States Patent
Cox et al.

(10) Patent No.: US 10,653,728 B2
(45) Date of Patent: May 19, 2020

(54) PROBIOTIC COMPOSITIONS FOR IMPROVING METABOLISM AND IMMUNITY

(71) Applicant: New York University, New York, NY (US)

(72) Inventors: Laura M. Cox, Brookline, MA (US); Martin J. Blaser, New York, NY (US)

(73) Assignee: NEW YORK UNIVERSITY, New York, NY (US)

(*) Notice: Subject to any disclaimer, the term of this patent is extended or adjusted under 35 U.S.C. 154(b) by 0 days.

(21) Appl. No.: 15/786,483

(22) Filed: Oct. 17, 2017

(65) Prior Publication Data

US 2018/0125900 A1 May 10, 2018

Related U.S. Application Data

(60) Provisional application No. 62/409,164, filed on Oct. 17, 2016, provisional application No. 62/489,696, filed on Apr. 25, 2017.

(51) Int. Cl.
*A61K 45/06* (2006.01)
*A61K 35/741* (2015.01)

(52) U.S. Cl.
CPC ............ *A61K 35/741* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,348,452 | B1 | 2/2002 | Brown et al. |
| 6,942,857 | B2 | 9/2005 | Song et al. |
| 9,386,793 | B2 * | 7/2016 | Blaser .................. A61K 35/741 |
| 9,603,876 | B2 * | 3/2017 | Blaser .................. A61K 35/741 |
| 2001/0001711 | A1 | 5/2001 | Olshenitsky et al. |
| 2002/0048567 | A1 | 4/2002 | Olshenitsky et al. |
| 2002/0048568 | A1 | 4/2002 | Olshenitsky et al. |
| 2002/0048569 | A1 | 4/2002 | Olshenitsky et al. |
| 2002/0048570 | A1 | 4/2002 | Olshenitsky et al. |
| 2002/0051772 | A1 | 5/2002 | Olshenitsky et al. |
| 2002/0051773 | A1 | 5/2002 | Olshenitsky et al. |
| 2002/0051774 | A1 | 5/2002 | Olshenitsky et al. |
| 2002/0051775 | A1 | 5/2002 | Olshenitsky et al. |
| 2002/0051776 | A1 | 5/2002 | Olshenitsky et al. |
| 2002/0054866 | A1 | 5/2002 | Olshenitsky et al. |
| 2002/0054867 | A1 | 5/2002 | Olshenitsky et al. |
| 2002/0054868 | A1 | 5/2002 | Olshenitsky et al. |
| 2002/0071835 | A1 | 6/2002 | Olshenitsky et al. |
| 2004/0028689 | A1 | 2/2004 | Borody |
| 2004/0052909 | A1 | 3/2004 | Contento et al. |
| 2004/0265291 | A1 | 12/2004 | Drake et al. |
| 2005/0037089 | A1 | 2/2005 | Jobbins |
| 2005/0112112 | A1 | 5/2005 | Park et al. |
| 2005/0176001 | A1 | 8/2005 | Nakano et al. |
| 2006/0088514 | A1 | 4/2006 | O'Mahony et al. |
| 2007/0009577 | A1 | 1/2007 | Mankovitz |
| 2008/0131401 | A1 | 6/2008 | Brown et al. |
| 2009/0035329 | A1 | 2/2009 | Blaser et al. |
| 2009/0324736 | A1 | 12/2009 | Johnson et al. |
| 2010/0074872 | A1 | 3/2010 | Blaser et al. |
| 2010/0172874 | A1 | 7/2010 | Turnbaugh et al. |
| 2010/0216212 | A1 | 8/2010 | Morita et al. |
| 2011/0280840 | A1 | 11/2011 | Blaser et al. |
| 2012/0058094 | A1 | 3/2012 | Blaser et al. |
| 2012/0171193 | A1 | 7/2012 | Blaser et al. |
| 2012/0276149 | A1 | 11/2012 | Littman et al. |
| 2015/0037285 | A1 | 2/2015 | Blaser et al. |
| 2016/0120915 | A1 | 5/2016 | Blaser et al. |
| 2017/0151290 | A1 | 6/2017 | Blaser et al. |

FOREIGN PATENT DOCUMENTS

| | | |
|---|---|---|
| EP | 1886680 A1 | 2/2008 |
| WO | 1997/034591 A1 | 9/1997 |
| WO | 2000/075284 A1 | 12/2000 |

(Continued)

OTHER PUBLICATIONS

Karvonen, M. Ph.D. et al., "Incidence of Childhood Type 1 Diabetes Worldwide", Diabetes Care (2000), vol. 23:10, pp. 1516-1526.

Kwok, L. et al., "The impact of oral consumption of Lactobacillus plantarum P-8 on faecal bacteria revealed by pyrosequencing", Beneficial Microbes (2015), vol. 6:4, pp. 405-413.

Ley et al., Microbial ecology: Human gut microbes associated with obesity, Nature (2006), vol. 444, pp. 1022-1023.

Ley et al., "Obesity alters gut microbial ecology", Proc. Natl. Acad. Sci. USA (2005), vol. 102, pp. 11070-11075.

(Continued)

*Primary Examiner* — Padmavathi Baskar
(74) *Attorney, Agent, or Firm* — Troutman Sanders LLP

(57) ABSTRACT

The application relates to methods based on modulating mammalian intestinal microbiota and related probiotic and prebiotic compositions. Specifically, the application relates to the use of novel bacterial genera *Ileibacterium* and *Dubosiella*, including their species *I. valens* (*I. valens*) and *Dubosiella newyorkensis* (*D. newy*), respectively, and closely related OTUs within the family Erysipelotrichaceae that resemble either *Ileibacterium* spp. or *Dubosiella* spp. with 90% 16S rRNA sequence identity, for modulating weight and intestinal inflammation and immunity (including modulating intestinal immune gene expression such as, e.g., modulating expression of RORγT, IL-17A, IL-17F, RegIIIγ, Relmβ, and Defβ), as well as for treatment and diagnosis of (i) obesity and related conditions such as metabolic syndrome and diabetes mellitus; (ii) allergic and autoimmune diseases, and (iii) gastrointestinal disorders (such as, e.g., inflammatory bowel disease (IBD), ulcerative colitis, Crohn's disease, and celiac disease).

6 Claims, 22 Drawing Sheets
(15 of 22 Drawing Sheet(s) Filed in Color)
Specification includes a Sequence Listing.

(56) References Cited

FOREIGN PATENT DOCUMENTS

| WO | 2001/015715 A1 | 3/2001 |
|---|---|---|
| WO | 2009/018447 A2 | 2/2009 |
| WO | 2012/024638 A2 | 2/2012 |
| WO | 2013/037068 A1 | 3/2013 |
| WO | 2013/050792 A1 | 4/2013 |

OTHER PUBLICATIONS

Li et al., Symbiotic gut microbes modulate human metabolic phenotypes, Proc. Natl. Acad. Sci. USA (2008), vol. 105, pp. 2117-2122.
Mahowald et al., "Characterizing a model human gut microbiota composed of members of its two dominant bacterial phyla", Proc Natl Acad Sci. (2009), vol. 106:14, pp. 5859-5864.
Marietta, E.V. et al., "Low Incidence of Spontaneous Type 1 Diabetes in Non-Obese Diabetic Mice Raised on Gluten-Free Diets is Associated iwht Changes in the Intestinal Microbiome", PLOS One (2013), vol. 8:11, e78687, pp. 1-9.
Marques et al. "Expression and functional importance of innate immune receptors by intestinal epithelial cells," Cell Mol Life Sci (2011), vol. 68, Iss. 22, pp. 3661-3673.
Morris et al, "Helicobacter pylori infection link to lower rates of asthma," Lancet Infectious Diseases (2007), Elsevier Ltd., US, vol. 7, No. 6, p. 379.
Mueller, et al., Prenatal exposure to antibiotics, cesarean section and risk of childhood obesity, Int JObes (Lond) 39(4): 665-670. (2015).
Murri, M. et al., "Gut Microbiota in Children with Type 1 Diabetes differs from that in healthy children: a case-control study", BMC Medicine (2013), vol. 11:46, pp. 1-12.
O'Hara et al., "The gut flora as a forgotten organ" European Molecular Biology Organization, 2006, vol. 7:7, pp. 688-693.
O'Toole, P. W. et al., "Probiotic Bacteria Influence the Composition and Function of the Intestinal Microbiota", Interdisciplinary Perspectives on Infectious Diseases (2008), pp. 1-9, doi:10.1155/2008/175285.
Parks, et al., Genetic Control of Obesity and Gut Microbiota Composition in Response to High-Fat, High-Sucrose Diet in Mice, Cell Metabolism 17: 141-152. (2013).
Paulino et al., Molecular Analysis of Fungal Microbiota in Samples from Healthy Human Skin and Psoriatic Lesions, J Clin Microbiol (2006), vol. 44, pp. 2933-2941.
Penders, J. et al., "Factors Influencing the Composition of the Intestinal Microbiota in Early Infancy", Pediatrics (2006), vol. 118:2, pp. 511-521.
Pieper, R. et al., "Effect of a single oral administration of Lactobacillus plantarum DSMZ 8862/8866 before and at the time point of weaning on intestinal microbial communities in piglets", International Journal of Food Microbiology (2009), vol. 130, pp. 227-232, doi:10.1016/j.ijfoodmicro.2009.01.026.
Pietrella, D. et al., Th17 Cells and IL-17 in Protective Immunity to Vaginal Candidiasis, PLoS One (2011), vol. 6:7, e22770, pp. 1-11.
Qin et al., "A human gut microbial gene catalogue established by metagenomic sequencing", Nature (2010), vol. 464, pp. 59-67.
Rauch, Marcus et al., "Probiotic manipulation of the gastrointestinal microbiota". Gut Microbes (2010), vol. 1(5), pp. 335-338, doi:10.4161/gmic.1.5_13169.
Ravussin, Y. et al., "Responses of Gut Microbiota to Diet Composition and Weight Loss in Lean and Obese Mice", Obesity (2012), vol. 20, No. 4, pp. 738-747.
Ray, Adding weight to the microbiota's role in obesity-exposure to antibiotic early in life can lead to increased adiposity, Nature Reviews/Gastroenterology & Hepatology (2012), vol. 9.
Sczesnak, A. et al., "The genome of Th17 cell-inducing segmented filamentous bacteria reveals extensive auxotrophy and adaptations to the intestinal environment", Cell Host Microbe (2011), vol. 10:3, pp. 260-272. Doi:10.1016/j.chom.2011.08.005.

Sifferlin, Alexandra, "Antibiotics in Early Life Can Lead to Weight Gain in Mice, Study Shows", Time Magazine, 2014. http://time.com/3111864/antibiotics-weight-gain-mice/. <http://time.com/3111864/antibiotics-weight-gain-mice/>.
Simpson, J.L. et al., "Clarithromycin Targets Neutrophilic Airway Inflammation in Refractory Asthma", Am. J. Respir. Crit. Care Med. (2008), vol. 177, pp. 148-155.
Slack, E. et al., "A flexible continuum between adaptive and innate immunity in maintaining host-microbiota mutualism", Science (2009), vol. 325, pp. 617-620. Doi:10.1126/science.1172747.
Sonnerburg et al., "Genomic and metabolic studies of the impact of probiotics on a model gut symbiont and host", PLoS Biol (2006), vol. 4(12):e413, pp. 2213-2226.
Stockert, K., "Physiological intestinal flora in children of 6 to 12 years of age with bronchial asthma," Deutsche Zeitschrift Fur Akupunktur (2001), DE, vol. 44, No. 4, pp. 268-271 (English abstract provided).
Teddy Study Group, "The Environmental Determinants of Diabetes in the Young (Teddy) Study", Ann. N.Y. Acad. Sci., Immunology of Diabetes V: (2008), vol. 1150, pp. 1-13; doi: 01.1196/annal.1447.062.
Trasande et al., "Infant antibiotic exposure and early-life body mass", International Journal of Obesity (2012), advance online publication, pp. 1-8; doi: 10.1038/ijo.2012.132.
Trasande et al., "Infant antibiotic exposures and early-life body mass", Int J Obes (2013), (Lond), vol. 37(1), pp. 16-23.
Tuohy et al., "Using probiotics and prebiotics to improve gut health," Therapeutic Focus (2003), vol. 8(15), pp. 692-700.
Turnbaugh et al., "An obesity-associated gut microbiome with increased capacity for energy harvest", Nature (2006), vol. 444, pp. 1027-1031.
Turta, Olli et al., "Antibiotics, obesity and the link to microbes—what are we doing to our children?" BMC Medicine (2016), vol. 14:57, 6 pages.
Uibo, R. et al., "Celiac disease in patients with type 1 diabetes: a condition with distinct changes in intestinal immunity?", Cellular & Molecular Immunology (2011), vol. 8, pp. 150-156.
Van Nood et al., "Duodenal Infusion of Donor Feces for Recurrent Clostridium difficile", New England Journal of Medicine (2013), vol. 368:5, pp. 407-415.
Vijay-Kumar, M. et al., "Metabolic Syndrome and Altered Gut Microbiota in Mice Lacking Toll-Like Receptor 5", Science (2010) vol. 328(5975), pp. 228-231. Doi:10.1126/science.1179721.
Wade, "Unculturable bacteria—the uncharacterized organisms that cause orl infections", Journal of The Royal Society of Medicine (2002), vol. 95, pp. 81-83.
Wen et al., "Innate immunity and intestinal microbiota in the development of Type 1 diabetes", Nature (2008), vol. 455, pp. 1109-1113.
Wikoff et al., "Metabolomics analysis reveals large effects of gut microflora on mammalian blood metabolites", Proc Natl Acad Sci (2009), vol. 106:10, pp. 3698-3703.
Wilson et al., "Applications of molecular ecology in the characterization of uncultured microorganisms associated with human disease", Reviews in Medical Microbiology (1997), vol. 8, pp. 91-101.
Woese, CR et al. "Phylogenetic analysis of the mycoplasmas", Proceedings of the National Academy of Sciences, vol. 77, pp. 494-498 (1980).
Written Opinion of International Searching Authority issued in International Appl. No. PCT/US2009/058351, dated May 10, 2010.
Written Opinion of International Searching Authority issued in International Appl. No. PCT/US2011/048501, dated Mar. 13, 2012.
Yatsunenko, T. et al., "Human gut microbiome viewed across age and geography", Nature (2012), vol. 486:222, 8 pages. Doi:10.1038/nature11053.
Zhang, X. et al., "Structural Changes of Gut Microbiota during Berberine-Mediated Prevention of Obesity and Insulin Resistance in High-Fat Diet-Fed Rats", Plos One (2012), vol. 7, Issue 8, p. e42529.
Zoetendal et al., "High-throughput diversity and functionality analysis of the gastrointestinal tract microbiota", (Gut 2008), vol. 57, pp. 1605-1615.

(56) References Cited

OTHER PUBLICATIONS

Brandt et al. "An overview of fecal microbiota transplantation: techniques, indications, and outcomes", Gastrointestinal Endoscopy (2013), vol. 78:2, pp. 240-249.
Cox, L. et al., "Pathways in Microbe-Induced Obesity", Cell Metab. (2013), vol. 17(6), pp. 883-894.
International Preliminary Report on Patentability issued in International Appl. No. PCT/US2009/058351, dated Mar. 29, 2011.
Uhlar, C.M. et al., "Serum Amyloid A, the Major Vertebrate Acute-Phase Reactant" Eur. J. Biochem. (1999) vol. 265, pp. 501-523.
Ajslev, et al., "Childhood overweight after establishment of the gut microbiota: the role of delivery mode, pre-pregnancy weight and early administration of antibiotics", International Journal of Obesity (2011), vol. 35, pp. 522-529.
Andersson et al., "Comparative analysis of human gut microbiota by barcoded pyrosequencing", PLoS One (2008), vol. 3, Issue 7, e2836, pp. 1-8.
Armougom et al., Monitoring Bacterial Communicaty of Human Gut Microbiota Reveals and Increase in Lactobacillus in Obese Patients and Methanogens in Anorexic Patients, PLoS ONE (2009), vol. 4(9): e7125.
Armougom et al., "Use of pyrosequencing and DNA barcodes to monitor variations in Firmicutes and Bacteroidetes commmunities in the gut microbiota of obese humans", BMC Genomics (2008), vol. 9, p. 576.
Azad, et al., "Infant antibiotic exposure and the development of childhood overweight and central adiposity", International Journal of Obesity (2014), vol. 38, pp. 1290-1298.
Bailey, et al., "Association of Antibiotics in Infancy With Early Childhood Obesity", JAMA Pediatr. (2014), vol. 168 (11), pp. 1063-1069.
Bartosch et al., "Characterization of bacterial communities in feces from healthy elderly volunteers and hospitalized elderly patients by using real-time PCR and effects of antibiotic treatment on the fecal microbiota", Applied and Enviromental Microbiology (2004), vol. 70, No. 6, p. 3575-3581.
Bjursell et al. "Functional Genomic and Metabolic Studies of the Adaptations of a Prominent Adult Human Gut Symbiont, Bacteroides thetaiotaomicron, to the Suckling Period", Journal of Biological Chemistry (2006), vol. 281, pp. 36269-36279.
Blaser et al., "Does Helicobacter pylori protect against asthma and allergy?", Gut (2008), vol. 57, pp. 561-567.
Brugman, S. et al., "Antibiotic treatment partially protects against type 1 diabetes in the Bio-Breeding diabetes-prone rat. Is the gut flora involved in the development of type 1 diabetes?", Diabetologia (2006), vol. 49, pp. 2105-2108.
Cao, X.Y. et al., "Tilmicosin and tylosin have anti-inflammatory properties via modulation of COX-2 and iNOS gene expression and production of cytokines in LPS-induced macrophages and monocytes", Intl. Journal of Antimicrobial Agents (2006), vol. 27, pp. 431-438.
Cardwell, C.R., Ph.D. et al., "Breast-Feeding and Childhood-Onset Type 1 Diabetes: A pooled analysis of individual participant date from 43 observational studies", Diabetes Care (2012), vol. 35, pp. 2215-2225.
Chen et al., "Helicobacter pylori Colonization is Inversely Associated with Childhood Asthma", Journal of Infectious Diseases (2008), vol. 198, pp. 553-560.
Cho et al., "Antibiotics in early life alter the murine colonic microbiome and adiposity", Nature (2012), vol. 488, pp. 621-626.
Conti, H.R. et al., "Th17 cells and IL-17 receptor signaling are essential for mucosal host defense against oral candidiasis", J. Exp. Med. (2009), vol. 206:2, pp. 299-311. (www.jem.org/cgi/doi/10.1084/jem.20081463).
Costello et al., "Bacterial Community Variation in Human Body Habitats Across Space and Time" Science (2009), vol. 326, pp. 1694-1697.
Cox et al., "Altering the Intestinal Microbiota during a Critical Developmental Window Has Lasting Metabolic Consequences", Cell (2014), vol. 158, pp. 705-721.
Cox, L. et al., "Antibiotics in early life and obesity", Nat. Rev. Endocrinol. (2015), vol. 11, pp. 182-190.
Cox, M. J. et al., "Lactobacillus casei Abundance is Associated with Profound Shifts in the Infant Gut Microbiome", PLoS ONE (2010), vol. 5:1, e8745, doi:10.1371/journal.pone.0008745.
De Goffau, Marcus C. et al., "Fecal Micorbiota Composition Differs Between Children with ?-Cell Autoimmunity and Those Without", Diabetes (2013), vol. 62, pp. 1238-1244.
DiBaise, J.K. et al., Gut Microbiota and Its Possible Relationship With ObesityMayo Clinic Proceedings, Apr. 2008, vol. 83(4), pp. 460-469.
Duncan et al., "Cultivable bacterial diversity from the human colon", Letters in Applied Microbiology (2007), vol. 44, pp. 343-350.
Eckburg et al., "Diversity of the Human Intestinal Microbial Flora", Science (2005), vol. 308, pp. 1635-1638.
Extended European Search Report, dated Feb. 28, 2013, which issued during the prosecution of European Patent Application No. 09816896.6.
Fak, Frida et al. "Lactobacillus reuteri Prevents Diet-Induces Obesity, but not Athersclerosis, in a Strain Dependent Fashion in Apoe2/2 Mice", Plos One (2012), vol. 7, e46837.
Flint, "Antibiotics and adiposity", Nature (2012), vol. 488, pp. 601-602.
Flint, H.J., "The significance of prokaryote diversity in the human gastrointestinal tract, in SGM symposium 66: Prokaryotic Diversity: mechanisms and significance", Logan et al., eds., Cambridge University Press (2012), pp. 65-90.
Fuller, "Probiotics in man and animals", J. Applied Bacteriol. (1989), vol. 66, pp. 365-378.
Gao et al., "Molecular analysis of human forearm superficial skin bacterial biota", Proc. Natl. Acad. Sci. USA (2007), vol. 104, pp. 2927-2932.
Gao et al., "Substantial Alterations of the Cutaneous Bacterial Biota in Psoriatic Lesions", PLoS One (2008), vol. 3, pp. e2719-2728.
Gori et al. "Specific prebiotics modulate gut microbiota and immune activation in HAART adults: results of the 'COPA' pilot randomized trial," Nature (2011), vol. 4, No. 5, pp. 554-563.
Greenblum et al., "Metagenomic systems biology of the human gut microbiome reveals topological shifts associated with obesity and inflammatory bowel disease", Proc Natl Acad Sci (2012), vol. 109:2, pp. 594-599.
Grice et al., "Topographical and Temporal Diversity of the Human Skin Microbiome", Science (2009), vol. 324, pp. 1190-1192.
Grölund, M-M. et al., "Fecal Microflora in Healthy Infants Born by Different Methods of Delivery: Permanent Changes in Intestinal Flora After Cesarean Delivery", J. Ped. Gastroenterology & Nutrition (1999), Issue: vol. 28:1, pp. 19-21.
Grzeskowiak, L. et al., "Distinct Gut Microbiota in Southeastern African and Northern European Infants", J. Ped. Gastroenterol. and Nutrition (2012), vol. 54, pp. 812-816.
Hara, N. et al., "Prevention of Virus-Induced Type 1 Diabetes with Antibiotic Therapy", J Immunol (2012), vol. 189, pp. 3805-3814.
Hemarajata, P. et al., "Effects of probiotics on gut microbiota: mechanism of intestinal immunomodulation and neuromodulation", Therapeutic Advances in Gastroenterology (2013), vol. 6:1, pp. 39-51, doi:10.1177/1756283X12459294.
Hernandez-Santos, N. et al., "Th17 cells confer long-term adaptive immunity to oral mucosal Candida albicans infections", www.nature.com/mi <http://www.nature.com/mi> (2012), vol. 6:5, pp. 900-910.
Hill, et al., The International Scientific Association for Probiotics and Prebiotics consensus statement on the scope and appropriate use of the term probiotic, Nat. Rev. Gastroenterol. Hepatol. (2014), vol. 11, pp. 506-514.
Holzapfel et al., "Overview of gut flora and probiotics," Int J Food Microbiol (1998), vol. 41, pp. 85-101.
Hong Hye Jin et al., "Differential suppression of allergen-induced airway inflammation in murine model of asthma by actic acid bacteria," FASEB Journal, vol. 22, 2008, abstract.
Hopkins et al., "Age and disease related changes in intetestinal bacterial populations assessed by cell culture, 16S—RNA abundance, and community cellular fatty acid profiles", Gut (2001), Feb.; vol. 48(2), pp. 198-205.

(56) References Cited

OTHER PUBLICATIONS

Ildgruben, A.K. et al., "Influence of Hormonal Contraceptives on the Immune Cells and Thickness of Human Vaginal Epithelium", Obstet Gynecol (2003), vol. 102, pp. 571-582.

International Search Report and Written Opinion dated Jan. 9, 2015 during prosecution of International Patent Application No. PCT/US2014/041770.

International Search Report issued in International Appl. No. PCT/US2009/058351, dated May 10, 2010.

International Search Report issued in International Appl. No. PCT/US2011/048501, dated Mar. 13, 2012.

Ivanov, I.I. et al., "Induction of Intestinal Th17 cells by segmented filamentous bacteria", Cell (2009), vol. 139:3, pp. 485-498. Doi:10.1016/j.cell.2009.09.033.

Jess, T., "Microbiota, Antibiotics, and Obesity", N. Engl. J. Med. (2014), vol. 371(26), pp. 2526-2528.

Jonsson, H. et al., "Segmented filamentous bacteria in human ileostomy samples after high-fiber intake", FEMS Microbiol Lett (2013), vol. 342, pp. 24-29.

Kanoh, S. et al., "Mechanisms of Action and Clinical Application of Macrolides as Immunomodulatory medications", Clinical Microbiology Reviews (2010); pp. 590-615. Doi: 10.1128/CMR.00078-09.

Bergman, E.N., "Energy Contributions of Volatile Fatty Acids from the Gastrointestinal Tract in Various Species" Physiological Reviews (1990) vol. 70, No. 2, pp. 567-590.

International Preliminary Report on Patentability issued in International Appl. No. PCT/US2011/048501, dated Feb. 26, 2013.

International Preliminary Report on Patentability dated Dec. 15, 2015 during prosecution of International Patent Application No. PCT/US2014/041770, 17 pages total.

Kaakoush, N.O., "Insights into the Role of Erysipelotrichaceae in the Human Host" Frontiers in Cellular and Infection Microbiology (2015) vol. 5, pp. 1-4.

Kondo, S. et al., "Bifidobacterium Breve B-3 Exerts Metabolic Syndrome-Suppressing Effects in the Liver of Diet-Induced Obese Mice: A DNA Mircroarray Analysis" Beneficial Microbes (2013) vol. 4, No. 3, pp. 247-251.

Pryde, S.E. et al. "The Microbiology of Butyrate Formation in the Human Colon" FEMS Microbiology Letters (2002) vol. 217, No. 2, pp. 133-139.

Remely, M. et al., "Effects of Short Chain Fatty Acid Producing Bacteria on Epigenetic Regulation of FFAR3 in Type 2 Diabetes and Obesity" Gene (2014) vol. 537, pp. 85-92.

Wolever, T.M.S. et al., "Propionate Inhibits Incorporation of Colonic [1,2-13C]acetate into Plasma Lipids i n Humans1-3" American Journal of Clinical Nutrition (1995) vol. 61, pp. 1241-1247.

Wolfe, A.J., "The Acetate Switch" Microbiology and Molecular Biology Reviews (2005) vol. 69, No. 1, pp. 12-50.

Wong, J.M.W., et al., "Colonic Health: Fermentation and Short Chain Fatty Acids" J. Clin. Gastroenterol. (2006) vol. 40, pages 235-243.

Wright, R.S., et al., "Propionate Inhibits Hepatocyte Lipid Synthesis" Proc. Soc. Exp. Biol. Med. (1990) vol. 195, pp. 26-29.

Xiao, L., et al., "High-Fat Feeding Rather than Obesity Drives Taxonomical and Functional Changes in the Gut Microbiota in Mice" Microbiome (2017) vol. 5, No. 43, pp. 1-12.

Calcinaro, F., et al., "Oral Probiotic Administration Includes Interleukin-10 Production and Prevents Spontaneous Anutoimmune Diabetes in the Non-Obese Diabetic Mouse" Diabetologia (2005) vol. 48, pp. 1565-1575.

Eckhardt, E. RM, et al., "Intestinal Epithelial Serum Amyloid A Modulates Bacterial Growth In Vitro and Pro-Inflammatory Responses in Mouse Experimental Colits" BMC Gastroenterology (2010) vol. 10, No. 133, 9 pages total.

Ohland, C.L., et al., "Probiotic Bacteria and Intestinal Epithelial Barrier Function" American Journal of Gastrointestinal Liver Physiology (2010) vol. 298, pp. G807-G819.

Zhang, X-S. et al., "Antibiotic-Induced Acceleration of Type 1 Diabetes Alters Maturation of Innate Intestinal Immunity" eLife (2018) vol. 7, e37816, pp. 1-37.

* cited by examiner

Antimicrobial peptides

FIG. 2A
FIG. 2B
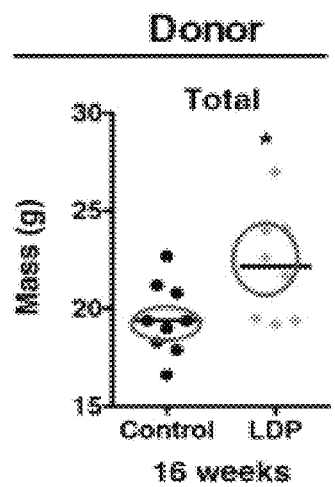
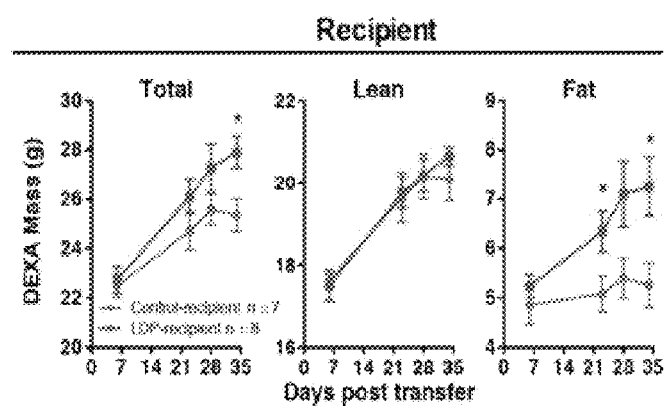
FIG. 2C
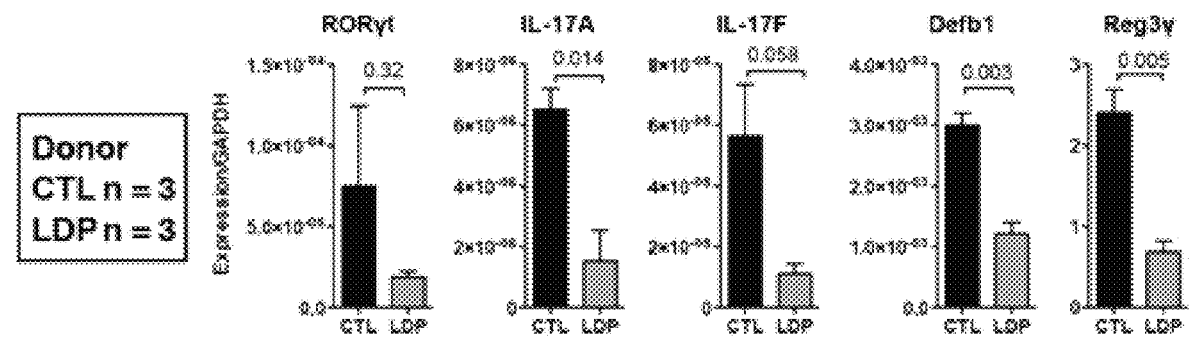
FIG. 2D
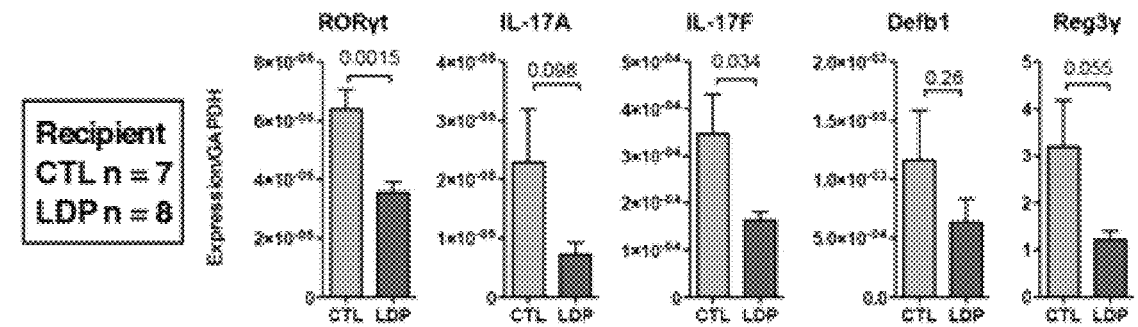

FIG. 3A
FIG. 3B
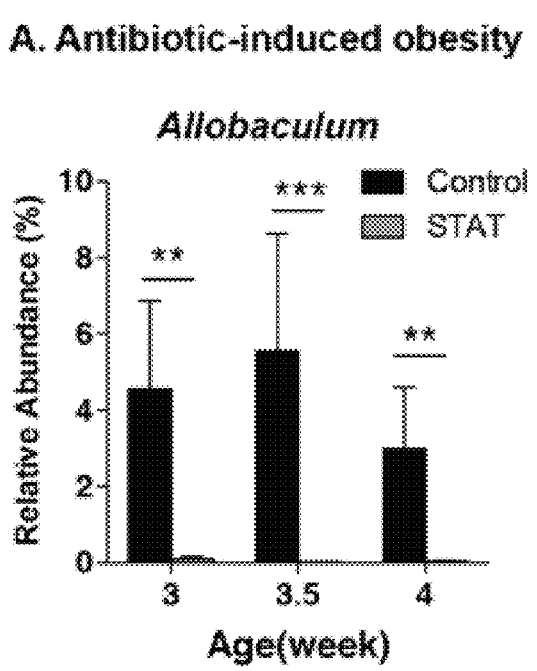
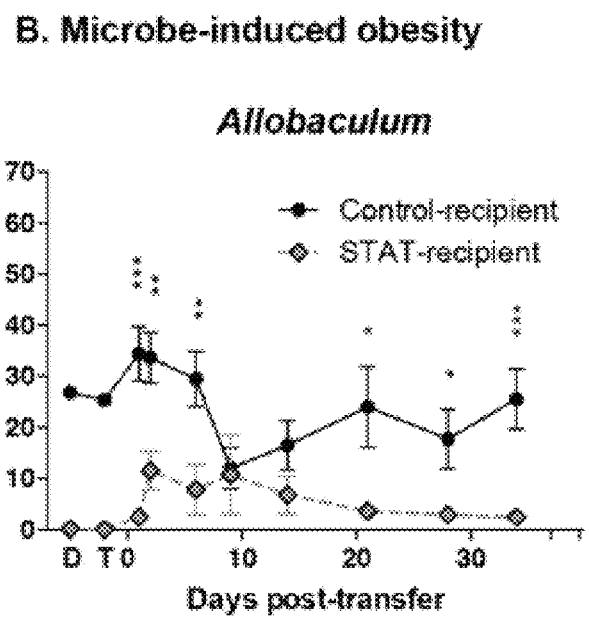
FIG. 3C
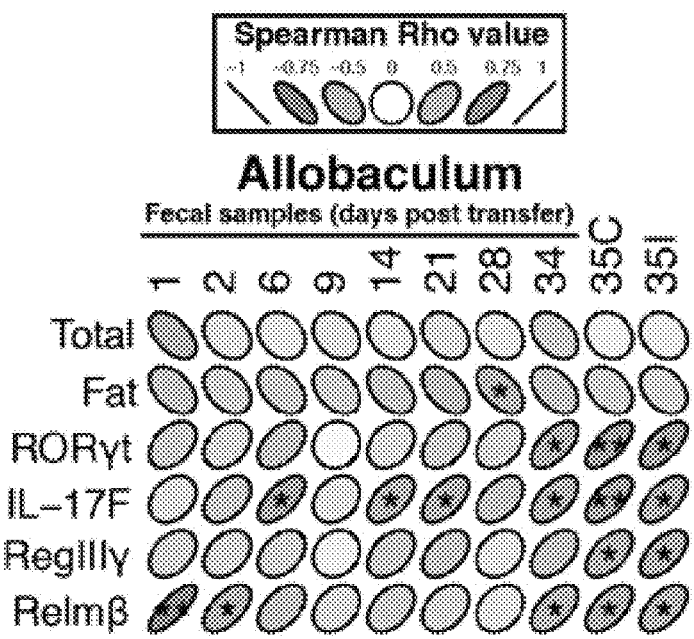

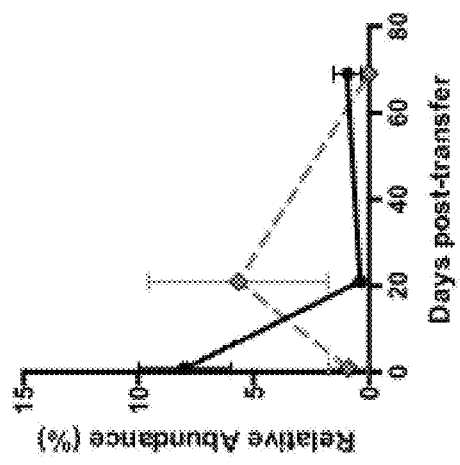
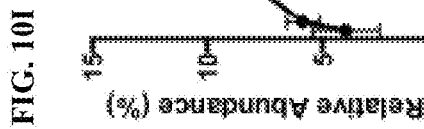
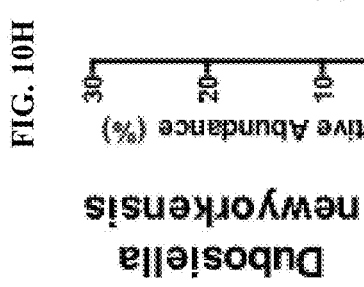
FIG. 10H  FIG. 10I  FIG. 10J

PROBIOTIC COMPOSITIONS FOR IMPROVING METABOLISM AND IMMUNITY

CROSS REFERENCE TO RELATED APPLICATIONS

This application claims priority to U.S. Provisional Patent Application Ser. No. 62/409,164, filed Oct. 17, 2016, and U.S. Provisional Patent Application Ser. No. 62/489,696, filed Apr. 25, 2017, each of which are hereby incorporated by reference in their entirety.

STATEMENT REGARDING FEDERALLY SPONSORED RESEARCH

This invention was made with government support under DK090989 and RR029893 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 13, 2017, is named 191Sequence_ST25.txt and is 4,393 bytes in size.

FIELD

The application relates to methods based on modulating mammalian intestinal microbiota and related probiotic and prebiotic compositions. Specifically, the application relates to the use of novel bacterial genera *Ileibacterium* and *Dubosiella* and closely related OTUs within the family Erysipelotrichaceae that resemble either *Ileibacterium* spp. or *Dubosiella* spp. with 90% 16S rRNA sequence identity, for modulating weight and intestinal inflammation and immunity (including modulating intestinal immune gene expression such as, e.g., modulating expression of RORγT, IL-17A, IL-17F, RegIIIγ, Relmβ, and Defβ), as well as for treatment and diagnosis of (i) obesity and related conditions such as metabolic syndrome and diabetes mellitus; (ii) allergic and autoimmune diseases, and (iii) gastrointestinal disorders (such as, e.g., inflammatory bowel disease (IBD), ulcerative colitis, Crohn's disease, and celiac disease).

BACKGROUND

Obesity has become widespread with increases in prevalence across all developed nations (Bouchard, C (2000) N Engl J Med. 343, 1888-9). According to the Center for Disease Control (CDC), over 60% of the United States population is overweight, and greater than 30% are obese. For affected persons, the problem often begins in childhood, and continues for life. Major contributors are believed to be increased consumption of high calorie foods and a more sedentary life style. However, neither of these alone or together are sufficient to explain the rise in obesity and subsequent or concomitant obesity-related disorders, such as, e.g., type II diabetes mellitus, metabolic syndrome, hypertension, cardiac pathology, and non-alcoholic fatty liver disease. According to the National Institute of Diabetes, Digestive and Kidney Diseases (NIDDK) approximately 280,000 deaths annually are directly related to obesity. The NIDDK further estimated that the direct cost of healthcare in the U.S. associated with obesity is $51 billion. In addition, Americans spend $33 billion per year on weight loss products. The prevalence of obesity continues to rise at alarming rates.

It is estimated that between 20-25% of American adults (about 47 million) have metabolic syndrome, a complex condition associated with an increased risk of vascular disease. Metabolic syndrome is also known as Syndrome X, metabolic syndrome X, insulin resistance syndrome, or Reaven's syndrome. Metabolic syndrome is generally believed to be a combination of disorders that affect a large number of people in a clustered fashion. The symptoms and features of the syndrome include at least three of the following conditions: diabetes mellitus type II; impaired glucose tolerance or insulin resistance; high blood pressure; central obesity and difficulty losing weight; high cholesterol; combined hyperlipidemia; including elevated LDL; decreased HDL; elevated triglycerides; and fatty liver (especially in concurrent obesity). Insulin resistance is typical of metabolic syndrome and leads to several of its features, including glucose intolerance, dyslipidemia, and hypertension. Obesity is commonly associated with the syndrome as is increased abdominal girth, highlighting the fact that abnormal lipid metabolism likely contributes to the underlying pathophysiology of metabolic syndrome.

Metabolic syndrome was codified in the United States with the publication of the National Cholesterol Education Program Adult Treatment Panel III (ATP III) guidelines in 2001. On a physiologic basis, insulin resistance appears to be responsible for the syndrome. However, insulin resistance can be defined in a myriad of different ways, including impaired glucose metabolism (reduced clearance of glucose and/or the failure to suppress glucose production), the inability to suppress lipolysis in tissues, defective protein synthesis, altered cell differentiation, aberrant nitric oxide synthesis affecting regional blood flow, as well as abnormal cell cycle control and proliferation, all of which have been implicated in the cardiovascular disease associated with metabolic syndrome. At least at present, there is no obvious molecular mechanism causing the syndrome, probably because the condition represents a failure of one or more of the many compensatory mechanisms that are activated in response to energy excess and the accumulation of fat.

Individuals at risk for metabolic syndrome include those who exhibit central obesity with increased abdominal girth (due to excess visceral adiposity) of about more than 35 inches in women and more than 40 inches in men. Individuals at risk for metabolic syndrome also include those that have a BMI greater than or equal to 30 kg/M2 and may also have abnormal levels of nonfasting glucose, lipids, and blood pressure.

Although certain bacterial associations have been examined for these and related conditions, the role of bacterial microbiota in these conditions has not been clearly understood or appreciated. Thus, there remains a need for methods for diagnosing, treating and preventing conditions such as obesity, metabolic syndrome, insulin-deficiency or insulin-resistance related disorders, glucose intolerance, diabetes mellitus, non-alcoholic fatty liver, abnormal lipid metabolism, atherosclerosis, and related disorders.

The average human body, consisting of about $10^{13}$ cells, has about ten times that number of microorganisms. The $\sim 10^{14}$ microbes that live in and on each of our bodies belong to all three domains of life on earth—bacteria, archaea and eukarya. The major sites for our indigenous microbiota are the intestinal tract, skin and mucosal surfaces such as nasal mucosa and vagina as well as the oropharynx. By far, the largest bacterial populations are in the colon. Bacteria make up most of the flora in the colon and 60% of the dry mass of feces. Probably more than 1000 different species live in the gut. However, it is probable that >90% of the bacteria come from less than 50 species. Fungi and protozoa also make up a part of the gut flora, but little is known about their activities. While the microbiota is highly extensive, it is barely characterized. Consequently, the Roadmap of the National Institutes of Health (NIH) includes the "Human Microbiome Project" to better characterize our microbial communities and the genes that they harbor (our microbiome) and better understand its relation to both human health and disease. Reviewed in Dethlefsen et al., Nature, 2007, 449:811-818; Turnbaugh et al., Nature, 2007, 449:804-810; Ley et al., Cell, 2006, 124:837-848.

Studies show that the relationship between gut flora and humans is not merely commensal (a non-harmful coexistence), but rather often is a mutualistic, symbiotic relationship. Although animals can survive with no gut flora, the microorganisms perform a host of useful functions, such as training the immune system, preventing growth of harmful species, regulating the development of the gut, fermenting unused energy substrates, metabolism of glycans and amino acids, synthesis of vitamins (such as biotin and vitamin K) and isoprenoids, biotransformation of xenobiotics, and producing hormones to direct the host to store fats. See, e.g., Gill et al., Science. 2006, 312:1355-1359; Zaneveld et al., Curr. Opin. Chem. Biol., 2008, 12(1):109-114; Guarner, Digestion, 2006, 73:5-12; Li et al., Proc. Natl. Acad. Sci. USA, 2008, 105:2117-2122; Hooper, Trends Microbiol., 2004, 12:129-134; Mazmanian et al., Cell, 2005, 122:107-118; Rakoff-Nahoum et al., Cell, 2004, 118:229-241. It is therefore believed that changes in the composition of the gut microbiota could have important health effects (Dethlefsen et al., PLoS Biology, 2008, 6(11):2383-2400). Indeed, a correlation between obesity and changes in gut microbiota has been observed (Ley et al., Proc Natl Acad Sci USA, 2005; 102:11070-11075; Bäckhed et al., Proc Natl Acad Sci USA, 2004; 101:15718-15723). Furthermore, in certain conditions, some microbial species are thought to be capable of directly causing disease by causing infection or increasing cancer risk for the host (O'Keefe et al., J Nutr. 2007; 137:175S-182S; McGarr et al., J Clin Gastroenterol., 2005; 39:98-109).

A substantial number of species in vertebrate microbiota is very hard to culture and analyze via traditional cultivation-based studies (Turnbaugh et al., Nature, 2007, 449:804-810; Eckburg et al., Science, 2005, 308:1635-1638). In contrast, broad-range PCR primers targeted to highly conserved regions makes possible the amplification of small subunit rRNA gene (16S rDNA) sequences from all bacterial species (Zoetendal et al., (2006) *Mol Microbiol* 59, 1639-1650), and the extensive and rapidly growing 16S rDNA database facilitates identification of sequences to the species or genus level (Schloss and Handelsman, (2004) *Microbiol Mol Biol Rev* 68, 686-691). Such techniques can also be used for identifying bacterial species in complex environmental niches (Smit et al., (2001) *Appl Environ Microbiol* 67, 2284-2291), including the human mouth, esophagus, stomach, intestine, feces, skin, and vagina, and for clinical diagnosis (Harris and Hartley, (2003) *J Med Microbial* 52, 685-691; Saglani et al., (2005) *Arch Dis Child* 90, 70-73).

Much of the microbiota is conserved from human to human, at least at the level of phylum and genus (for a general description of human microbiota see, e.g., Turnbaugh et al., Nature 2007; 449:804-810; Ley et al., Nature 2006; 444:1022-1023; Gao et al., Proc Natl Acad Sci USA 2007; 104:2927-32; Pei et al., Proc Natl Acad Sci USA 2004; 101:4250-4255; Eckburg et al., Science 2005; 308:1635-1638; Bik et al., Proc Natl Acad Sci USA 2006; 103:732-737). A major source of the human microbiota is from one's mother (for a summary of typical maternal colonization patterns see, e.g., Palmer et al., Plos Biology 2007; 5:e177; Raymond et al., Emerg Infect Dis 2004; 10:1816-21), and to a lesser extent from one's father and siblings (for examples of typical colonization patterns see, e.g., Raymond et al., Emerg Infect Dis 2004; 10:1816-21; Raymond et al., Plos One 2008; 3:e2259; Goodman et al., Am J Epidemiol 1996; 144:290-299; Goodman et al., Lancet 2000; 355:358-362). However, many of the natural mechanisms for the transmission of these indigenous organisms across generations and between family members have diminished with socioeconomic development. The impediments include: childbirth by caesarian section, reduced breast-feeding, smaller family size (fewer siblings), reduced household crowding with shared beds, utensils, in-door plumbing.

The vertebrate intestinal tract has a rich component of cells involved in immune responses. The nature of the microbiota colonizing experimental animals or humans affects the immune responses of the populations of reactive host cells (see, e.g., Ando et al., Infection and Immunity 1998; 66:4742-4747; Goll et al., Helicobacter. 2007; 12:185-92; Lundgren et al., Infect Immun. 2005; 73:523-531).

The vertebrate intestinal tract also is a locus in which hormones are produced. In mammals, many of these hormones related to energy homeostasis (including insulin, glucagon, leptin, and ghrelin) are produced by organs of the intestinal tract (see, e.g., Mix et al., Gut 2000; 47:481-6; Kojima et al., Nature 1999; 402:656-60; Shak et al., Obesity Surgery 2008; 18(9):1089-96; Roper et al., Journal of Clinical Endocrinology & Metabolism 2008; 93:2350-7; Francois et al., Gut 2008; 57:16-24; Cummings and Overduin, J Clin Invest 2007; 117:13-23; Bado et al., Nature 1998; 394:790-793).

Changing of the microbiota of the intestinal tract appears to affect the levels of some of these hormones (see, e.g., Breidert et al., Scand J Gastroenterol 1999; 34:954-61; Liew et al., Obes. Surg. 2006; 16:612-9; Nwokolo et al., Gut. 2003; 52, 637-640; Kinkhabwala et al., Gastroenterology 132:A208). The hormones affect immune responses (see, e.g., Matarese et al., J Immunol 2005; 174:3137-3142; Matsuda et al., J. Allergy Clin. Immunol. 2007; 119, S174) and adiposity (see, e.g., Tschop et al., Nature 2000; 407: 908-13).

Hydroxypropylmethylcellulose (HPMC) is modified cellulose fiber that produces viscous solutions in the gastrointestinal tract. It has been demonstrated that high viscosity (HV) HPMC consumed as part of a meal reduced peak blood glucose concentrations in subjects with type 2 diabetes compared with a cellulose control (Reppas et al., Diabetes Res. Clin. Pract., 1993, 22:61-9). It has been further demonstrated that HPMC reduced weight gain and insulin resistance in diet-induced obese mice and syrian hamsters fed a high fat (HF) diet similar in fat content to the American diet. (Hung et al., J Diab 2009; 1(3):194-206); Kim et al., FASEB J., 2009, Meeting Abstracts, Abstract 212.2).

PCT Pat. Appl. Publ. Nos. WO 2008/051793 and WO 2008/051794 disclose the use of HPMC and other water-soluble and water-insoluble cellulose derivatives for preventing or treating metabolic syndrome and related conditions. See also U.S. Pat. Nos. 5,576,306; 5,585,366; 6,899,892; 5,721,221. PCT Pat. Appl. Publ. No. WO 2004/022074 discloses the use of a composition comprising a non-glucose carbohydrate and soluble fiber or a mixture of pectin and soluble fiber for controlling metabolic syndrome, diabetes mellitus and obesity, and for the promotion of weight loss or maintenance of the desired body weight.

Obesity rates have been increasing in the United States (Ogden et al., JAMA 2014; 311:806), and recent studies have shown that the intestinal microbiota can increase fat mass (Turnbaugh et al., Nature 2006; 444:1027-1131) either through increased energy extraction or altered metabolic and inflammatory signaling (Cox et al., Cell Metab 2013; 17:883-894), suggesting that altered microbiota could be contributing to the obesity epidemic. In addition, farmers have been using low dose antibiotics for decades to increase weight gain in livestock, further indicating that alterations in the microbiota drive weight gain. Importantly, these effects are mediated by the microbiota, not antibiotics per se, since low dose antibiotics does not increase weight in germ-free animals (Coates et al., Br J Nutr 1963; 17:141-150).

The early-life microbiota plays a crucial developmental role in shaping metabolism, but the mechanism of action has yet to be fully understood. Mammalian species have co-evolved with their gut microbiota (Ley et al., Science 2008; 320:1647-1651) and much of the founding microbial population is transferred vertically from mother to child (Pantoja-Feliciano et al., ISME J 20132; 7:1112-1115). Disruptions to the early-life microbiota, such as from antibiotics or delivery by Cesarean section, significantly increase the risk of being overweight later in childhood in the human population (see, e.g., Azad et al., Int J Obes 2014; 1-9; Bailey et al., JAMA Pediatrics 2014, doi:10.1001/jamapediatrics.2014.1539; Ajslev et al., Int J Obes 2011; 35:522-529; Blustein et al., Int J Obes 2013; 37:900-906; Trasande et al., Int J Obes 2013; 37:16-23; Cox et al., Nat Rev Endocrinol 2015, 11:182-190). Antibiotic use is high in the United States, especially in infancy, with the average child receiving three courses of antibiotics by the age of two (Hicks et al., New Engl J Med 2013; 368:1461-1462), highlighting the need to understand specific microbial components that can program towards or protect from obesity.

The intestinal microbiota plays a role in shaping metabolism and immunity throughout life, and is recognized as a novel therapeutic target to stem the rising obesity epidemic, to boost immune responses, or to combat allergic and autoimmune diseases. However, microbiota-based therapies are limited to a narrow selection of bacteria and fungi. Because of the specificity of the microbiota-host interactions, it is imperative to obtain beneficial organisms in pure culture in order to consistently deliver them as therapeutics. Compared to the vast number of organisms in the GI tract, there are relatively few genera administered within probiotics available on the market today.

SUMMARY OF THE INVENTION

As specified in the Background section above, there is a great need in the art for diagnosing, preventing and/or treating diseases associated with altered metabolism and immunity. The present application addresses these and other needs.

In one aspect, the invention provides a probiotic composition comprising (i) bacteria from one or more strains of the genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp., and (ii) a carrier and/or excipient (e.g., vegetable cellulose, vegetable stearic acid, vegetable magnesium stearate, and/or silica) and/or one or more prebiotic agents which stimulate growth and/or activity and/or preserves viability of one or more bacteria present in the composition (e.g., galactose, β-N-acetyl-α-glucosamine, or any combinations thereof). In one embodiment, the bacteria in the probiotic composition are from one or more strains of the species *Ileibacterium valens* (*I. valens*) or a closely related OTU which has at least 90% sequence identity (and preferably at least 95% sequence identity, most preferably at least 99% sequence identity) to 16S rRNA of *I. valens* over its entire length or has at least 90% sequence identity (and preferably at least 95% sequence identity, most preferably at least 99% sequence identity) to any single V region of 16S rRNA of *I. valens* or has at least 90% sequence identity (and preferably at least 95% sequence identity, most preferably at least 99% sequence identity) to SEQ ID NO: 1 (NCBI GenBank Accession No. KU744404.1) over its entire length. In one specific embodiment, the bacteria in the probiotic composition are from the strain NYU-BL-A3 *Ileibacterium valens*, which has been deposited on Aug. 11, 2016 with Leibniz Institute DSMZ-German Collection of Microorganisms and Cell Cultures, Inhoffenstr. 7 B, 38124 Braunschweig, Germany under Accession No. DSM 33318. NYU-BL-A3 *Ileibacterium valens* was initially deposited under the name NYU-BL-A3 *Ileibacterium lipovorans*; however, the name was adjusted to *Ileibacterium valens* as discussed in Example 5. As such, reference to *Ileibacterium lipovorans* is synonymous with *Ileibacterium valens*.

In a related aspect, the invention provides, a probiotic composition comprising (i) bacteria from one or more strains of the genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp., and (ii) a carrier and/or excipient (e.g., vegetable cellulose, vegetable stearic acid, vegetable magnesium stearate, and/or silica) and/or one or more prebiotic agents which stimulate growth and/or activity and/or preserves viability of one or more bacteria present in the composition (e.g., galactose, β-N-acetyl-α-glucosamine, pyroglutamtamic acid, arginine, serine, glycine, or any combinations thereof). In one embodiment, the bacteria in the probiotic composition are from one or more strains of the species *Dubosiella* newyorkensis (*D. newy*) or a closely related OTU within the genus *Dubosiella* which has at least 90% sequence identity (and preferably at least 95% sequence identity, most preferably at least 99% sequence identity) to 16S rRNA of *D. newy* over its entire length or has at least 90% sequence identity (and preferably at least 95% sequence identity, most preferably at least 99% sequence identity) to any single V region of 16S rRNA of *D. newy* or has at least 90% sequence identity (and preferably at least 95% sequence identity, most preferably at least 99% sequence identity) to SEQ ID NO: 2 (NCBI GenBank Accession No. KU744405.1) over its entire length. In one specific embodiment, the bacteria in the probiotic composition are from the strain NYU-BL-A4 *Dubosiella newyorkensis*, which has been deposited on Jun. 20, 2016 with Leibniz Institute DSMZ-German Collection of Microorganisms and Cell Cultures, Inhoffenstr. 7 B, 38124 Braunschweig, Germany under Accession No. DSM 33317. In one embodiment, the probiotic composition further comprises (iii) bacteria from one or more strains of the genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. In one specific embodiment, the bacteria (iii) are from one or more strains of the species *Ileibacterium* valens (*I. valens*) or a closely related OTU which has at least 90% sequence identity (and preferably at least 95% sequence identity, most preferably at least 99% sequence identity) to 16S rRNA of *I. valens* over its entire length or has at least 90% sequence identity (and preferably at least 95% sequence identity, most preferably at least 99% sequence identity) to any single V region of 16S rRNA of *I. valens* or has at least 90% sequence identity (and preferably at least 95% sequence identity, most preferably at least 99% sequence identity) to SEQ ID NO: 1 (NCBI GenBank Accession No. KU744404.1) over its entire length. In one specific embodiment, the bacteria (iii) are from the strain NYU-BL-A3 *Ileibacterium* valens, which has been deposited on Aug. 11, 2016 with Leibniz Institute DSMZ-German Collection of Microorganisms and Cell Cultures, Inhoffenstr. 7 B, 38124 Braunschweig, Germany under Accession No. DSM 33318.

In one embodiment of any of the above compositions, the V region of 16S rRNA is the V4 region.

In one embodiment of any of the above compositions, the probiotic composition comprises one or more components selected from the group consisting of live bacterial cells, conditionally lethal bacterial cells, inactivated bacterial cells, killed bacterial cells, recombinant carrier strains, cell extract, and bacterially-derived products.

In one embodiment of any of the above compositions, the probiotic composition is in the form of a pill, a tablet, a capsule, a powder, or a suppository. In one specific embodiment, the contents of said pill, said tablet, said capsule, or said powder are formulated to be released in the intestine of a subject following oral administration of said pill, said tablet, said capsule, or said powder to said subject.

In another aspect, the invention provides a method for preventing weight gain or promoting weight loss in a subject in need thereof, said method comprising administering to the subject an effective amount of a probiotic or a prebiotic composition or a combination thereof, wherein said composition(s) (i) stimulates growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) stimulates growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In a related aspect, the invention provides a method for preventing and/or treating obesity and/or an associated condition (e.g., metabolic syndrome, diabetes mellitus, insulin-deficiency, insulin-resistance related disorders, glucose intolerance, non-alcoholic fatty liver, abnormal lipid metabolism, hypertension, or atherosclerosis) in a subject in need thereof, said method comprising administering to the subject an effective amount of a probiotic or a prebiotic composition or a combination thereof, wherein said composition(s) (i) stimulates growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) stimulates growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In another aspect, the invention provides a method for altering intestinal immune gene expression (e.g., increasing expression of RORγT, IL-17A, IL-17F, RegIIIγ, Relmβ, and/or Defβ) in a subject in need thereof, said method comprising administering to the subject an effective amount of a probiotic or a prebiotic composition or a combination thereof, wherein said composition(s) (i) stimulates growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) stimulates growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In a further aspect, the invention provides a method for increasing intestinal T cell immunity in a subject in need thereof, said method comprising administering to the subject an effective amount of a probiotic or a prebiotic composition or a combination thereof, wherein said composition(s) (i) stimulates growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) stimulates growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In yet another aspect, the invention provides a method for preventing and/or treating a gastrointestinal disorder (e.g., inflammatory bowel disease (IBD), ulcerative colitis, Crohn's disease, celiac disease, irritable bowel syndrome (IBS), infectious gastroenteritis, non-infectious gastroenteritis, food allergy, gastrointestinal graft versus host disease, small intestinal cancer, colon cancer, pouchitis, intestinal failure, short bowel syndrome, and antibiotic-associated diarrhea) in a subject in need thereof, said method comprising administering to the subject an effective amount of a probiotic or a prebiotic composition or a combination thereof, wherein said composition(s) (i) stimulates growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) stimulates growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In one embodiment of any of the above methods of the invention, said probiotic or prebiotic composition(s) (i) stimulates growth and/or activity of at least one strain of the bacterial species *Ileibacterium* valens (*I. valens*) or a closely related OTU which has at least 90% sequence identity (and preferably at least 95% sequence identity, most preferably at least 99% sequence identity) to 16S rRNA of *I. valens* over its entire length or has at least 90% sequence identity (and preferably at least 95% sequence identity, most preferably at least 99% sequence identity) to any single V region of 16S rRNA of *I. valens* or has at least 90% sequence identity (and preferably at least 95% sequence identity, most preferably at least 99% sequence identity) to SEQ ID NO: 1 (NCBI GenBank Accession No. KU744404.1) over its entire length in the gastrointestinal (GI) microbiota of the subject and/or (ii) stimulates growth and/or activity of at least one strain of the bacterial species *Dubosiella* newyorkensis (*D. newy*) or a closely related OTU within the genus *Dubosiella* which has at least 90% sequence identity (and preferably at least 95% sequence identity, most preferably at least 99% sequence identity) to 16S rRNA of *D. newy* over its entire length or has at least 90% sequence identity (and preferably at least 95% sequence identity, most preferably at least 99% sequence identity) to any single V region of 16S rRNA of *D. newy* or has at least 90% sequence identity (and preferably at least 95% sequence identity, most preferably at least 99% sequence identity) to SEQ ID NO: 2 (NCBI GenBank Accession No. KU1744405.1) over its entire length in the gastrointestinal (GI) microbiota of the subject.

In one embodiment of any of the above methods of the invention, said probiotic or prebiotic composition(s) (i) stimulates growth and/or activity of bacteria from the strain NYU-BL-A3 *Ileibacterium* valens, which has been deposited on Aug. 11, 2016 with Leibniz Institute DSMZ-German Collection of Microorganisms and Cell Cultures, Inhoffenstr. 7 B, 38124 Braunschweig, Germany under Accession No. DSM 33318 and/or (ii) stimulates growth and/or activity of bacteria from the strain NYU-BL-A4 *Dubosiella* newyorkensis, which has been deposited on Jun. 20, 2016 with Leibniz Institute DSMZ-German Collection of Microorganisms and Cell Cultures, Inhoffenstr. 7 B, 38124 Braunschweig, Germany under Accession No. DSM 33317 in the gastrointestinal (GI) microbiota of the subject.

In one embodiment of any of the above methods of the invention, the method comprises administering to the subject one or more probiotic compositions of the invention.

In one embodiment of any of the above methods of the invention, the method comprises administering to the subject at least two different bacterial strains, wherein (i) the first strain is from the genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp., and (ii) the second strain is from the genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. In one specific embodiment, (i) the first strain is from the species *Ileibacterium* valens (*I. valens*) or a closely related OTU which has at least 90% sequence identity (and preferably at least 95% sequence identity, most preferably at least 99% sequence identity) to 16S rRNA of *I. valens* over its entire length or has at least 90% sequence identity (and preferably at least 95% sequence identity, most preferably at least 99% sequence identity) to any single V region of 16S rRNA of *I. valens* or has at least 90% sequence identity (and preferably at least 95% sequence identity, most preferably at least 99% sequence identity) to SEQ ID NO: 1 (NCBI GenBank Accession No. KU744404.1) over its entire length and/or (ii) the second strain is from the species *Dubosiella* newyorkensis (*D. newy*) or a closely related OTU within the genus *Dubosiella* which has at least 90% sequence identity (and preferably at least 95% sequence identity, most preferably at least 99% sequence identity) to 16S rRNA of *D. newy* over its entire length or has at least 90% sequence identity (and preferably at least 95% sequence identity, most preferably at least 99% sequence identity) to any single V region of 16S rRNA of *D. newy* or has at least 90% sequence identity to SEQ ID NO: 2 (NCBI GenBank Accession No. KU744405.1) over its entire length. In one specific embodiment, (i) the first strain is the strain NYU-BL-A3 *Ileibacterium valens*, which has been deposited on Aug. 11, 2016 with Leibniz Institute DSMZ-German Collection of Microorganisms and Cell Cultures, Inhoffenstr. 7 B, 38124 Braunschweig, Germany under Accession No. DSM 33318 and/or (ii) the second strain is the strain NYU-BL-A4 *Dubosiella newyorkensis*, which has been deposited on Jun. 20, 2016 with Leibniz Institute DSMZ-German Collection of Microorganisms and Cell Cultures, Inhoffenstr. 7 B, 38124 Braunschweig, Germany under Accession No. DSM 33317.

In one embodiment of any of the above methods of the invention, the first strain and/or the second strain is provided in the form selected from the group consisting of live bacterial cells, conditionally lethal bacterial cells, inactivated bacterial cells, killed bacterial cells, recombinant carrier strains, cell extract, and bacterially-derived products.

In one embodiment of any of the above methods of the invention, the probiotic composition is in the form of a pill, a tablet, a capsule, a powder, or a suppository. In one specific embodiment, the contents of said pill, said tablet, said capsule, or said powder are formulated to be released in the intestine of a subject following oral administration of said pill, said tablet, said capsule, or said powder to said subject.

In a separate aspect, the invention provides a method for promoting weight gain in a subject in need thereof, said method comprising administering to the subject an effective amount of a compound or composition, wherein said compound or composition (i) inhibits growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) inhibits growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In another aspect, the invention provides a method for decreasing an intestinal inflammation in a subject in need thereof, said method comprising administering to the subject an effective amount of a compound or composition, wherein said compound or composition (i) inhibits growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) inhibits growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In another aspect, the invention provides a method for decreasing an intestinal T cell immune response and/or altering intestinal immune gene expression (e.g., decreasing expression of RORγT, IL-17A, IL-17F, RegIIIγ, Relmβ, and/or Defβ) in a subject in need thereof, said method comprising administering to the subject an effective amount of a compound or composition, wherein said compound or composition (i) inhibits growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) inhibits growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In a further aspect, the invention provides a method for preventing and/or treating an inflammatory or an autoimmune disorder (e.g., inflammatory bowel disease (IBD), asthma, celiac disease, eczema, allergic rhinitis, type 1 diabetes, systemic lupus erythematosis, rheumatoid arthritis, scleroderma, sarcoidosis, thyroiditis, multiple sclerosis, or myasthenia gravis) in a subject in need thereof, said method comprising administering to the subject an effective amount of a compound or composition, wherein said compound or composition (i) inhibits growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) inhibits growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In one embodiment of any of the above methods involving an inhibitory compound or composition, said compound or composition (i) inhibits growth and/or activity of at least one strain of the bacterial species *Ileibacterium* valens (*I. valens*) or a closely related OTU which has at least 90% sequence identity (and preferably at least 95% sequence identity, most preferably at least 99% sequence identity) to 16S rRNA of *I. valens* over its entire length or has at least 90% sequence identity (and preferably at least 95% sequence identity, most preferably at least 99% sequence identity) to any single V region of 16S rRNA of *I. valens* or has at least 90% sequence identity (and preferably at least 95% sequence identity, most preferably at least 99% sequence identity) to SEQ ID NO: 1 (NCBI GenBank Accession No. KU744404.1) over its entire length in the gastrointestinal (GI) microbiota of the subject and/or (ii) inhibits growth and/or activity of at least one strain of the bacterial species *Dubosiella newyorkensis* (*D. newy*) or a closely related OTU within the genus *Dubosiella* which has at least 90% sequence identity (and preferably at least 95% sequence identity, most preferably at least 99% sequence identity) to 16S rRNA of *D. newy* over its entire length or has at least 90% sequence identity (and preferably at least 95% sequence identity, most preferably at least 99% sequence identity) to any single V region of 16S rRNA of *D. newy* or has at least 90% sequence identity (and preferably at least 95% sequence identity, most preferably at least 99% sequence identity) to SEQ ID NO: 2 (NCBI GenBank Accession No. KU1744405.1) over its entire length in the gastrointestinal (GI) microbiota of the subject. In one specific embodiment, said compound or composition (i) inhibits growth and/or activity of bacteria from the strain NYU-BL-A3 *Ileibacterium* valens, which has been deposited on Aug. 11, 2016 with Leibniz Institute DSMZ-German Collection of Microorganisms and Cell Cultures, Inhoffenstr. 7 B, 38124 Braunschweig, Germany under Accession No. DSM 33318 and/or (ii) inhibits growth and/or activity of bacteria from the strain NYU-BL-A4 *Dubosiella newyorkensis*, which has been deposited on Jun. 20, 2016 with Leibniz Institute DSMZ-German Collection of Microorganisms and Cell Cultures, Inhoffenstr. 7 B, 38124 Braunschweig, Germany under Accession No. DSM 33317 in the gastrointestinal (GI) microbiota of the subject.

In one embodiment of any of the above methods involving an inhibitory compound, said compound is a beta-lactam antibiotic (e.g., penicillin).

In one embodiment of any of the above methods of the invention, the probiotic composition is administered conjointly with a prebiotic which stimulates growth and/or activity and/or preserves viability of one or more bacterial strains contained in the probiotic composition.

In a separate embodiment, the invention provides a method for diagnosing predisposition to obesity and/or associated condition (e.g., metabolic syndrome, diabetes mellitus, insulin-deficiency, insulin-resistance related disorders, glucose intolerance, non-alcoholic fatty liver, abnormal lipid metabolism, hypertension, and atherosclerosis) in a subject, said method comprising (a) determining the level of (i) at least one strain of the bacterial genus *Ileibacterium* or a closely related OTU within the family Erysipelotrichaceae which has at least 90% (or at least 95%, or at least 99%) sequence identity to 16S rRNA of *Ileibacterium* spp. over its entire length or has at least 90% (or at least 95%, or at least 99%) sequence identity to any single V region of 16S rRNA of *Ileibacterium* spp. in the gastrointestinal (GI) microbiota of the subject and/or (ii) at least one strain of the bacterial genus *Dubosiella* or a closely related OTU within the family Erysipelotrichaceae which has at least 90% (or at least 95%, or at least 99%) sequence identity to 16S rRNA of *Dubosiella* spp. over its entire length or has at least 90% (or at least 95%, or at least 99%) sequence identity to any single V region of 16S rRNA of *Dubosiella* spp. in the gastrointestinal (GI) microbiota of the subject, and (b) comparing the level determined in step (a) to the level of the same bacteria in the gastrointestinal (GI) microbiota of healthy controls, and (c) identifying that the subject is predisposed to obesity and/or associated conditions wherein the level of at least one of the strains measured in step (a) is at least 50% lower than in healthy controls.

In another aspect, the invention provides a method for diagnosing predisposition to gastrointestinal and/or inflammatory disorders (e.g., inflammatory bowel disease (IBD), ulcerative colitis, Crohn's disease, celiac disease, irritable bowel syndrome (IBS), infectious gastroenteritis, non-infectious gastroenteritis, food allergy, gastrointestinal graft versus host disease, small intestinal cancer, colon cancer, pouchitis, intestinal failure, short bowel syndrome, and antibiotics-associated diarrhea) in a subject, said method comprising (a) determining the level of (i) at least one strain of the bacterial genus *Ileibacterium* or a closely related OTU within the family Erysipelotrichaceae which has at least 90% (or at least 95%, or at least 99%) sequence identity to 16S rRNA of *Ileibacterium* spp. over its entire length or has at least 90% (or at least 95%, or at least 99%) sequence identity to any single V region of 16S rRNA of *Ileibacterium* spp. in the gastrointestinal (GI) microbiota of the subject and/or (ii) at least one strain of the bacterial genus *Dubosiella* or a closely related OTU within the family Erysipelotrichaceae which has at least 90% (or at least 95%, or at least 99%) sequence identity to 16S rRNA of *Dubosiella* spp. over its entire length or has at least 90% (or at least 95%, or at least 99%) sequence identity to any single V region of 16S rRNA of *Dubosiella* spp. in the gastrointestinal (GI) microbiota of the subject, and (b) comparing the level determined in step (a) to the level of the same bacteria in the gastrointestinal (GI) microbiota of healthy controls, and (c) identifying that the subject is predisposed to gastrointestinal and/or inflammatory disorders wherein the level of at least one of the strains measured in step (a) is at least 50% higher than in healthy controls.

In one embodiment of any of the above diagnostic methods, step (a) involves determining the level of (i) at least one strain of the bacterial species *Ileibacterium* valens (I. valens) or a closely related OTU which has at least 90% (or at least 95%, or at least 99%) sequence identity to 16S rRNA of *I. valens* over its entire length or has at least 90% (or at least 95%, or at least 99%) sequence identity to any single V region of 16S rRNA of *I. valens* or has at least 90% (or at least 95%, or at least 99%) sequence identity to SEQ ID NO: 1 (NCBI GenBank Accession No. KU744404.1) over its entire length in the gastrointestinal (GI) microbiota of the subject and/or (ii) at least one strain of the bacterial species *Dubosiella newyorkensis* (*D. newy*) or a closely related OTU within the genus *Dubosiella* which has at least 90% (or at least 95%, or at least 99%) sequence identity to 16S rRNA of *D. newy* over its entire length or has at least 90% (or at least 95%, or at least 99%) sequence identity to any single V region of 16S rRNA of *D. newy* or has at least 90% (or at least 95%, or at least 99%) sequence identity to SEQ ID NO:

2 (NCBI GenBank Accession No. M1744405.1) over its entire length in the gastrointestinal (GI) microbiota of the subject.

In one embodiment of any of the above diagnostic methods, step (a) involves determining the level of (i) at least one strain of the bacterial species *Ileibacterium* valens (*I. valens*) in the gastrointestinal (GI) microbiota of the subject and/or (ii) at least one strain of the bacterial species *Dubosiella newyorkensis* (*D. newy*) in the gastrointestinal (GI) microbiota of the subject. In one specific embodiment, step (a) involves determining the level of (i) bacteria from the strain NYU-BL-A3 *Ileibacterium* valens, which has been deposited on Aug. 11, 2016 with Leibniz Institute DSMZ-German Collection of Microorganisms and Cell Cultures, Inhoffenstr. 7 B, 38124 Braunschweig, Germany under Accession No. DSM 33318 and/or (ii) bacteria from the strain NYU-BL-A4 *Dubosiella newyorkensis*, which has been deposited on Jun. 20, 2016 with Leibniz Institute DSMZ-German Collection of Microorganisms and Cell Cultures, Inhoffenstr. 7 B, 38124 Braunschweig, Germany under Accession No. DSM 33317 in the gastrointestinal (GI) microbiota of the subject.

In one embodiment of any of the methods of the invention, the gastrointestinal (GI) microbiota is selected from the group consisting of cecal, ileal, colonic, and fecal microbiota.

In one embodiment of any of the methods of the invention, the V region of 16S rRNA is the V4 region.

In one embodiment of any of the methods of the invention, the subject is human.

In one embodiment of any of the methods of the invention, the subject is an infant or a child.

These and other aspects of the present invention will be apparent to those of ordinary skill in the art in the following description, claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A: Study design: Both male and female mice received 4 (4-LDP), 8 (8-LDP), or 28 (28-LDP) weeks of low-dose penicillin (LDP), or no antibiotics (control). FIG. 1Q: Flow cytometry of ileal and colonic tissue from male control and LDP mice at 8-weeks of age (n=4) for IL-17 and IL-22, *$p<0.05$ t-test. Graphs are displayed as mean±SEM.

FIG. 2A-2E. Microbe-Induced Obesity: Metabolic and immunologic consequences of transferring LDP-altered microbiota. Cecal microbiota from 3 control and 3 LDP 18-week old female C57B/L6J mice were collected, pooled, and transferred to 3-week old germ-free female Swiss-Webster mice by oral gavage. FIG. 2A: Microbiota donors were selected based on the median total mass determined by DEXA scanning at week 16. FIG. 2B: Total, lean, and fat mass in the now-conventionalized germ-free control- and LDP-microbiota recipient mice (n=7 and 8, respectively), measured by DEXA scanning over the 35-day experiment. (FIG. 2C-FIG. 2D) Ileal gene expression in microbiota donor (n=3 CTL, LDP) (FIG. 2C) and recipient (n=7 & 8, CTL, LDP, respectively) (FIG. 2D) mice measured by qPCR, p-values listed from t-tests. FIG. 2E: Expression of ileal genes significantly different between control- and LDP recipients (n=4 each), measured by the Nanostring Mouse Immunology Kit, ($p<0.05$, t-test). Biological functions predicted to be significantly increased ($p<0.05$, $z>121$) in LDP mice based on Ingenuity Pathway Analysis of Nanostring expression values.

FIG. 3A-3C. Identification of *Allobaculum* as a taxon of interest in models of antibiotic- and microbe-induced obesity. Mice were treated with sub-therapeutic antibiotic treatment (STAT) with low-dose penicillin (LDP), and fat mass was significantly elevated over time then microbiota from experiment 1 control and STAT mice were transferred to germ-free mice. STAT-microbiota recipients gained more fat than control-microbiota recipients. Altered microbiota were identified using high-throughput 16S rRNA sequencing. Bacterial taxonomy was assigned using the Greengenes database and the RDP classifier set to a confidence threshold of 50%, which is relatively lenient, and has the possibility for mis-identifying bacteria in closely related taxonomic lineages. (FIG. 3A-FIG. 3B) *Allobaculum* is significantly decreased in STAT mice (FIG. 3A) and STAT microbiota recipients (FIG. 3B). *$p<0.05$, $p<0.01$, *$p<0.001$, Mann-Whitney U test. FIG. 3C: The levels of *Allobaculum* over time have a consistent negative correlation with total and fat mass, while they have a consistent and significant correlation with the expression of markers of ileal immune defense, including RORγT, IL-17F, RegIIIγ, and Relmβ, spearman correlation Rho values are plotted as an ellipse and significance levels are noted with an *.

FIG. 4A-4I. Detection of *Allobaculum* in 956 murine intestinal 16S rRNA sequences. Total depth of coverage of all taxa (FIG. 4A), depth of coverage of *Allobaculum* (FIG. 4B), and overlay of both, rank ordered by total depth of coverage (FIG. 4C). FIG. 4D: Pearson correlation of *Allobaculum* and total depth of coverage, $p<0.0001$. FIG. 4E: Rank order of the prevalence of the 523 different *Allobaculum* OTUs detected. FIG. 4F: Rank order of the prevalence of the top 10 *Allobaculum* OTUs. FIG. 4G: Abundance of the top 10 *Allobaculum* OTUs, which includes all OTUs with sequence counts >1000. (FIG. 4H) Abundance of OTUs with sequence counts between 100 and 1000.

FIG. 10A-10M. Associations of *Ileibacterium, Dubosiella*, and *Faecalibaculum* in models of antibiotic- and microbe-induced obesity. FIG. 10A: In the experiment 1, mice were given sub-therapeutic antibiotic treatment, which significantly increased fat mass over time.

FIG. 10B: In experiment 2, microbiota from experiment 1 control and STAT mice were transferred to germ-free recipients, which similarly developed increased fat mass. FIG. 10C: In experiment 3, a new cohort of germ-free mice were colonized with microbiota from experiment 2 control- and STAT-microbiota recipient mice, however fat mass did not differ between groups, and both were lean, as compared to the lean controls in experiment 2 (FIG. 10D). In both antibiotic- and microbiota-induced obesity, *Ileibacterium* and *Dubosiella* were increased in the lean mice (FIG. 10E, FIG. 10F, FIG. 10H, FIG. 10I), and also at high levels in both groups of lean mice in experiment 3 (FIG. 10G, FIG. 10J). *Faecalibaculum* was increased in the lean controls in antibiotic-induced obesity (FIG. 10K), however, it was higher in the obese STAT-microbiota recipients in experiment 2 (FIG. 10L) demonstrating that it is not sufficient to prevent accumulation of excess adiposity. (FIG. 10M) *Faecalibaculum* was also increased in a new cohort of germ-free mice, which were colonized with microbiota from experiment 2 control- and STAT-microbiota recipient mice.

DETAILED DESCRIPTION

Figure 1A:
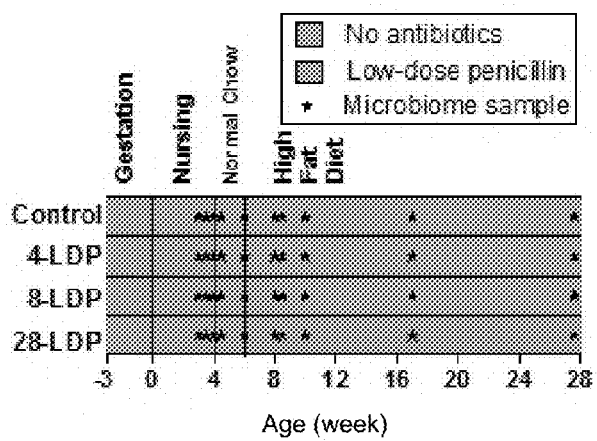
FIG. 1A-1Q. Early-life low-dose penicillin (LDP) induces lasting changes in adult body composition.

The present invention provides methods and compositions for modulating weight and preventing and/or treating diseases associated with altered metabolism and immunity, such as for example and not limitation, obesity, metabolic syndrome, diabetes mellitus, insulin-deficiency or insulin-resistance related disorders, glucose intolerance, non-alcoholic fatty liver, abnormal lipid metabolism, asthma, celiac disease, type 1 diabetes, lupus, rheumatoid arthritis, spondylitis, systemic lupus erythematosis (SLE), scleroderma, periarteritis, multiple sclerosis, food allergies, eczema, thyroiditis, and other allergic and autoimmune diseases.

In a mouse model, the present inventors have demonstrated that early-life disruption to the microbiota from low-dose antibiotic exposure results in lasting elevations in weight and adiposity (Cho et al., Nature 2012; 488:621-626; Cox et al., Cell 2014; 158:705-721), and these effects could be mediated by the microbiota alone (Cox et al., Cell 2014; 158:705-721), which the inventors have termed microbe-induced obesity ("MIO") (Cox et al., Cell Metab 2013; 17:883-894). Remarkably, the changes to the microbiota were transient, but increases in total and fat mass were life-long, indicating that infancy is a critical window of host-microbe metabolic interaction. It was also demonstrated that the combination of high fat diet and early-life microbiota disruption are additive, suggesting that specific microbial dietary responses are critical determinants of body composition.

Using the model of MIO described in the Examples section, below, the present inventors have now identified and isolated novel bacterial genera *Ileibacterium* and *Dubosiella* (as well as species *Ileibacterium* valens and *Dubosiella newyorkensis*) and closely related OTUs within the family Erysipelotrichaceae and have demonstrated the usefulness of these taxa for altering host metabolism and immunity.

Definitions

As used herein, the terms "microbe" or "microorganism" encompass both prokaryotic organisms including bacteria and archaea, and eukaryotic organisms, including fungi, present in mammalian microbiota.

The terms "intestinal microbiota" or "intestinal flora" or "intestinal microbiome" are used interchangeably and refer to the microorganisms that colonize the intestines.

Specific changes in GI microbiota discussed herein can be detected using various methods, including without limitation quantitative PCR or high-throughput sequencing methods which detect over- and under-represented genes in the total bacterial population (e.g., 454-sequencing for community analysis; screening of microbial 16S ribosomal RNAs (16S rRNA), etc.), or transcriptomic or proteomic studies that identify lost or gained microbial transcripts or proteins within total bacterial populations. See, e.g., U.S. Patent Publication No. 2010/0074872; Eckburg et al., Science, 2005, 308:1635-8; Costello et al., Science, 2009, 326:1694-7; Grice et al., Science, 2009, 324:1190-2; Li et al., Nature, 2010, 464: 59-65; Bjursell et al., Journal of Biological Chemistry, 2006, 281:36269-36279; Mahowald et al., PNAS, 2009, 14:5859-5864; Wikoff et al., PNAS, 2009, 10:3698-3703.

The term "restoring normal microbiota" is used herein to refer to restoring microbiota of a subject (e.g., skin, oral, nasal, gastrointestinal, or any other mucosal microbiota) to the level of bioactivity and diversity of corresponding microbiota of a healthy subject. This may also be considered as normalizing the microbiota, populating the microbiota, populating normal microbiota, preventing the onset of dysbiosis, or augmenting the growth of at least one type of bacteria in a subject.

As used herein, the term "dysbiosis" refers to a microbial imbalance on or inside the body. Dysbiosis is most commonly reported as a condition in the GI tract. It has been reported to be associated with a wide variety of illnesses, such as, e.g., irritable bowel syndrome, inflammatory bowel disease, chronic fatigue syndrome, obesity, rheumatoid arthritis, ankylosing spondylitis, bacterial vaginosis, colitis, etc. Dysbiosis can result from, e.g., antibiotic exposure as well as other causes, e.g., infections with intestinal pathogens including viruses, bacteria and eukaryotic parasites.

Specific taxa and changes in microbiota discussed herein can be detected using various methods, including without limitation quantitative PCR (qPCR) or high-throughput sequencing (e.g., shotgun metagenome sequencing) methods which detect over- and under-represented genes in the total bacterial population (e.g., 454-sequencing for community analysis; screening of microbial 16S ribosomal RNAs (16S rRNA), etc.), or transcriptomic or proteomic studies that identify lost or gained microbial transcripts or proteins within total bacterial populations, or metabolomics. See, e.g., U.S. Patent Publication No. 2010/0074872; Eckburg et al., Science, 2005, 308:1635-8; Costello et al., Science, 2009, 326:1694-7; Grice et al., Science, 2009, 324:1190-2; Li et al., Nature, 2010, 464: 59-65; Bjursell et al., Journal of Biological Chemistry, 2006, 281:36269-36279; Mahowald et al., PNAS, 2009, 14:5859-5864; Wikoff et al., PNAS, 2009, 10:3698-3703.

As used herein, the term "16S rRNA sequencing" refers to the sequencing of 16S ribosomal RNA (rRNA) gene sequences by using primers such as universal primers and/or species-specific primers to identify the bacteria present in a sample. 16S rRNA genes contain both highly conserved sites and hypervariable regions that can provide species-specific signature sequences useful for identification of bacteria. Such universal primers are well known in the art.

As used herein, the term "operational taxonomic unit" or "OTU" refers to group of bacterial sequences that differ among each other in <97% identity. A "type" or a plurality of "types" of bacteria includes an OTU or a plurality of different OTUs, and also encompasses differences in species, genus, family or order of bacteria. The specific genetic sequence may be the 16S rRNA sequence or a portion of the 16S rRNA sequence or it may be a functionally conserved housekeeping gene found broadly across the eubacterial kingdom.

As used herein, the term "probiotic" refers to a substantially pure bacteria (i.e., a single isolate, of, e.g., live bacterial cells, conditionally lethal bacterial cells, inactivated bacterial cells, killed bacterial cells, spores, recombinant carrier strains), or a mixture of desired bacteria, bacteria components or bacterial extract, or bacterially-derived products (natural or synthetic bacterially-derived products such as, e.g., bacterial antigens or metabolic products) and may also include any additional components that can be administered to a mammal. Such compositions are also referred to herein as bacterial inoculants" or "microbiota inoculants". Probiotics or bacterial inoculant compositions of the invention may be administered with a buffering agent to allow the bacteria to survive in the acidic environment of the stomach, i.e., to resist low pH and to grow in the intestinal environment. Such buffering agents include sodium bicarbonate, juice, milk, yogurt, infant formula, and other dairy products.

As used herein, the term "prebiotic" refers to an agent that increases the number and/or activity of one or more desired bacteria, enhancing their growth. Non-limiting examples of prebiotics useful in the methods of the present invention include fructooligosaccharides (e.g., oligofructose, inulin, inulin-type fructans), galactooligosaccharides, human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, other five- and six-carbon sugars (such as arabinose, maltose, lactose, sucrose, cellobiose, etc.), amino acids, alcohols, resistant starch (RS), water-soluble cellulose derivatives (most preferably, methylcellulose, methyl ethyl cellulose, hydroxyethyl cellulose, ethyl hydroxyethyl cellulose, cationic hydroxyethyl cellulose, hydroxypropyl cellulose, hydroxyethyl methylcellulose, hydroxypropyl methylcellulose, and carboxymethyl cellulose), water-insoluble cellulose derivatives (most preferably, ethyl cellulose), and mixtures thereof. See, e.g., Ramirez-Farias et al., Br J Nutr (2008) 4:1-10; Pool-Zobel and Sauer, J Nutr (2007), 137: 2580S-2584S.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein, the term "therapeutically effective amount" refers to the amount of a bacterial inoculant or a compound (e.g., a prebiotic or a probiotic) that, when administered to a subject for treating (e.g., preventing or ameliorating) a state, disorder or condition, is sufficient to effect such treatment. The "therapeutically effective amount" will vary depending, e.g., on the compound, bacteria or analogues administered as well as the disease, its severity, and physical conditions and responsiveness of the subject to be treated.

As used herein, the phrase "pharmaceutically acceptable" refers to molecular entities and compositions that are generally regarded as physiologically tolerable.

As used herein, the term "combination" of a bacterial inoculant, probiotic, analogue, or prebiotic compound and at least a second pharmaceutically active ingredient means at least two, but any desired combination of compounds can be delivered simultaneously or sequentially (e.g., within a 24 hour period).

Within the meaning of the present invention, the term "conjoint administration" is used to refer to administration of a probiotic and a prebiotic simultaneously in one composition, or simultaneously in different compositions, or sequentially (preferably, within a 24 hour period).

The terms "patient", "individual", "subject", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

As used herein, the term "stimulate" when used in connection with growth and/or activity of bacteria encompasses the term "enhance".

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The terms "a," "an," and "the" do not denote a limitation of quantity, but rather denote the presence of "at least one" of the referenced item.

The practice of the present invention employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J. Additional techniques are explained, e.g., in U.S. Pat. No. 7,912,698 and U.S. Patent Appl. Pub. Nos. 2011/0202322 and 2011/0307437.

Novel Bacterial Species and Probiotic Compositions of the Invention

The present invention provides probiotic compositions comprising bacteria from one or more strains from one or two new bacterial genera within the family Erysipelotrichaceae which the present inventors have isolated from gastrointestinal (GI) microbiota in pure culture, i.e., *Ileibacterium* and *Dubosiella*. The present invention further provides probiotic compositions comprising bacteria from one or more strains from one or two new bacterial species within the family Erysipelotrichaceae which the present inventors have isolated from gastrointestinal (GI) microbiota in pure culture, i.e., *Ileibacterium* valens and *Dubosiella newyorkensis*. In one embodiment, the invention provides a probiotic composition comprising bacteria from strain NYU-BL-A3 *Ileibacterium* valens, which has been deposited on Aug. 11, 2016 with Leibniz Institute DSMZ-German Collection of Microorganisms and Cell Cultures, Inhoffenstr. 7 B, 38124 Braunschweig, Germany under Accession No. DSM 33318. NYU-BL-A3 *Ileibacterium* valens was initially deposited under the name NYU-BL-A3 *Ileibacterium lipovorans*; however, the name was adjusted to *Ileibacterium* valens as discussed in Example 5. As such, reference to *Ileibacterium lipovorans* is synonymous with *Ileibacterium* valens. In another embodiment, the invention provides a probiotic composition comprising bacteria from strain NYU-BL-A4 *Dubosiella newyorkensis*, which has been deposited on Jun. 20, 2016 with Leibniz Institute DSMZ-German Collection of Microorganisms and Cell Cultures, Inhoffenstr. 7 B, 38124 Braunschweig, Germany under Accession No. DSM 33317. In one specific embodiment, the probiotic composition comprises at least two different bacterial strains, wherein at least one strain is from species *Ileibacterium* valens and at least one strain is from species *Dubosiella newyorkensis*.

In another embodiment, the invention provides probiotic compositions comprising bacteria from one or more strains from one or more "*Allobaculum*-like" OTUs (ALO) which are independently characterized by, i.e., at least 95%, 96%, 97%, 98%, 99% or including 100% sequence identity to sequences listed in SEQ ID NOS: 1 and 2 or 16S rRNA sequences of *Ileibacterium* valens or *Dubosiella newyorkensis* species. In one embodiment, the OTUs may be characterized by one or more of the variable regions of the 16S rRNA sequence (V1-V9). These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. (See, e.g., Brosius et al., Complete nucleotide sequence of a 16S ribosomal RNA gene from *Escherichia coli*, PNAS 75(10):4801-4805 (1978); Kuczynski et al., Experimental and analytical tools for studying the human microbiome and references cited therein, Nature Reviews Genetics, 2012, 13:47-57). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU.

In one embodiment, the probiotic composition comprises bacteria from at least two different bacterial species disclosed herein (e.g., *Ileibacterium* spp. or *Dubosiella* spp.). Within a given composition, different bacterial strains can be contained in equal amounts (even combination) or in various proportions (uneven combinations) needed for achieving the maximal biological activity. For example, in a bacterial composition with two bacterial strains, the strains may be present in from a 1:10,000 ratio to a 1:1 ratio, from a 1:10,000 ratio to a 1:1,000 ratio, from a 1:1,000 ratio to a 1:100 ratio, from a 1:100 ratio to a 1:50 ratio, from a 1:50 ratio to a 1:20 ratio, from a 1:20 ratio to a 1:10 ratio, from a 1:10 ratio to a 1:1 ratio. For bacterial compositions comprising at least three bacterial strains, the ratio of strains may be chosen pairwise from ratios for bacterial compositions with two strains. For example, in a bacterial composition comprising bacterial strains A, B, and C, at least one of the ratios between strain A and B, the ratio between strain B and C, and the ratio between strain A and C may be chosen, independently, from the pairwise combinations above. In one specific embodiment, the invention encompasses administering two or more bacteria-containing compositions to the same subject. Such compositions can be administered simultaneously or sequentially.

The probiotic compositions of the invention can comprise, without limitation, e.g., live bacterial cells, conditionally lethal bacterial cells, inactivated bacterial cells, killed bacterial cells, spores (e.g., germination-competent spores), recombinant carrier strains, cell extract, and bacterially-derived products (natural or synthetic bacterially-derived products such as, e.g., bacterial antigens or bacterial metabolic products).

Probiotic compositions of the invention can comprise (i) a carrier and/or excipient and/or (ii) one or more prebiotic agents which stimulate growth and/or activity of one or more bacteria present in the composition. In one specific embodiment, the probiotic composition comprises an excipient or a carrier that optimizes the seeding of one or more bacterial strains contained in said probiotic composition.

In one embodiment of any of the methods involving administration of a probiotic composition, said probiotic composition is reconstituted from a lyophilized preparation. In one embodiment of any of the methods involving administration of a probiotic composition, said probiotic composition comprises a buffering agent to adjust pH to 7.0.

Bacterial strains administered in probiotic compositions according to the methods of the present invention can comprise live bacteria. One or several different bacterial inoculants can be administered simultaneously or sequentially (including administering at different times). Such bacteria can be isolated from gastrointestinal (GI) microbiota and grown in culture using, e.g., techniques described in the Examples section, below. The present invention also comprises administering "bacterial analogues", such as recombinant carrier strains expressing one or more heterologous genes derived from the relevant bacterial species. The use of such recombinant bacteria may allow the use of lower therapeutic amounts due to higher protein expression. Non-limiting examples of recombinant carrier strains useful in the methods of the present invention include *E. coli* and *Lactobacillus, Bacteroides* and *Oxalobacter*. Methods describing the use of bacteria for heterologous protein delivery are described, e.g., in U.S. Pat. No. 6,803,231.

In certain embodiments, a conditional lethal bacterial strain can be utilized as the inoculant or to deliver a recombinant construct. Such a conditional lethal bacteria survives for a limited time typically when provided certain nutritional supplements. It is contemplated that such a supplement could be a liquid, formulated to contain the nutritional component necessary to keep the bacteria alive. It is further contemplated that a patient/subject would drink such a supplement in intervals to keep the bacteria alive. Once the supplement is depleted, the conditional lethal bacteria die. Methods relating to conditional lethal strains of *H. pylori* are described in U.S. Pat. No. 6,570,004.

Spores used in the compositions of the invention can be isolated, for example, by solvent treatments (e.g., using partially miscible, fully miscible or an immiscible solvent), chromatographic treatments (e.g., using hydrophobic interaction chromatography (HIC) or an affinity chromatography), mechanical treatments (e.g., blending, mixing, shaking, vortexing, impact pulverization, and sonication), filtration treatments, thermal treatments (e.g., 30 seconds in a 100° C. environment followed by 10 minutes in a 50° C.), irradiation treatments (e.g., with ionizing radiation, typically gamma irradiation, ultraviolet irradiation or electron beam irradiation provided at an energy level sufficient to kill pathogenic materials while not substantially damaging the desired spore populations), centrifugation and density separation treatments (e.g., using density or mobility gradients or cushions (e.g., step cushions), such as, e.g., CsCl, Percoll, Ficoll, Nycodenz, Histodenz or sucrose gradients). It is generally desirable to retain the spore populations under non-germinating and non-growth promoting conditions and media, in order to minimize the growth of pathogenic bacteria present in the spore populations and to minimize the germination of spores into vegetative bacterial cells.

The compositions of the invention can comprise a carrier and/or excipient. While it is possible to use a bacterial inoculant or compound of the present invention for therapy as is, it may be preferable to administer it in a pharmaceutical formulation, e.g., in admixture with a suitable pharmaceutical excipient and/or carrier selected with regard to the intended route of administration and standard pharmaceutical practice. The excipient and/or carrier must be "acceptable" in the sense of being compatible with the other ingredients of the formulation and not deleterious to the recipient thereof. Acceptable excipients and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient and carrier can be selected with regard to the intended route of administration and standard pharmaceutical practice. Oral formulations readily accommodate additional mixtures, such as, e.g., milk, yogurt, and infant formula. Solid dosage forms for oral administration can also be used and can include, e.g., capsules, tablets, caplets, pills, troches, lozenges, powders, and granules. Non-limiting examples of suitable excipients include, e.g., diluents, buffering agents (e.g., sodium bicarbonate, infant formula, sterilized human milk, or other agents which allow bacteria to survive and grow [e.g., survive in the acidic environment of the stomach and to grow in the intestinal environment]), preservatives, stabilizers, binders, compaction agents, lubricants, dispersion enhancers, disintegration agents, antioxidants, flavoring agents, sweeteners, and coloring agents. Additional specific examples of suitable carriers and/or excipients include, e.g., vegetable cellulose, vegetable stearic acid, vegetable magnesium stearate, and/or silica. Those of relevant skill in the art are well able to prepare suitable solutions.

In one embodiment of any of the compositions of the invention, the composition is formulated for delivery by a route selected from the group consisting of oral, rectal, mucosal, sublingual, and via naso/oro-gastric gavage. In one embodiment of any of the compositions of the invention, the composition is in a form of a liquid, foam, cream, spray, powder, or gel. In one embodiment of any of the compositions of the invention, the composition comprises a buffering agent (e.g., sodium bicarbonate, infant formula or sterilized human milk).

The bacteria-containing formulations of the invention may comprise one or more prebiotics and/or probiotics which promote growth and/or activity of the bacteria in the formulation.

Non-limiting examples of prebiotic agents useful in the methods and compositions of the present invention include galactose, β-N-Acetyl-α-glucosamine, pyroglutamtamic acid, arginine, serine, glycine, and any combinations thereof.

Methods for producing bacterial compositions of the invention may include three main processing steps, combined with one or more mixing steps. The steps are: organism banking, organism production, and preservation. For banking, the strains included in the bacterial compositions of the invention may be (1) isolated directly from a specimen or taken from a banked stock, (2) optionally cultured on a nutrient agar or broth that supports growth to generate viable biomass, and (3) the biomass optionally preserved in multiple aliquots in long-term storage. The bacterial suspension can be freeze-dried to a powder and titrated. After drying, the powder may be blended to an appropriate potency, and mixed with other cultures and/or a filler such as microcrystalline cellulose for consistency and ease of handling, and the bacterial composition formulated as provided herein.

Therapeutic Methods of the Invention

In one aspect, the invention provides a method for preventing weight gain or promoting weight loss in a subject in need thereof, said method comprising administering to the subject an effective amount of a probiotic or a prebiotic composition or a combination thereof, wherein said composition(s) (i) stimulates growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) stimulates growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In a related aspect, the invention provides a method for preventing and/or treating obesity and/or an associated condition (e.g., metabolic syndrome, diabetes mellitus, insulin-deficiency, insulin-resistance related disorders, glucose intolerance, non-alcoholic fatty liver, abnormal lipid metabolism, hypertension, or atherosclerosis) in a subject in need thereof, said method comprising administering to the subject an effective amount of a probiotic or a prebiotic composition or a combination thereof, wherein said composition(s) (i) stimulates growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) stimulates growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In another aspect, the invention provides a method for altering intestinal immune gene expression (e.g., increasing expression of RORγT, IL-17A, IL-17F, RegIIIγ, Relmβ, and/or Defβ) in a subject in need thereof, said method comprising administering to the subject an effective amount of a probiotic or a prebiotic composition or a combination thereof, wherein said composition(s) (i) stimulates growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) stimulates growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In a further aspect, the invention provides a method for increasing intestinal T cell immunity in a subject in need thereof, said method comprising administering to the subject an effective amount of a probiotic or a prebiotic composition or a combination thereof, wherein said composition(s) (i)

stimulates growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) stimulates growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In yet another aspect, the invention provides a method for preventing and/or treating a gastrointestinal disorder (e.g., inflammatory bowel disease (IBD), ulcerative colitis, Crohn's disease, celiac disease, irritable bowel syndrome (IBS), infectious gastroenteritis, non-infectious gastroenteritis, food allergy, gastrointestinal graft versus host disease, small intestinal cancer, colon cancer, pouchitis, intestinal failure, short bowel syndrome, and antibiotic-associated diarrhea) in a subject in need thereof, said method comprising administering to the subject an effective amount of a probiotic or a prebiotic composition or a combination thereof, wherein said composition(s) (i) stimulates growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) stimulates growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In a separate aspect, the invention provides a method for promoting weight gain in a subject in need thereof, said method comprising administering to the subject an effective amount of a compound or composition, wherein said compound or composition (i) inhibits growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) inhibits growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In another aspect, the invention provides a method for decreasing an intestinal inflammation in a subject in need thereof, said method comprising administering to the subject an effective amount of a compound or composition, wherein said compound or composition (i) inhibits growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) inhibits growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In another aspect, the invention provides a method for decreasing an intestinal T cell immune response and/or altering intestinal immune gene expression (e.g., decreasing expression of RORγT, IL-17A, IL-17F, RegIIIγ, Relmβ, and/or Defβ) in a subject in need thereof, said method comprising administering to the subject an effective amount of a compound or composition, wherein said compound or composition (i) inhibits growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) inhibits growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

In a further aspect, the invention provides a method for preventing and/or treating an inflammatory or an autoimmune disorder (e.g., inflammatory bowel disease (IBD), asthma, celiac disease, eczema, allergic rhinitis, type 1 diabetes, systemic lupus erythematosis, rheumatoid arthritis, scleroderma, sarcoidosis, thyroiditis, multiple sclerosis, or myasthenia gravis) in a subject in need thereof, said method comprising administering to the subject an effective amount of a compound or composition, wherein said compound or composition (i) inhibits growth and/or activity of at least one strain of the bacterial genus *Ileibacterium* or a closely related OTU within the family Erysipelotrichaceae which has at least 90% sequence identity (and preferably at least 95% sequence identity, most preferably at least 99% sequence identity) to 16S rRNA of *Ileibacterium* spp. over its entire length or has at least 90% sequence identity (and preferably at least 95% sequence identity, most preferably at least 99% sequence identity) to any single V region of 16S rRNA of *Ileibacterium* spp. in the gastrointestinal (GI) microbiota of the subject and/or (ii) inhibits growth and/or activity of at least one strain of the bacterial genus *Dubosiella* or a closely related OTU within the family Erysipelotrichaceae which has at least 90% sequence identity (and preferably at least 95% sequence identity, most preferably at least 99% sequence identity) to 16S rRNA of *Dubosiella* spp. over its entire length or has at least 90% sequence identity (and preferably at least 95% sequence identity, most preferably at least 99% sequence identity) to any single V region of 16S rRNA of *Dubosiella* spp. in the gastrointestinal (GI) microbiota of the subject.

Non-limiting examples of inflammatory and autoimmune disorders treatable by the methods of the invention include autoimmune diseases, allergic diseases, infectious diseases, and rejection in organ transplantations. In one specific embodiment, said disease is selected from the group consisting of asthma, allergy, celiac disease, inflammatory bowel disease (IBD), ulcerative colitis, Crohn's disease, sprue, autoimmune arthritis, rheumatoid arthritis, multiple sclerosis, graft vs. host disease following bone marrow transplantation, osteoarthritis, juvenile chronic arthritis, psoriatic arthritis, reactive arthritis, spondyloarthropathy, systemic lupus erythematosus, insulin dependent diabetes mellitus, thyroiditis, asthma, psoriasis, scleroderma, atopic dermatitis, graft versus host disease, acute or chronic immune disease associated with organ transplantation, sarcoidosis, and atherosclerosis. In one embodiment, said disease is selected from the group consisting of inflammatory bowel disease (IBD), ulcerative colitis, Crohn's disease, irritable bowel syndrome (IBS), rheumatoid arthritis, Type I diabetes, multiple sclerosis (MS), amyotrophic lateral sclerosis (ALS), graft vs. host disease, osteoarthritis, juvenile chronic arthritis, Lyme arthritis, psoriatic arthritis, reactive arthritis, spondyloarthropathy, systemic lupus erythematosus (SLE), insulin dependent diabetes mellitus, thyroiditis, asthma, psoriasis, scleroderma, atopic dermatitis, graft versus host disease, acute or chronic immune disease associated with organ transplantation, sarcoidosis, atherosclerosis, disseminated intravascular coagulation, Kawasaki's disease, Grave's disease, nephrotic syndrome, Wegener's granulomatosis, Henoch-Schoenlejn purpurea, microscopic vasculitis of the kidneys, chronic active hepatitis, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (acute) respiratory distress syndrome, alopecia, alopecia areata, seronegative arthopathy, arthropathy, Reiter's disease, psoriatic arthropathy, chlamydia, atheromatous disease/arteriosclerosis, allergic colitis, atopic allergy, food allergies such as peanut allergy, tree nut allergy, egg allergy, milk allergy, soy allergy, wheat allergy, seafood allergy, shellfish allergy, or sesame seed allergy, autoimmune bullous disease, pemphigus vulgaris, pemphigus foliaceus, pemphigoid, linear IgA disease, autoimmune haemolytic anaemia, Coombs positive haemolytic anaemia, juvenile pernicious anaemia, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, idiopathic pulmonary fibrosis, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasculitis of the kidneys, discoid lupus, erythematosus, male infertility idiopathic or NOS, sperm autoimmunity, multiple sclerosis (all subtypes), insulindependent diabetes mellitus, sympathetic ophthalmia, pulmonary hypertension secondary to connective tissue disease, Goodpasture's syndrome, pulmonary manifestation of polyarteritis nodosa, acute rheumatio fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, allergic rhinitis (pollen allergies), anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, and eosinophilic gastroenteritis, diarrhea, colon cancer, cystic fibrosis, celiac disease, Type 2 diabetes, and autism-related immunopathologies.

In one embodiment of any of the above methods of the invention, the bacterial inoculum is administered in a therapeutically effective amount. The dosages of the microbiota inoculum and/or probiotic composition administered in the methods of the invention will vary widely, depending upon the subject's physical parameters, the frequency of administration, the manner of administration, the clearance rate, and the like. The initial dose may be larger, and might be followed by smaller maintenance doses. The dose may be administered as infrequently as weekly or biweekly, or fractionated into smaller doses and administered daily, semiweekly, etc., to maintain an effective dosage level. It is contemplated that a variety of doses will be effective to achieve colonization, e.g. $10^6$, $10^7$, $10^8$, $10^9$, and $10^{10}$ CFU for example, can be administered in a single dose. Lower doses can also be effective, e.g., $10^4$, and $10^5$ CFU.

In one embodiment of any of the above methods of the invention, the bacterial inoculum is administered to the subject by a route selected from the group consisting of oral, rectal (e.g., by enema), mucosal, sublingual, and via naso/oro-gastric gavage.

In one embodiment of any of the above methods of the invention, the bacterial inoculum is delivered to the subject in a form of a liquid, foam, cream, spray, powder, or gel. In one embodiment of any of the above methods of the invention, the bacterial inoculum is delivered to the subject in a form of a composition which comprises (i) a carrier and/or excipient and/or (ii) one or more prebiotic agents which stimulate growth and/or activity of one or more bacteria present in the composition. In one specific embodiment, said composition comprises an excipient or a carrier that optimizes the seeding of the transferred microbiota.

In one embodiment of any of the above methods, the method further comprises monitoring the subject's microbiota after the administration of the bacterial inoculum by: (a) determining a relative abundance of one or more bacterial taxa in a GI microbiota sample obtained from the subject (e.g., isolated from feces, intestines, etc.), and (b) comparing the relative abundance(s) determined in step (a) to (i) a predetermined standard value or (ii) to the abundance(s) of the same taxa in a control subject (e.g., a healthy subject) or (iii) to the average value of abundances of the same taxa in several control subjects. Non-limiting examples of the methods which can be used for determining the relative abundance of the bacterial taxa include, e.g., quantitative polymerase chain reaction (qPCR), sequencing of bacterial 16S rRNA, shotgun metagenome sequencing, and metabolomics. In one specific embodiment, the method involves determining a relative abundance of *Ileibacterium* valens and/or *Dubosiella newyorkensis*.

In one embodiment of any of the above methods involving administration of a probiotic composition, the probiotic composition is administered conjointly with a prebiotic which stimulates growth and/or activity of bacteria contained in the probiotic composition. Non-limiting examples of useful prebiotics include, e.g., galactose, β-N-Acetyl-α-glucosamine, pyroglutamtamic acid, arginine, serine, glycine, fructooligosaccharides (FOS), galactooligosaccharides (GOS), human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, arabinose, maltose, lactose, sucrose, cellobiose, amino acids, alcohols, resistant starch (RS), and any combinations thereof. In one specific embodiment, the probiotic and prebiotic are administered in one composition, or simultaneously as two separate compositions, or sequentially.

The probiotic composition useful in any of the above methods can comprise, without limitation, e.g., live bacterial cells, conditionally lethal bacterial cells, inactivated bacterial cells, killed bacterial cells, spores (e.g., germination-competent spores), recombinant carrier strains, cell extract, and bacterially-derived products (natural or synthetic bacterially-derived products such as, e.g., bacterial antigens or bacterial metabolic products).

In one embodiment of any of the above methods involving administration of a probiotic composition, said probiotic composition comprises (i) a carrier and/or excipient and/or (ii) one or more prebiotic agents which stimulate growth and/or activity of one or more bacteria present in the composition. In one specific embodiment, the probiotic composition comprises an excipient or a carrier that optimizes the seeding of one or more bacterial strains contained in said probiotic composition.

In one embodiment of any of the above methods involving administration of a probiotic composition, said probiotic composition is reconstituted from a lyophilized preparation. In one embodiment of any of the above methods involving administration of a probiotic composition, said probiotic composition comprises a buffering agent to adjust pH.

In one embodiment of any of the above methods involving administration of a probiotic composition, said probiotic composition comprises (i) a carrier and/or excipient and/or (ii) one or more prebiotic agents which stimulate growth and/or activity of one or more bacteria present in the composition. In one specific embodiment, the probiotic composition comprises an excipient or a carrier that optimizes the seeding of one or more bacterial strains contained in said probiotic composition.

In one embodiment of any of the above methods involving administration of a probiotic composition, the probiotic composition is delivered to the mouth, nose, and/or skin of the subject. In one embodiment, the probiotic composition is administered to the subject by a route selected from the group consisting of oral, topical, rectal (e.g., by enema), mucosal, sublingual, nasal, and via naso/oro-gastric gavage. In one embodiment, the probiotic composition is delivered to the subject in a form of a liquid, foam, cream, spray, powder, or gel. In one embodiment, the probiotic composition comprises a buffering agent (e.g., sodium bicarbonate, infant formula or sterilized human milk, or other agents which allow bacteria to survive and grow [e.g., survive in the acidic environment of the stomach and to grow in the intestinal environment]), along with preservatives, stabilizers, binders, compaction agents, lubricants, dispersion enhancers, disintegration agents, antioxidants, flavoring agents, sweeteners, and coloring agents.

In one embodiment of any of the above methods involving administration of a probiotic composition, the probiotic composition is administered conjointly with a prebiotic which stimulates growth and/or activity of bacteria contained in the probiotic composition. Non-limiting examples of useful prebiotics include, e.g., fructooligosaccharides (FOS), galactooligosaccharides (GOS), human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, arabinose, maltose, lactose, sucrose, cellobiose, amino acids, alcohols, resistant starch (RS), and any mixtures thereof. In one specific embodiment, the prebiotic is derived from microorganisms that show stimulation by human milk components. In one specific embodiment, the probiotic and prebiotic are administered in one composition, or simultaneously as two separate compositions, or sequentially.

It is also contemplated that when used to treat various diseases/disorders, the compositions and methods of the present invention can be utilized with other therapeutic methods/agents suitable for the same or similar diseases/disorders. Such other therapeutic methods/agents can be co-administered (simultaneously or sequentially) to generate additive or synergistic effects. Suitable therapeutically effective dosages for each agent may be lowered due to the additive action or synergy.

In one embodiment of any of the above methods of the invention, the method further comprises administering to the subject one or more additional compounds selected from the group consisting of immuno-suppresives, biologicals, probiotics, prebiotics, and cytokines (e.g., IFN or IL-22).

As a non-limiting example, the invention can be combined with other therapies that block inflammation (e.g., via blockage of ILL INFα/β, IL6, TNF, IL23, etc.).

The methods and compositions of the invention can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41BB, OX40, etc.). The methods of the invention can be also combined with other treatments that possess the ability to modulate NKT function or stability, including but not limited to CD1d, CD1d-fusion proteins, CD dimers or larger polymers of CD either unloaded or loaded with antigens, CD1d-chimeric antigen receptors (CD1d-CAR), or any other of the five known CD1 isomers existing in humans (CD1a, CD1b, CD1c, CD1e).

Non-limiting examples of additional pharmaceutically active compounds useful for treatment of obesity, metabolic syndrome, insulin-deficiency or insulin-resistance related disorders, glucose intolerance, diabetes mellitus, non-alcoholic fatty liver, abnormal lipid metabolism, atherosclerosis, and related disorders include anti-inflammatory agents, antioxidants, antiarrhythmics, cytokines, analgesics, vasodilators, antihypertensive agents including beta-blockers, angiotensin converting enzyme inhibitors (ACE inhibitors), and calcium channel blockers, inhibitors of cholesterol synthesis, cholesterol binding agents, antithrombotic agents, central modulators of appetite, and diabetes drugs. Examples of inhibitors of cholesterol synthesis or absorption which are useful in the combination therapies of the present invention include Hmg-CoA reductase inhibitors and their bio-active metabolites, such as, e.g., simvastatin, lovastatin, pravastatin, compactin, fluvastatin, dalvastatin, atorvastatin, HR-780, GR-95030, CI-981, BMY 22089, and BMY 22566. See, e.g., U.S. Pat. Nos. 4,346,227; 4,444,784; 4,857,522; 5,190,970; 5,316,765, and 5,461,039; PCT Publ. No. WO84/02131; GB Pat. No. 2,202,846. As used in the methods or compositions of the present invention, any one or several of the Hmg-CoA reductase inhibitor compounds may be mixed with L-arginine or a substrate precursor to endogenous nitric oxide, as described in U.S. Pat. Nos. 6,425,881 and 6,239,172, and 5,968,983, to provide a therapeutically effective mixture for use in conjunction with probiotics and/or prebiotics of the present invention.

Non-limiting examples of diabetes drugs useful in the combination therapies of the present invention include insulin, proinsulin, insulin analogs, activin, glucagon, somatostatin, amylin, actos (pioglitazone), amaryl (glimepiride), glipizide, avandia (rosiglitazone), glucophage, glucotrol, glucovance (a combination of glyburide and metformin), and the like. See, e.g., U.S. Pat. No. 6,610,272. The term "insulin" encompasses natural extracted human insulin, recombinantly produced human insulin, insulin extracted from bovine and/or porcine sources, recombinantly produced porcine and bovine insulin and mixtures of any of these insulin products. In accordance with the present invention, administering probiotics and/or prebiotics of the present invention in combination with insulin is expected to lower the dose of insulin required to manage the diabetic patient, while also alleviating the symptoms of metabolic syndrome.

Additional methods include methods of evaluating the microbiota population in a subject or diagnosing an abnormal microbiota development. Methods include monitoring the subject's microbiota after the administration of the microbiota inoculum or probiotic by: (a) determining a relative abundance of one or more bacterial taxa in a microbiota sample obtained from the subject, and (b) comparing the relative abundance(s) determined in step (a) to (i) a predetermined standard value or (ii) to the abundance(s) of the same taxa in a control subject or (iii) to the average value of abundances of the same taxa in several control subjects. The subject's sample may be isolated from feces, skin, intestines, intestinal mucosa, oral mucosa, conjunctive mucosa, or nasal mucosa. It may be compared to a control subject.

The determination of relative abundance of the taxa may involve, for example, a method selected from the group consisting of quantitative polymerase chain reaction (qPCR), sequencing of bacterial 16S rRNA, shotgun metagenome sequencing, and metabolomic analysis.

In accordance with the present invention there may be numerous tools and techniques within the skill of the art, such as those commonly used in molecular biology, pharmacology, and microbiology. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

Non-limiting examples of bacteria-containing formulations useful in the methods of the present invention include oral capsules and saline suspensions for use in feeding tubes, transmission via nasogastric tube, or enema. If live bacteria are used, the carrier should preferably contain an ingredient that promotes viability of the bacteria during storage. The formulation can include added ingredients to improve palatability, improve shelf-life, impart nutritional benefits, and the like. If a reproducible and measured dose is desired, the bacteria can be administered by a rumen cannula. In certain embodiments, the bacteria-containing formulation used in the methods of the invention further comprises a buffering agent. Examples of useful buffering agents include saline, sodium bicarbonate, milk, yogurt, infant formula, and other dairy products.

Oral delivery may also include the use of nanoparticles that can be targeted, e.g., to the GI tract of the subject, such as those described in Yun et al., Adv Drug Deliv Rev. 2013, 65(6):822-832 (e.g., mucoadhesive nanoparticles, negatively charged carboxylate- or sulfate-modified particles, etc.). Non-limiting examples of other methods of targeting delivery of compositions to the GI tract are discussed in U.S. Pat. Appl. Pub. No. 2013/0149339 and references cited therein (e.g., pH sensitive compositions [such as, e.g., enteric polymers which release their contents when the pH becomes alkaline after the enteric polymers pass through the stomach], compositions for delaying the release [e.g., compositions which use hydrogel as a shell or a material which coats the active substance with, e.g., in vivo degradable polymers, gradually hydrolyzable polymers, gradually water-soluble polymers, and/or enzyme degradable polymers], bioadhesive compositions which specifically adhere to the colonic mucosal membrane, compositions into which a protease inhibitor is incorporated, a carrier system being specifically decomposed by an enzyme present in the colon).

For oral administration, the active ingredient(s) can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Diagnostic Methods of the Invention

In one embodiment, the present invention provides a method for diagnosing predisposition to obesity and/or associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis) in a subject, said method comprising (a) determining the level of (i) at least one strain of the bacterial genus *Ileibacterium* or a closely related OTU within the family Erysipelotrichaceae which has at least 90% (or at least 95%, or at least 99%) sequence identity to 16S rRNA of *Ileibacterium* spp. over its entire length or has at least 90% (or at least 95%, or at least 99%) sequence identity to any single V region of 16S rRNA of *Ileibacterium* spp. in the gastrointestinal (GI) microbiota of the subject and/or (ii) at least one strain of the bacterial genus *Dubosiella* or a closely related OTU within the family Erysipelotrichaceae which has at least 90% (or at least 95%, or at least 99%) sequence identity to 16S rRNA of *Dubosiella* spp. over its entire length or has at least 90% (or at least 95%, or at least 99%) sequence identity to any single V region of 16S rRNA of *Dubosiella* spp. in the gastrointestinal (GI) microbiota of the subject (e.g., cecal, ileal, colonic, or fecal microbiota), and (b) comparing the level determined in step (a) to the level of the same bacteria in the gastrointestinal microbiota of healthy controls, and (c) identifying that the subject is predisposed to obesity and/or associated conditions wherein the level of at least one of the strains measured in step (a) is lower (e.g., at least 50% lower, preferably at least 70% lower) than in healthy controls.

In another embodiment, the present invention provides a method for diagnosing predisposition to gastrointestinal and/or inflammatory disorders (e.g., inflammatory bowel disease (IBD), ulcerative colitis, Crohn's disease, celiac disease, irritable bowel syndrome (IBS), infectious gastroenteritis, non-infectious gastroenteritis, food allergy, gastrointestinal graft versus host disease, small intestinal cancer, colon cancer, pouchitis, intestinal failure, short bowel syndrome, and antibiotics-associated diarrhea) in a subject, said method comprising (a) determining the level of (i) at least one strain of the bacterial genus *Ileibacterium* or a closely related OTU within the family Erysipelotrichaceae which has at least 90% (or at least 95%, or at least 99%) sequence identity to 16S rRNA of *Ileibacterium* spp. over its entire length or has at least 90% (or at least 95%, or at least 99%) sequence identity to any single V region of 16S rRNA of *Ileibacterium* spp. in the gastrointestinal (GI) microbiota of the subject and/or (ii) at least one strain of the bacterial genus *Dubosiella* or a closely related OTU within the family Erysipelotrichaceae which has at least 90% (or at least 95%, or at least 99%) sequence identity to 16S rRNA of *Dubosiella* spp. over its entire length or has at least 90% (or at least 95%, or at least 99%) sequence identity to any single V region of 16S rRNA of *Dubosiella* spp. in the gastrointestinal (GI) microbiota of the subject (e.g., cecal, ileal, colonic, or fecal microbiota), and (b) comparing the level determined in step (a) to the level of the same bacteria in the intestinal microbiota of healthy controls, and (c) identifying that the subject is predisposed to gastrointestinal and/or inflammatory disorders wherein the level of at least one of the strains measured in step (a) is higher (e.g., at least 50% higher, preferably at least 70% higher) than in healthy controls.

Non-limiting examples of the methods which can be used for determining the relative abundance of the bacterial strains include, e.g., quantitative polymerase chain reaction (qPCR), sequencing of bacterial 16S rRNA, shotgun metagenome sequencing, and metabolomics.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Figure 1C:
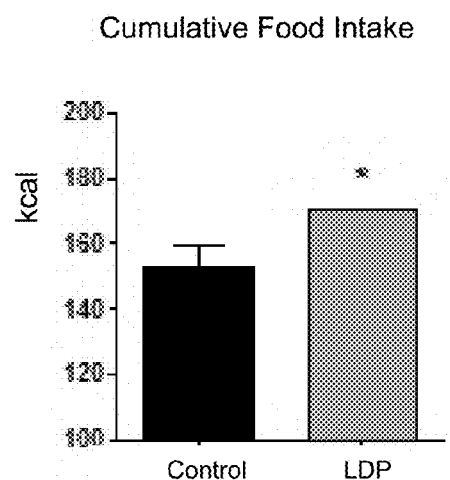
FIG. 1C: Cumulative food intake for female mice over 12 days during weeks 6 to 8 (n=4 mice/group in metabolic cages).
Figure 1B:
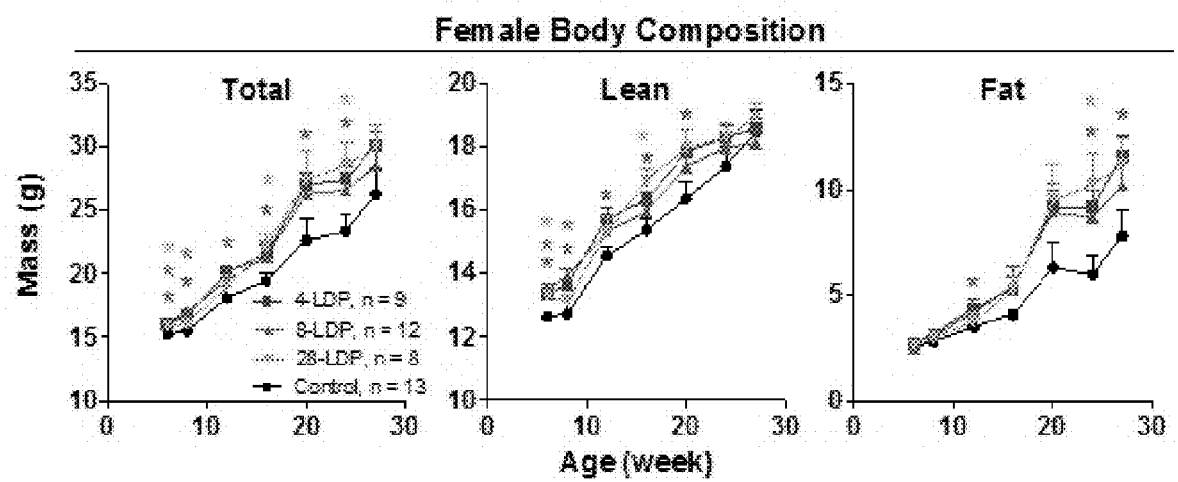
FIG. 1B: Total, lean, and fat mass in female mice, measured by DEXA scanning. *$p<0.05$ significant difference at a single time point measured by t-test. 4-, 8-, and 28-LDP mice had significantly increased rates of total and fat mass accumulation from 6-20 weeks of age.

Example 1. Characterizing Metabolic and Immunologic Changes in Antibiotic-Induced Obesity To examine the effect of early-life microbiota disruption on adiposity, low-dose penicillin (LDP) was administered to C57BL6J mice at birth, or not (control), and LDP mice were maintained on antibiotics for 4, 8, or 28 weeks of life. Regardless of length of exposure, all groups of LDP mice had significant elevations of total and fat mass, indicating that 4 weeks of antibiotic exposure was sufficient for lasting changes[15] (FIG. 1A-1B). Compared to controls, following switch to a high fat diet (HFD, Research Diets diet-induced obesity diet # D12451), female LDP mice had significantly elevated caloric intake (FIG. 1C) and significantly faster total and fat mass accumulation rates from 6-20 weeks of age. Later in life (weeks 20-28), all three LDP groups showed significantly slower rates in lean mass growth compared to controls, indicating catch-up by the control mice.

Figure 1D:
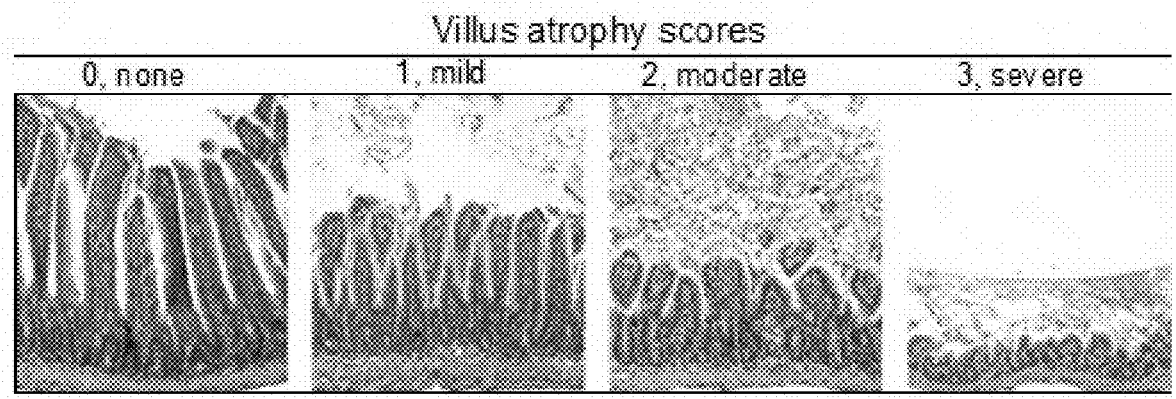
FIG. 1D: Histopathology: representative H&E-stained ileal sections with villus atrophy scores 0-3.
Figure 1E:
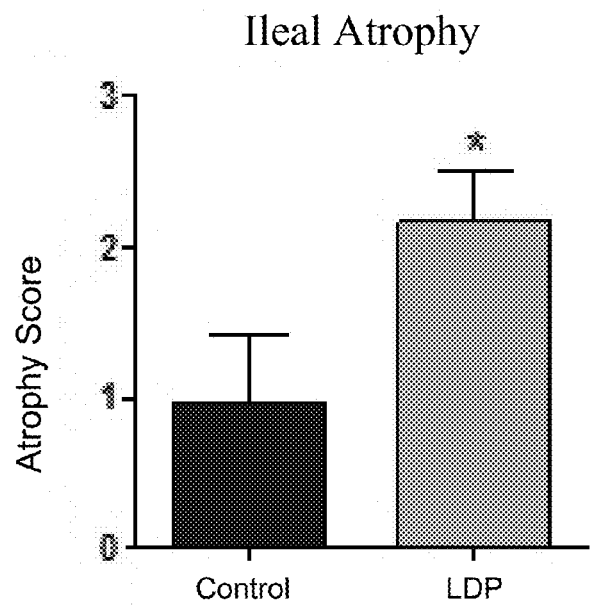
FIG. 1E: Mean±SEM ileal atrophy score in male control and LDP mice (n=5 each), *$p<0.05$ Mann-Whitney U for panels FIG. 1C & FIG. 1E.
Figure 1F:
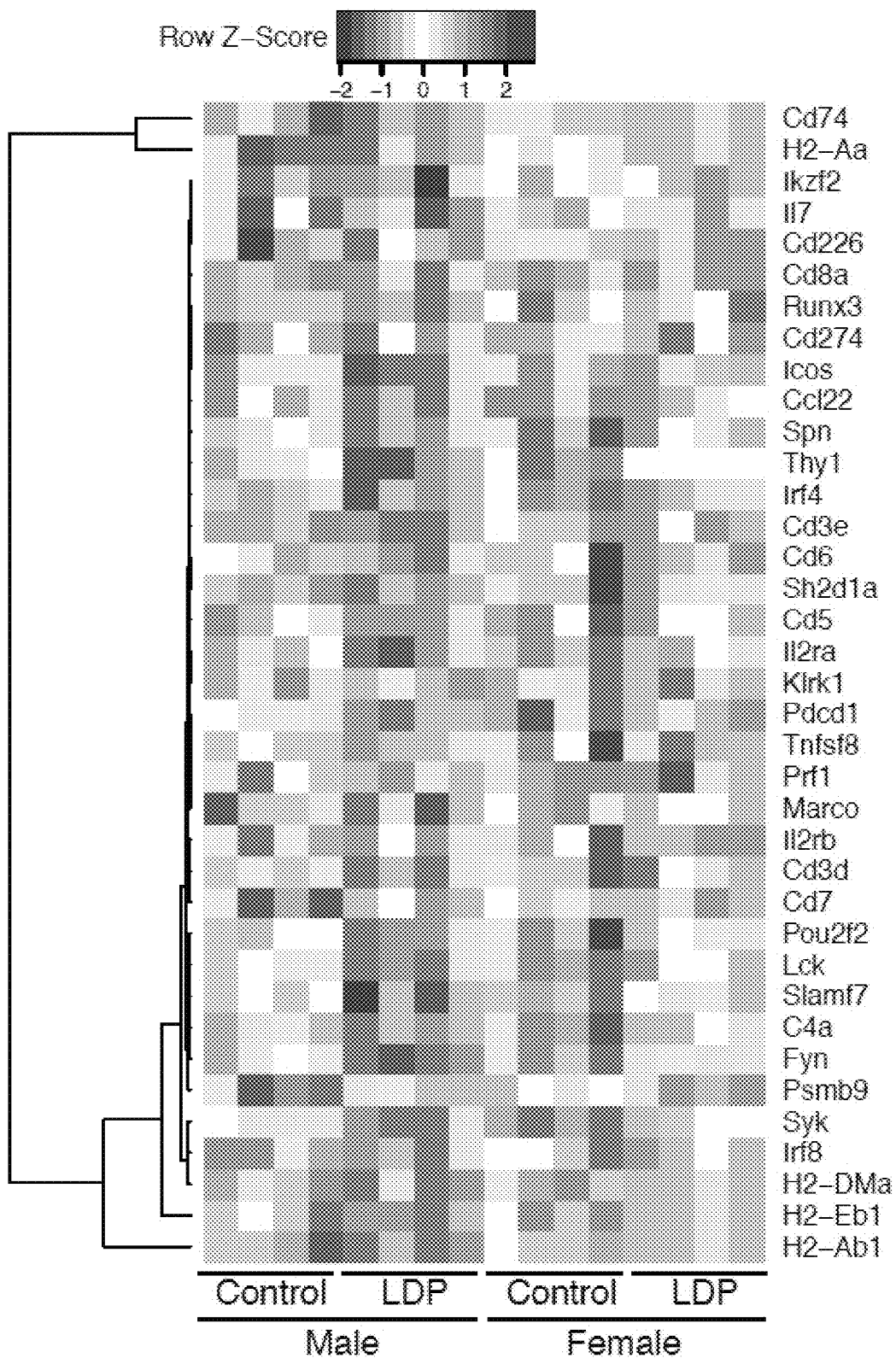
FIG. 1F: Expression of ileal genes that are significantly altered by LDP in both male and female mice (n=4 each) at 8 weeks of age, measured by the Nanostring Mouse Immunology Kit, genes shown $p<0.05$, t-test. Ileal expression of transcription factors (FIG. 1G-FIG. 1J) and cytokines (FIG. 1K-FIG. 1N) representative of four T-helper cell lineages, and expression of antimicrobial peptides (FIG. 1O-FIG. 1P) measured by qPCR; p-values shown for t-tests for 8-week male and female mice, n=4 each.
Figure 1G:
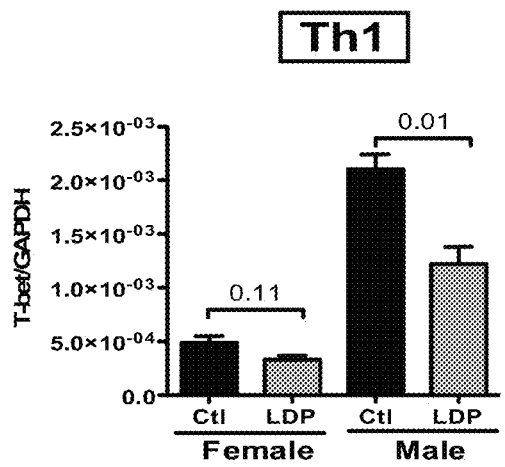
Figure 1H:
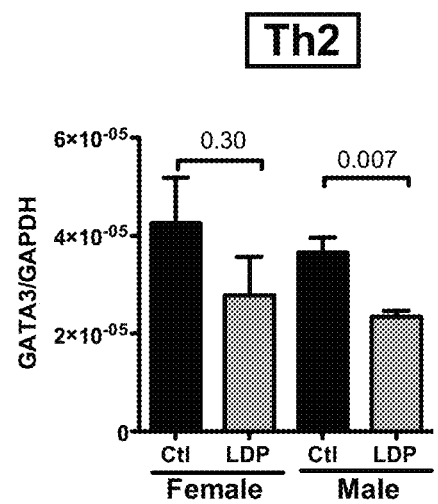
Figure 1I:
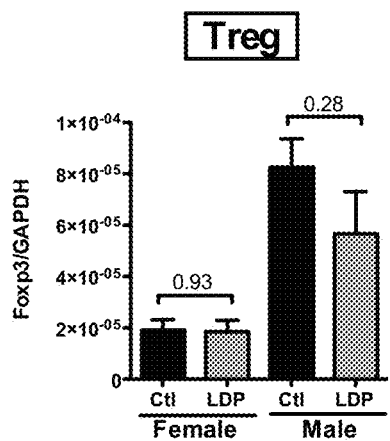
Figure 1J:
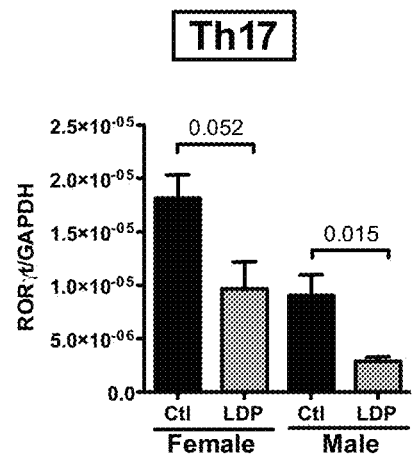
Figure 1K:
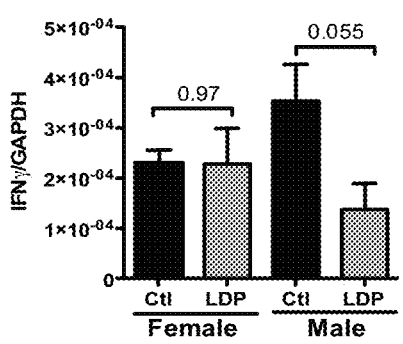
Figure 1L:
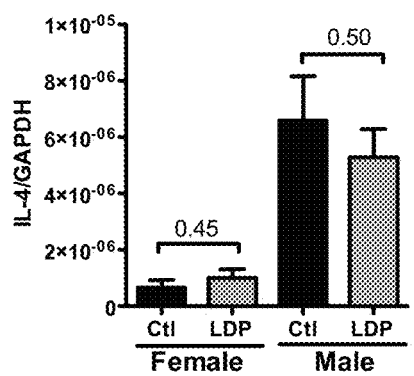
Figure 1M:
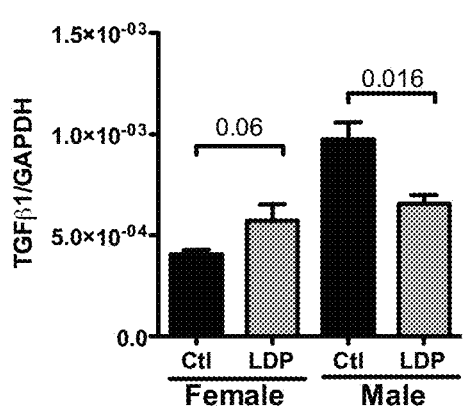
Figure 1N:
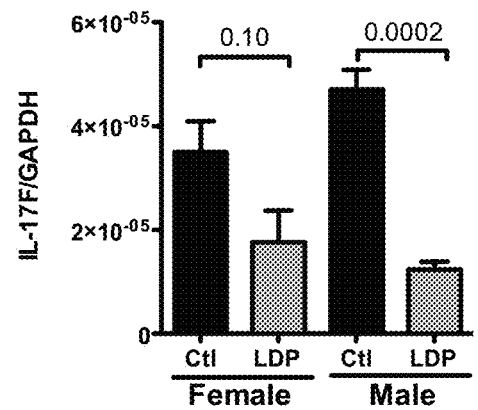

Disruption of defenses at the intestinal interface has been implicated in obesity (Cani et al., 2008; Henao-Mejia et al., 2012; Vijay-Kumar et al., 2010). By age 4 weeks, LDP induced substantial histopathologic effects in ileal tissues, notably shortened villi (FIG. 1D-1E), consistent with changed ileal architecture in LDP-mediated livestock growth promotion (Gaskins et al., 2002; Visek, 1978). To further investigate changes in the intestine, total RNA was extracted by the RNeasy Mini Kit (Qiagen, Valencia Calif.). For microarrary analysis, expression profiling was performed using the Affymetrix Genechip Chip Mouse 430_2 system (Affymetrix, Santa Clara Calif.). The raw microarray data was normalized using the Robust Multi-Array (RMA) method (Irizarry, 2003). The Limma package in R was used to fit a linear model to the expression data using empirical Bayes moderated t-statistics (Smyth, 2004). Ileal gene expression was measured by the nCounter GX Mouse Immunology Kit (Nanostring Technologies, Seattle, Wash., USA). Transcriptional profiling analysis of intestinal tissue by microarray and subsequent validation by Nanostring analysis (Cox et al., Cell, 2014, 158(4):705-721) revealed that the ileal atrophy from LDP was associated with a general decreased expression of genes involved in intestinal immune responses, with numerous consistencies across gender (FIG. 1F). LDP decreased expression of genes related to several biologic functions, such as differentiation, activation, recruitment, and adhesion of immune cells, and functions specifically related to antigen-presenting cells, T-cells, B-cells, and phagocytic cells.

Figure 1O:
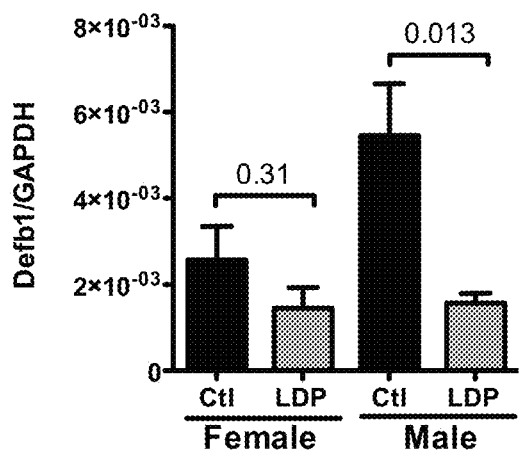
Figure 1P:
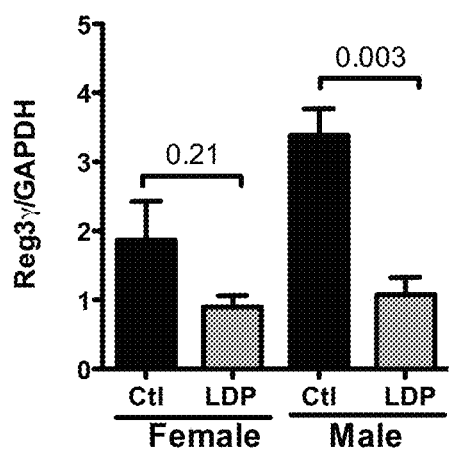
Figure 1Q:
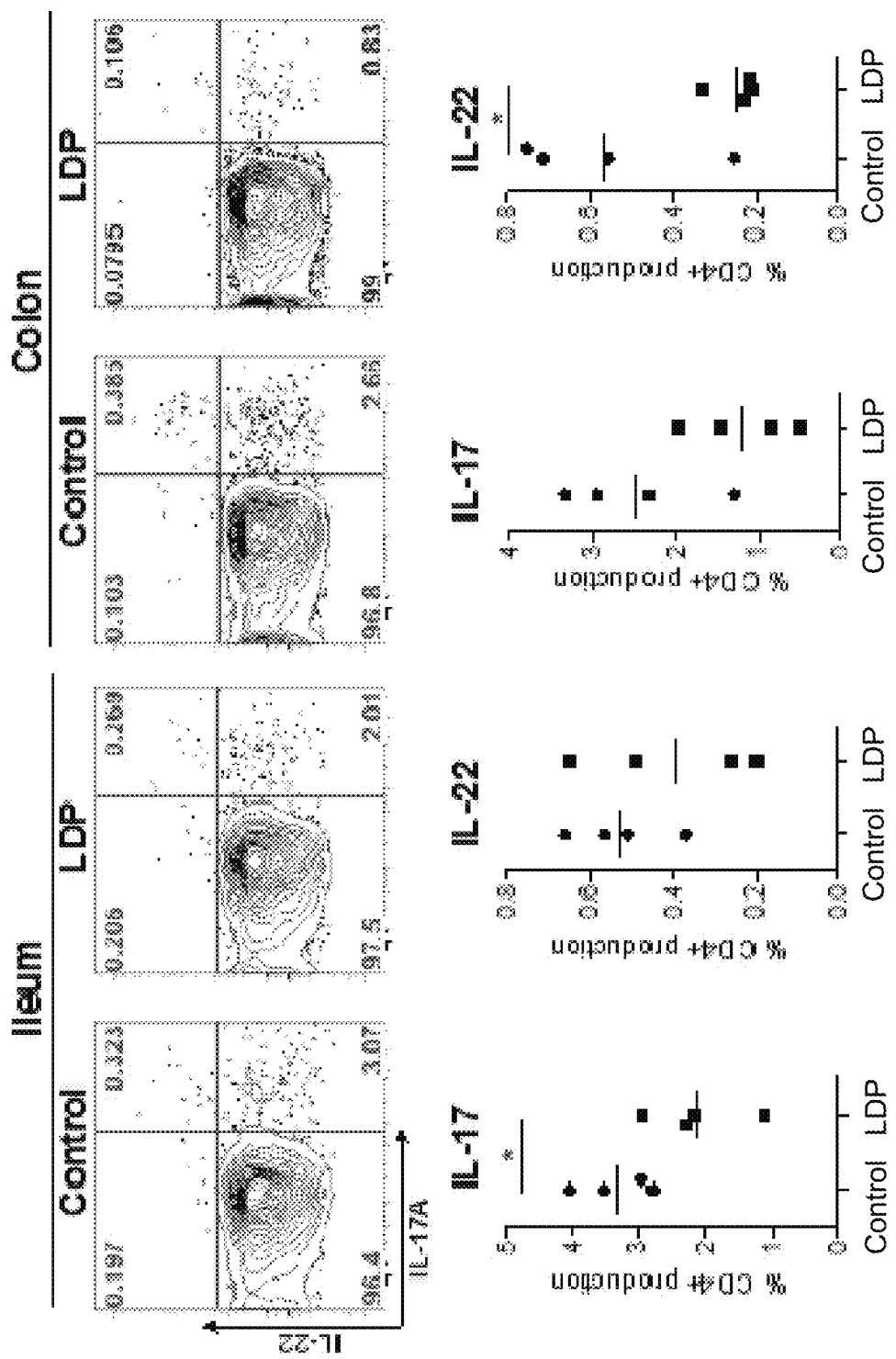

The gut microbiota influences the composition of CD4+ T cells within the intestinal mucosa (Hooper et al., 2012). LDP reduced expression of transcription factors and cytokines important for Th1 and Th17 cell differentiation and function (FIG. 1G-1N), with significant effects in males and consistent trends in females. Antimicrobial peptides β-defensin 1 (Defb1) and regenerating islet-derived protein 3 gamma (RegIIIγ) also were down-regulated by LDP (FIG. 1O-1P). To confirm the Th17 cell alterations, we performed flow cytometric analysis on lamina propria cells isolated from the ileum and colon in 8-week old male mice. These showed reduced CD4+IL-17- or IL-22-positive cell populations after LDP (FIG. 1Q). Taken together, these results indicate that intestinal immune responses are globally reduced after LDP.

Example 2. Characterizing Metabolic and Immunologic Changes in Microbe-Induced Obesity. LDP-Altered Microbiota are Sufficient to Induce Metabolic Changes While the above observations suggest that the change in the microbiota is driving the metabolic and immunologic effects, they also could reflect the influence of the administered LDP on development. To eliminate the direct effects of penicillin, cecal microbiota were transferred from 18-week old female control or LDP mice (n=3 each) (FIG. 2A) to 3-week old female germ-free Swiss-Webster mice (Taconic Farms). While the strains of murine microbiota donor and germ-free recipient were not the same, this approach has been used to test the causality of altered microbiota between differing mouse strains (Vijay-Kumar et al., 2010) and host species (humans and mice) (Ridaura et al., 2013). The LDP-microbiota recipients increased total mass and fat mass at a faster rate (rate differential=0.078 g/day total (p=0.01), 0.058 g/day fat (p=0.0012)) compared to controls; no changes were detected in lean mass (FIG. 2B). These findings indicate that the host metabolic changes are driven by the LDP-altered microbiota and are not dependent on direct antibiotic effects on the host.

Figure 2E:
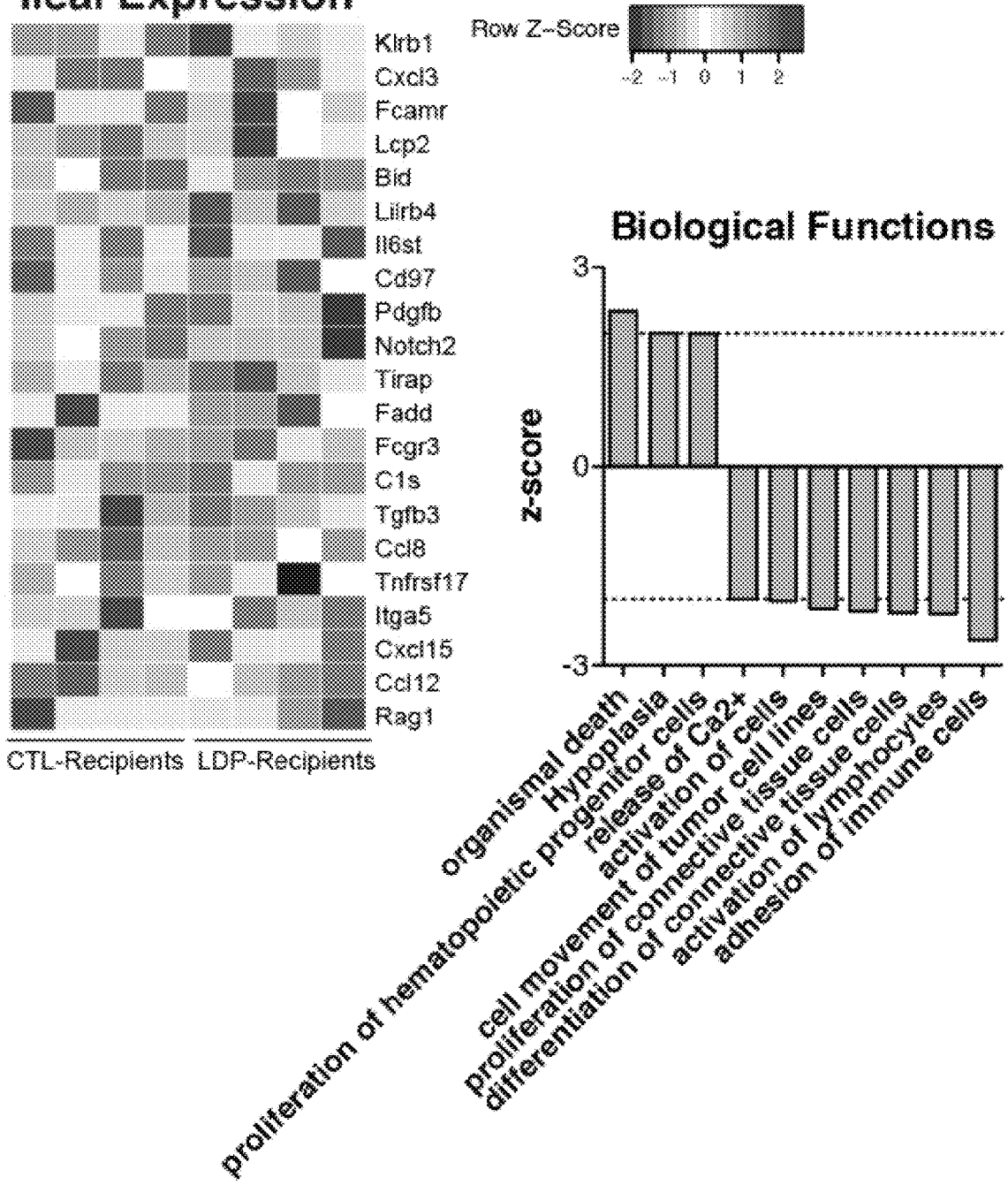

As hypothesized, the LDP microbiota donor mice had decreased ileal expression of genes involved in Th17 populations and antimicrobial peptides (FIG. 2C). At 8 weeks of age, the LDP-microbiota recipients showed similar trends to the donor mice (FIG. 2D). The LDP-altered microbiota also changed immunological gene expression compared to the recipients of the control microbiota (FIG. 2E), and these changes were related to predicted biological functions similarly altered in the 8-week old male and female mice directly exposed to LDP, including decreased differentiation, activation, adhesion, recruitment, and quantity of immune cells. These studies provide evidence that altered microbiota can mediate changes in intestinal immune gene expression and are consistent with the global reduction in intestinal immune responses observed in the LDP-exposed microbiota donors (FIG. 1F-1Q).

Example 3. Identifying Candidate Metabolically and Immunologically Interactive Microbiota The microbiota samples from the LDP microbiota donor mice and recipient mice were examined by sequencing the V4 region of the 16S rRNA gene using Golay-corrected barcoded primers based on the Universal bacterial/archaeal primers 515F and 806R, designed for the HiSeq2000 and MiSeq Illumina platform, as shown in Supplemental File of Caporaso et al., The ISME J., 2012, 6:1621-1624. In order to increase the number of taxa named at the genus level, the confidence threshold of the RDP classifier was set to 50%, as recommended for sequences of at least 250 bp in length, but substantially less stringent than the 80% confidence default threshold. This resulted in an increase of organisms named at the genus level, but included some misidentification of closely related genera. Based on this less stringent taxonomic assignment, the genus *Allobaculum* was identified as a taxon that was consistently reduced in the two experiments described above, as well as two other taxa recently described by the inventors (*Lactobacillus* and *Rikenellaceae*; Cox et al., Cell, 2014, 158(4): 705-721) (FIG. 3A-3B). The metabolic and physiologic associations were further investigated by performing a Spearman correlation between *Allobaculum* levels over time and eventual total mass, fat mass, and expression levels of markers of intestinal defense (FIG. 3C). There was a consistent negative correlation between total and fat mass, providing evidence that suggests that high levels of *Allobaculum* could inhibit obesity. There was a consistent positive correlation with RORγT, IL-17F, RegIIIγ, and Relmβ, indicating a relationship between *Allobaculum* and increasing intestinal defenses.

Example 4. Molecular Identification and Characterization of Novel *Allobaculum*-Like Organisms

*Allobaculum* spp are Gram positive anaerobic bacilli, originally isolated from the feces of a dog. *A. stercoricanis* is the type species of the genus (Greetham, 2004, Anaerobe). Its genome contains 2,052,877 bases and has a G+C content of 37.9%, with 1853 genes, 1748 of which are protein coding (JGI website at genome.jgi.doe.gov). In the inventors' prior work (Cox et al., Cell, 2014, 158(4):705-721), it was demonstrated that early life *Allobaculum* levels were reduced in response to low-dose penicillin across multiple independent experiments. In each case, it was also associated with the prevention of weight gain and obesity. Based on the potential for this organism to play a role in promoting metabolic health, the inventors sought to further examine *Allobaculum* populations in our study. Since only one species within the genus is described, a combination of molecular and culture techniques were used to investigate *Allobaculum*.

Figure 4A:
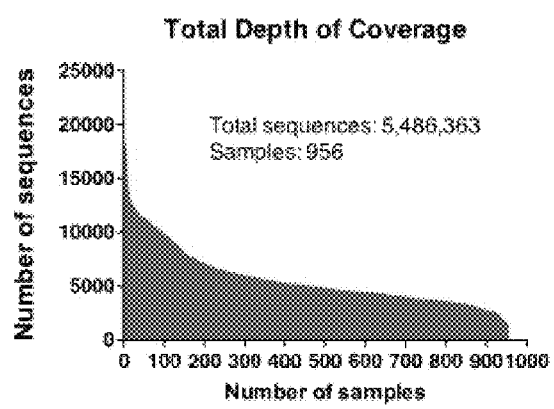
Figure 4B:
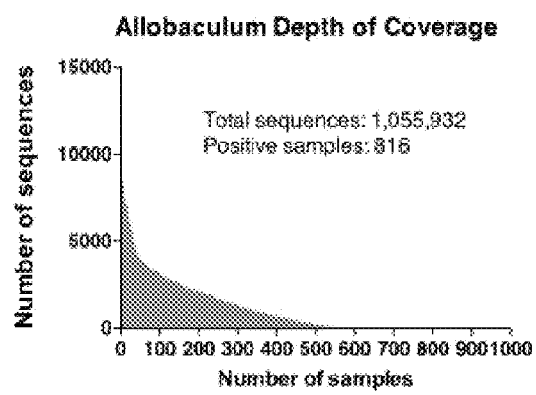
Figure 4C:
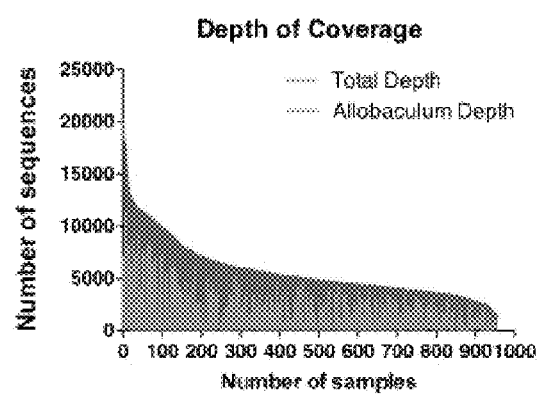
Figure 4D:
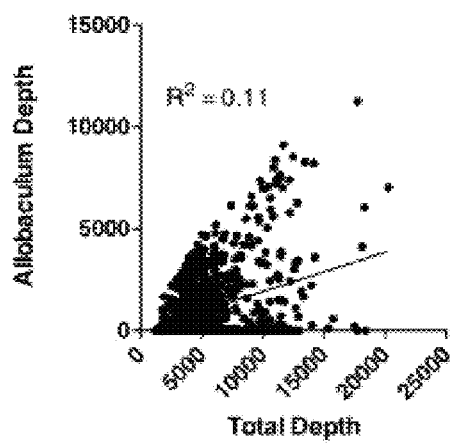

Of a total of 956 murine intestinal samples (fecal, cecal, ileal), with a total sequencing depth of 5,486,363 reads (FIG. 4A), the genus *Allobaculum* was detected in 816 (85.4%) samples, accounting for 1,055,932 reads (19.2%) (FIG. 4B). The levels of *Allobaculum* counts did not necessarily mirror the depth of coverage (FIG. 4C). The correlation value was low (R2=0.1, Pearson correlation) between total and *Allobaculum* sequences, however it was significant (p<0.0001) (FIG. 4D).

Figure 4E:
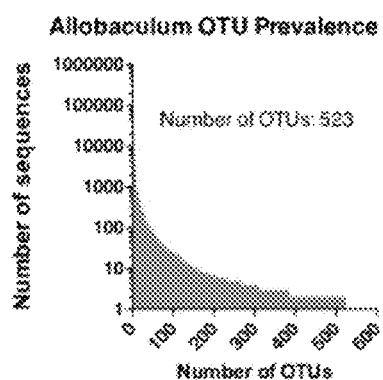
Figure 4F:
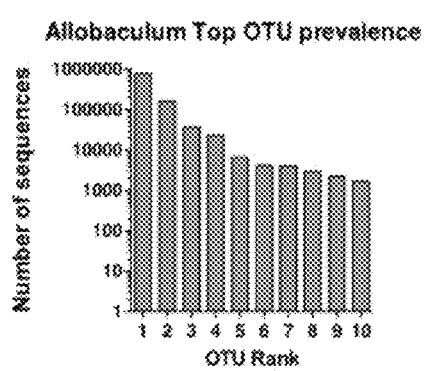
Figure 4G:
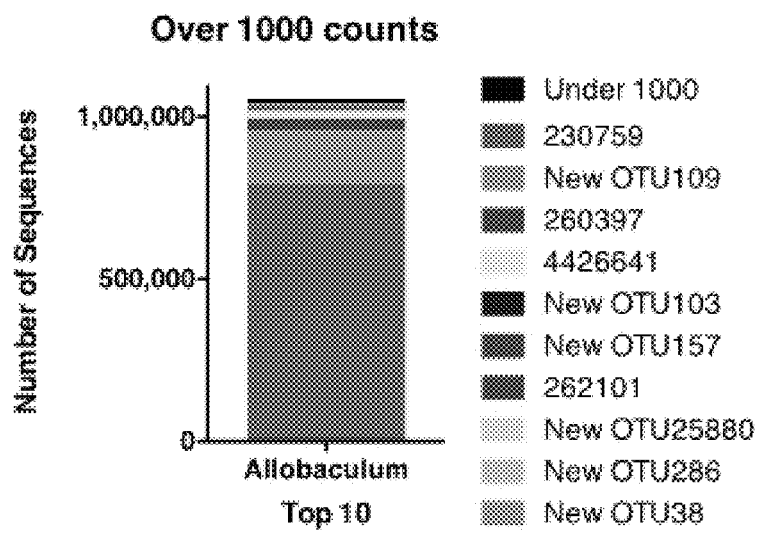
Figure 4H:
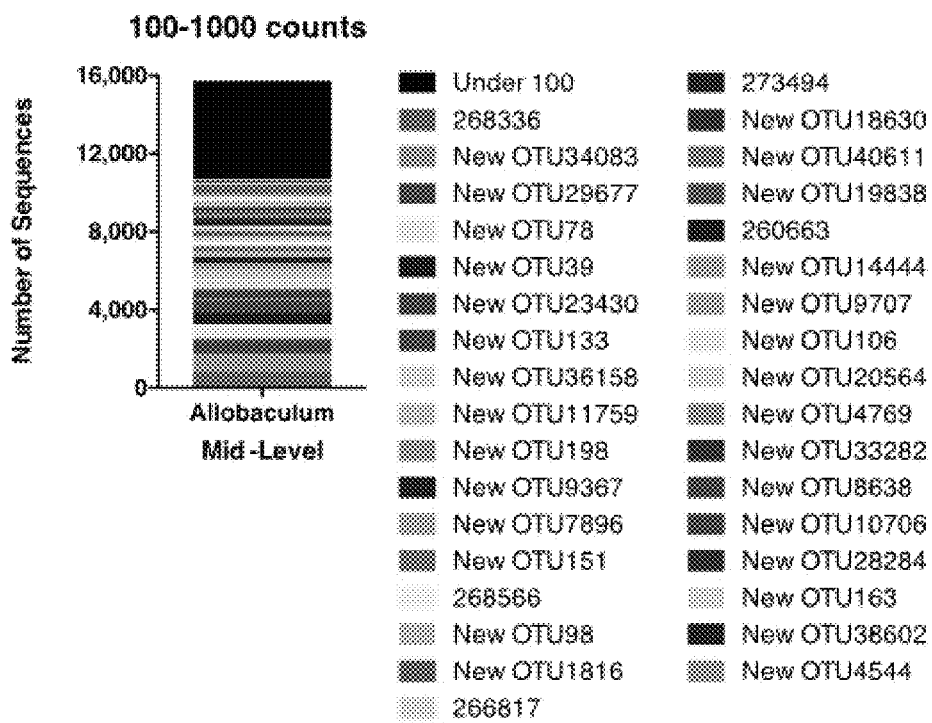

There were 523 different OTUs detected for *Allobaculum*, with 21 (4%) matching the 2013 May GreenGenes reference data base (DeSantis et al., 2006. Greengenes, a Chimera-Checked 16S rRNA Gene Database and Workbench Compatible with ARB. Appl Environ Microbiol., 72:5069-72) and 502 (96%) detected as new OTUs by de novo OTU picking. Of the 523 *Allobaculum* OTUs detected, there were a few dominant OTUs; only 10 (2%) OTUs had counts above 1,000 (FIG. 4E-4G). This indicates that within the population of mice in this study, few *Allobaculum* species contribute predominant populations. 34 (6%) OTUs had sequence counts between 100 and 1000 (FIG. 4H), and 479 OTUs had sequence counts below 100, which may represent sequencing noise.

Figure 5:
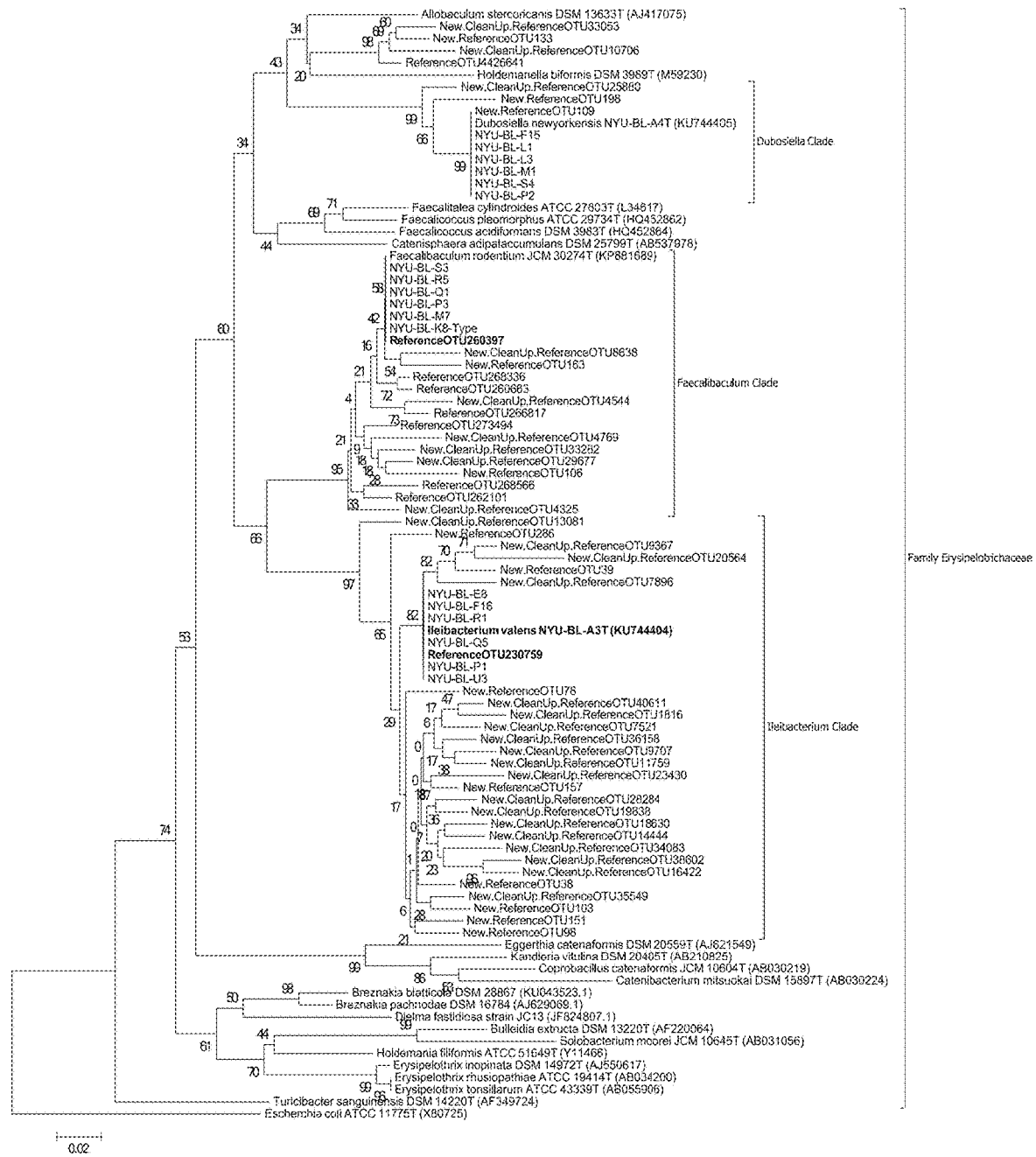
FIG. 5. Phylogenetic distribution of top 50 *Allobaculum* OTUs determined by high-throughput sequencing of the 16S rRNA gene V4 region. The phylogenetic tree is rooted on *Escherichia coli*, and also contains sequence representatives of members of the family Erysipelotrichaceae. The tree was constructed by the neighbor-joining method. Branch length corresponds to differences in sequence, and the numbers list the confidence level of each branch.
Figure 6:
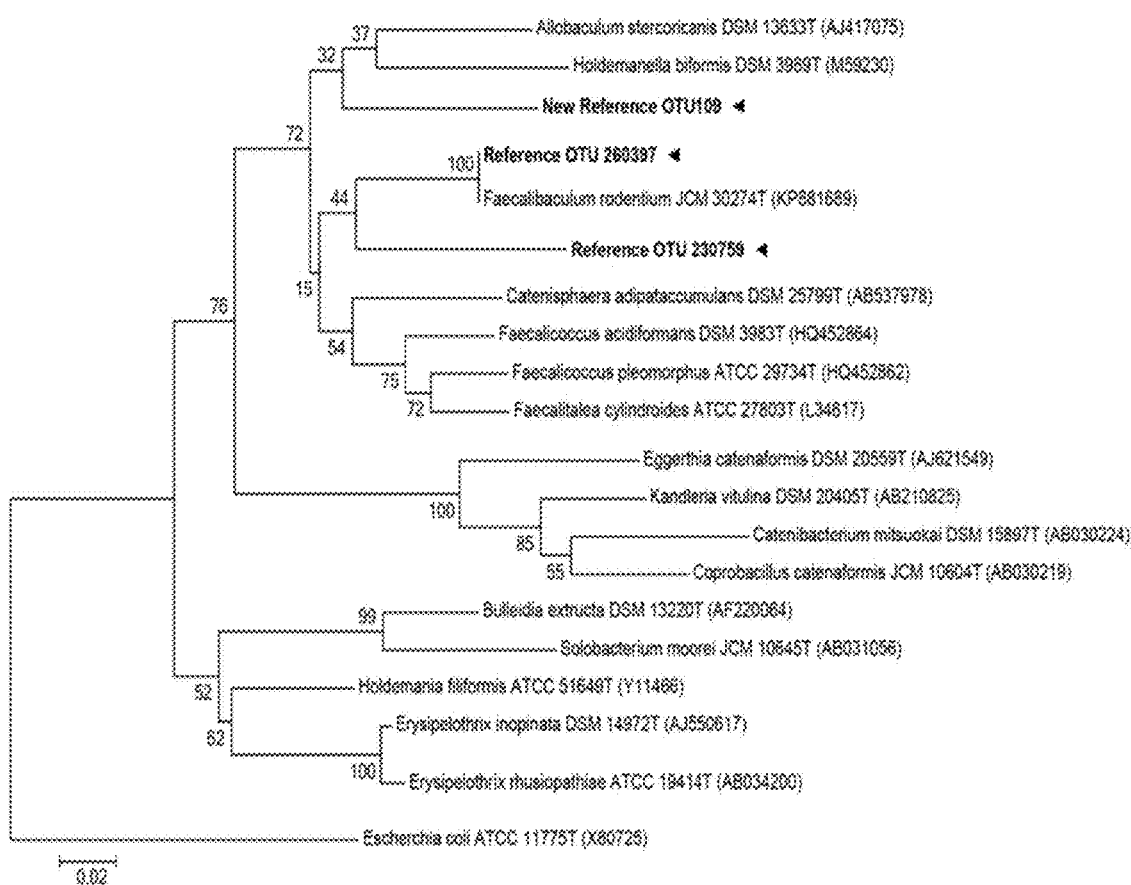
FIG. 6. Phylogenetic distribution of top 3 *Allobaculum* OTUs with reference Erysipelotrichaceae strains. The evolutionary history between the top three *Allobaculum* OTUs (triangles) and reference sequences from all genera in the family Erysipelotrichaceae (NCBI accession number listed in parentheses) was inferred using the Neighbor-Joining method. The percentages of replicate trees in which the associated taxa clustered together in the bootstrap test (1000 replicates) are shown next to the branches. The tree is drawn to scale; with branch lengths representing evolutionary distances in the units of the number of base substitutions per site computed using the Jukes-Cantor method. This tree indicates that the top two OTUs, Reference OTU 230759 and New Reference 1109 (OTU109), are substantially divergent from *Allobaculum stercoricanis*, and the Reference OTU 260397 is an identical match to *Faecalibaculum rodentium*.

That the predominant OTUs may be truly different strains, or the difference in OTU assignment could be due to either sequencing errors or variation in the OTU picking heuristic. Sequences were filtered at a Phred score of Q20, which corresponds to a 1% error. Over an amplicon of 253 base pairs, ≤3 errors could be expected. To examine the relatedness of the OTUs, a phylogenetic tree was constructed with 4 reference strains (*Allobaculum stercoricanis*, and near and distant bacterial taxa) all 523 *Allobaculum* OTUs (FIG. 5). Despite a large degree of sequence variation amongst *Allobaculum* OTU sequences, there appear to be 3 clades of *Allobaculum*, each represented by one of the three most highly abundant *Allobaculum* OTUs.

It was next investigated whether each of the three clades of *Allobaculum* OTUs identified by sequencing were consistent with a bona fide identification of *Allobaculum* genus. Sequences were obtained from each cultured genus within the family Erysipelotrichaceae, including *Allobaculum*, and a phylogenetic tree was constructed in order to investigate the taxonomic relationships. None of the three top *Allobaculum* OTUs were located on the same branch as *Allobaculum*, indicating substantially divergent relationships. Next, the percent identity was calculated (Table 1), and found that the top three OTUs were less than 90% identical to the reference sequence for *Allobaculum stercoricanis*, indicating that these OTUs were in fact different genera. The third most abundant OTU, Reference OTU260397, was 100% identical to *Faecalibaculum rodentium*, indicating that this sequence had been misclassified, likely because of the low stringency of the taxonomic assignment parameters and because that reference sequence was not in the Greengenes 16S database used to assign bacterial identities. In all, this data indicates that the metabolically and immunologically interactive OTUs we originally identified as *Allobaculum* were three different genera, all within the same family.

Example 5. Recovery of Cultured Isolates of Top 3 *Allobaculum*-Like OTUs, and Description of Two Novel Members of the Family Erysipelotrichaceae: *Ileibacterium* Valens Gen. Nov. Sp. Nov. And *Dubosiella newyorkensis*, Gen. Nov., Sp. Nov High-throughput sequencing technology has markedly accelerated research on microbes in complex ecosystems, including host-associated bacteria, collectively known as the microbiota, that have roles in shaping health and disease[16-18]. With untested potential microbe-host associations being identified on a regular basis, there is an increasing need to culture and characterize new bacterial taxa to further mechanistic research. The inventors' previous work (Cox et al., Cell, 2014, 158(4):705-721) identified *Allobaculum* within the family Erysipelotrichaceae, as a potentially beneficial organism, affecting both metabolism and immune responses[15]. Cultivation studies designed to isolate *Allobaculum* organism yielded 111 colonies that when screened via 16S rRNA sequencing, corresponded to three phylogenetically distinct clusters located in the family Erysipelotrichaceae. Two of the groups were most closely related to *Allobaculum stercoricanis* of all known taxa, but with 16S rRNA similarity values <90% while the third group was identical to the recently described *Faecalibaculum rodentium*[19], which also recovered from a laboratory mouse. Here, using isolates from our studies of microbe-induced obesity, two novel genera are described, and the phenotypic characteristics of additional strains of *Faecalibaculum rodentium*.

The family Erysipelotrichaceae was first described by Verbarg et al. to include a number of Gram-stain positive, slender or filamentous rods with a β-cross-linking type murein belonging to the genus Erysipelothrix[20]. In the 2009 edition of Bergey's Manual of Systematic Bacteriology, the family is placed within phylum Firmicutes and includes the genera *Allobaculum, Bulleidia, Catenibacterium, Coprobacillus, Holdemania, Solobacterium*, and *Turicibacter*[21], although novel families have been proposed for Coprobacillus and Turicibacter, based on 16S phylogeny[22]. Recently, *Catenisphaera adipataccumulans*[23] was described as a new genera phylogenetically placed within Erysipelotrichaceae, and *Faecalicoccus, Hodemanella* and *Faecalitalea* were created to encompass the misclassified *Streptococcus pleomorphus, Eubacterium biforme*, and *Eubacterium cylindroides*, respectively[24]. Recently, *Faecalibaculum rodentium* was described, after its isolation from the murine intestinal contents of a laboratory mouse[19], and was nearly identical (99.8-100% sequence similarity) to a third group of strains recovered in the present study. The present study expands our knowledge of the relatively understudied family Erysipelotrichaceae by describing two novel genera and characterizing additional strains of *Faecalibaculum rodentium*.

Several steps were undertaken to ensure viability of anaerobic organisms throughout specimen collection, processing, cultivation, and isolation. Four intestinal (cecum, small intestine, and large intestine) samples were obtained from humanely euthanized female C57BL6J mice (Jackson Labs, VBar Harbor Me.), homogenized in pre-reduced anaerobically sterilized (PRAS) saline (Anaerobe Systems, Morgan Hill Calif.). Specimen 1 represented cecal microbiota from an adult mouse that had never received antibiotics and was being maintained on a high fat diet (diet-induced obesity diet # D12451, Research Diets) for 18 weeks. Two sets of flame-sterilized instruments were used to prevent contamination from mouse skin, hair, or environmental microbiota. Two thirds of the cecal contents were transferred to a sterile tube, frozen on dry ice, and stored at −80° C. for 2 years. Specimen 2 was a pool of cecal microbiota from three pregnant females; specimens were collected in Liquid Dental Transport Medium (Anaerobe Systems), homogenized, mixed with PRAS saline, and stored at −80° C. for several months. Further specimens were collected from an adult C57BL6J female mouse at sacrifice, from which all tissues were removed aseptically, and all of the large (Specimen 3) and small intestine (Specimen 4) were placed into sterile PRAS Chopped Meat Medium (Anaerobe Systems) tubes and vortex-mixed to homogenize the sample. Specimens 3 and 4 were inoculated to plates listed below immediately following collection. Specimen processing, inoculation, and isolation was performed in an anaerobic chamber under an atmosphere of 90% nitrogen, 5% hydrogen, and 5% carbon dioxide. For each of the 4 specimens, 10 μL of each intestinal suspension was plated on 5 different types of enriched (Brucella and MTGE Anaerobic Enrichment Agar, Anaerobe Systems, CA), selective (phenylethyl alcohol—PEA, and laked blood vancomycin—LKV) and selective-differential (Bacteroides bile esculin—BBE) media (all from Anaerobe Systems). Plates were observed daily for 7 days and isolates were sub-cultured onto Brucella or MTGE agar to obtain pure cultures. Isolates were preserved by suspending 1-2 plates of pure culture growth in four 0.5 mL aliquots of filter-sterilized powdered milk and frozen at −80 C.

The oxygen requirements were tested by incubating strains A3, A4, and K8 in anaerobic conditions (anaerobic chamber, 90% $N_2$, 5% $CO_2$, 5% $H_2$), in microaerophilic conditions (GasPak EZ Campy Container System, BD, 5-12% $CO_2$, 5-15% $O_2$, $N_2$ and other trace gases from ambient air), and aerobic conditions enriched with 5% $CO_2$. Growth was only observed in strict anaerobic conditions. Temperature testing was carried out at 30, 37, and 42° C. All strains grew optimally at 37° C., with weak growth detected at 30° C., and no growth detected at 42° C.

Figure 7:
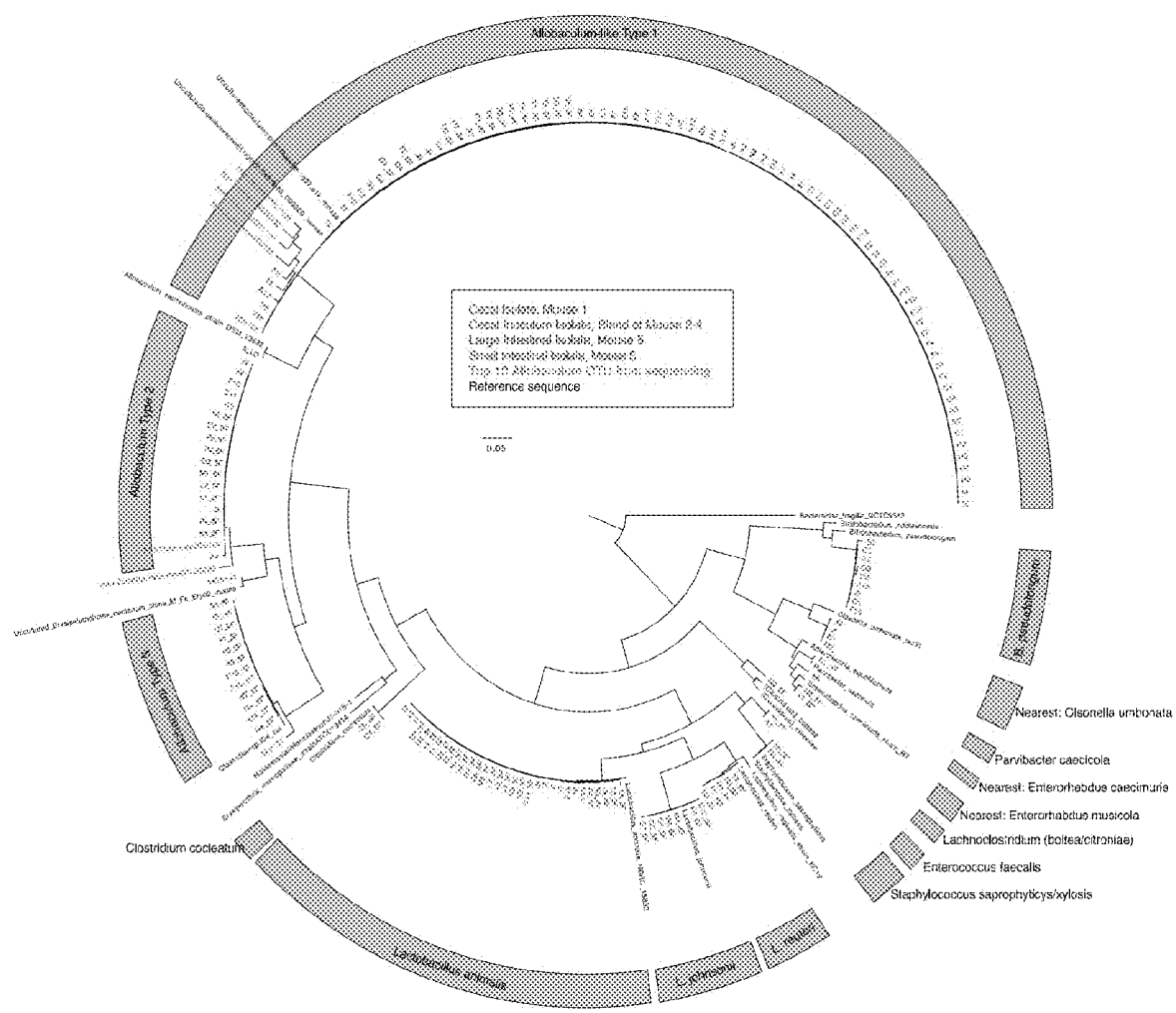
FIG. 7. Phylogenetic distribution of murine intestinal isolates. Four samples of intestinal contents from female mice were cultured under anaerobic conditions and 187 bacterial strains isolated. The 16S rRNA gene was characterized by Sanger sequencing and the nearest match was identified using BLAST. A phylogenetic distance matrix of isolates, reference strains, and the 10 *Allobaculum*-like (ALO) OTUs with highest relative abundance, as detected from high-throughput sequencing was constructed using QIIME and visualized using FigTree. Sequences are colored by sample source, OTUs identified via high throughput sequencing, or reference strain.

Near-full-length 16S rRNA sequences were amplified using the 8F and 1510R primers, as described[25], and sequences determined by the Sanger method (Macrogen, New York N.Y.). Abi files were converted to fastq by the Emboss script seqret (http://www.ebi.ac.uk/Tools/sfc/emboss_segret/). When Phred Q score was <30, the 5' and 3' end of the sequences were trimmed by PrinSeq[26]. Paired-end reads were assembled using fastq-join from Ea-Utils (http://code.google.com/p/ea-utils) with match >50%, and overlap of >100 base pairs. A phylogenetic distance matrix of isolates, reference strains, and the 10 "Allobaculum-like" OTUs (ALO) with highest relative abundance from a previous sequencing study1[5] was constructed using QIIME[27] and visualized using FigTree (http://tree.bio.ed.ac.uk/software/figtree/) (FIG. 7). The closest known relatives of the new isolates based on the 16S rRNA gene sequence were identified using the basic local alignment search tool (BLAST)[28]. Of the 187 isolates recovered, 118 clustered within the family Erysipelotrichaceae, 51 with other members of the Firmicutes and the remaining 18 isolates clustered with members of the Actinobacteria (Table 2). Within the Erysipelotrichaceae isolates, 111 of them formed three distinct clades.

Strains NYU-BL-A3T, NYU-BL-A4T, and NYU-BL-K8T were selected as the type strains for the phylogenetic ALO clades 1, 2, and 3, respectively, and both cluster with members of the family Erysipelotrichaceae. Strain NYU-BL-A3T is most closely related to *Allobaculum stercoricanis* (88.9% sequence similarity), *Faecalibaculum rodentium* (85.3%), *Faecalicoccus acidiformans* (85.7%), *Faecalicoccus pleomorphus* (84.9%), *Faecalitalea cylindroides* (84.5%), *Catenisphaera adipataccumulans* (84.2%), and *Holdemanella biformi* (84.0%). Strain NYU-BL-A4T is related to *Allobaculum stercoricanis* (84.1% sequence similarity), *Faecalibaculum rodentium* (86.7%), *Faecalicoccus acidiformans* (85.5%), *Faecalicoccus pleomorphus* (85.9%), *Faecalitalea cylindroides* (85.3%) and *Holdemanella biformi* (85.2%). Based on 16S rRNA gene sequence phylogenetic analysis, the novel strains form 2 groups within the family Erysipelotrichaceae but are distant from all members of this family. Pairwise similarities with the type strains were all <90% (Table 1), which is below the defined threshold for delineation of bacterial genera[29].

Figure 8:
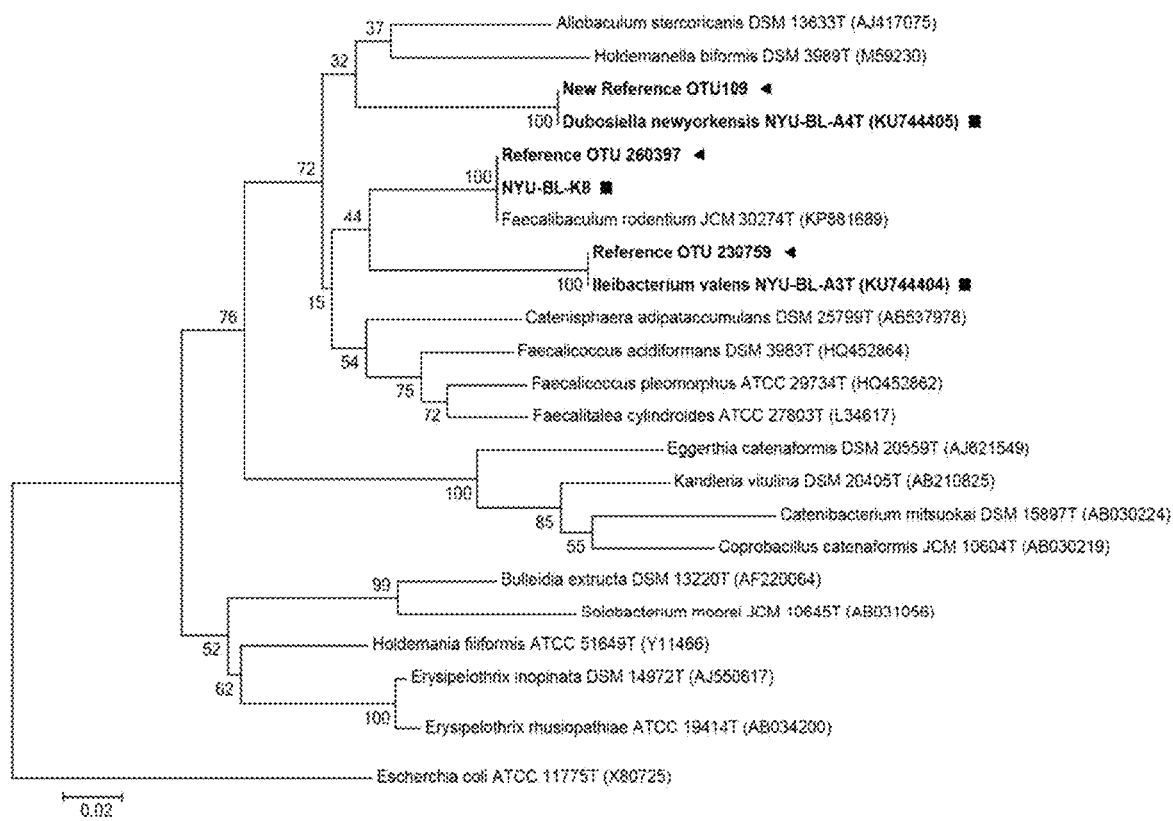
FIG. 8. Phylogenetic relationships of strains NYU-BL-A3T and NYU-BL-A4T with other members of the family Erysipelotrichaceae and top three *Allobaculum* OTUs. The evolutionary history was inferred using the Neighbor-Joining method. The percentages of replicate trees in which the associated taxa clustered together in the bootstrap test (1000 replicates) are shown next to the branches. The tree is drawn to scale; with branch lengths representing evolutionary distances in the units of the number of base substitutions per site computed using the Jukes-Cantor method. Triangles indicate OTU sequences obtained from high-throughput sequencing, squares represent sequences from cultured isolates. All other sequences are references from NCBI, accession number is in parentheses.

Example 6. Confirming Culture Representatives of Candidate Metabolically Interactive Bacteria To determine the precise relationships with members of the Erysipelotrichaceae, and to determine whether these isolates matched the top 3 *Allobaculum* OTUs, a phylogenetic analysis was performed (FIG. 8). The newly determined sequences from a representative from each of the three clades of isolated *Allobaculum*-like organisms, the top 3 *Allobaculum* sequencing OTUs, and reference sequences were aligned using ClustalW[30] and the forward and reverse ends were trimmed, when uneven. The phylogenetic analysis was performed using MEGA[31] using the neighbor-joining method[32] and evolutionary distances were computed using the Jukes-Cantor method[33]. All positions containing gaps and missing data were eliminated. There were a total of 1215 informative positions in the final dataset. Confidence levels of the branching patterns was performed using the bootstrap algorithm based on 1000 replicates[34]. One group of isolates, ALO group 1, clustered on a branch that was phylogenetically related to *Allobaculum stercoricanis*, but represented a distinct phylogenetic lineage (FIG. 8). Two other phylogenetic clusters were seen, most related to each other more than to *Allobaculum* and ALO group 1, and one matching *Faecalibaculum rodentium* with 99.9% identity.

Figure 9:
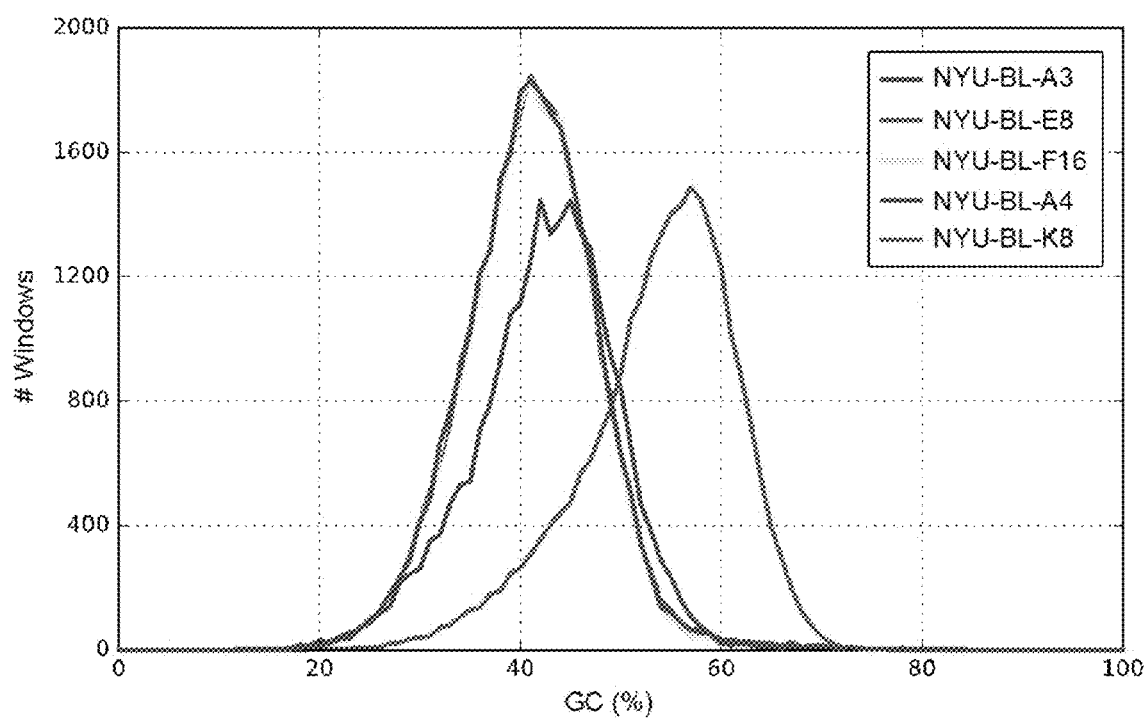
FIG. 9. GC composition. Percent GC calculated over the entire genome for 5 novel strains of Erysipelotrichaceae, calculated using the quality assessment tool for genome assemblies (QUAST).

Genomic GC % was calculated from whole genome sequences. DNA from strains NYU-BL-A3T, NYU-BL-A4T, NYU-BL-E8, NYU-BL-F16, and NYU-BL-K8 was sequenced by 150×150 paired end reads on the MiSeq platform. Individual genomes were assembled using SPAdes[35], using the parameters recommended for longer Illumina reads: k-mer sizes of 21, 33, 55, 77, 99, and 127, with the number of mismatches and indels reduced by MismatchCorrector in SPAdes (Bankevich et al., Journal of Computational Biology, 2012, 19(5):455-477). Genome assembly quality control and % GC calculation was performed using the quality assessment tool for genome assemblies (QUAST)[36]. The GC % content for NYU-BL-A3T, NYU-BL-E8, NYU-BL-F16, and NYU-BL-A4T, and were 41.2%, 41.2%, 41.0%, and 42.5%, respectively, and for NYU-BL-K8 was 53.7% (FIG. 9).

Except as stated for morphological observations and biochemical characterizations, strains were grown on Brucella agar supplemented with 5% defibrinated sheep blood (Anaerobe Systems,) at 37° C. for 48 h. Cells were examined with an Olympus CX41 microscope using phase contrast at 1000× magnification. For biochemical characterization, API Rapid ID 32A (API bioMérieux, Marcy l'Etoile, France) and RapID-ANA II System (Innovative Diagnostic Systems, Inc., Atlanta Ga.) were used following the manufacturer's instructions. All biochemical tests were performed in duplicate. Other phenotypic and biochemical tests were performed as described[37].

For chemotaxonomic characterization, cells were incubated for 72 hr at 37° C. on Brucella agar 5% sheep blood added. Conditions were chosen to allow comparison with values available in the literature. Analysis was performed at the Center for Microbial Identification and Taxonomy (University of Oklahoma, Norman, Okla.). Fatty acid methyl esters were extracted using the Sherlock Microbial Identification System (MIDI) version 6.1, as described[38,39]. Analysis was performed using an Agilent Technologies 6890N gas chromatograph equipped with a phenyl methyl silicone fused silica capillary column (HP-2 25 m×0.2 mm×0.33 μm film thickness) and a flame ionization detector with hydrogen used as the carrier gas. The temperature program was initiated at 170° C. and increased at 5° C. min$^{-1}$ reaching a final temperature of 270° C. Fatty acids were identified and expressed in the form of percentages using the SMOORE6 peak-naming database. Whole cell hydrolysates were examined by thin-layer chromatography (TLC) for the presence of 2, 6-diaminopimelic acid isomers by the method of Schumann (2011). Tables 3 and 4 show that the major (>10%) fatty acids of NYU-BL-A3T consist of $C_{16:0}$ (34.2%), and $C_{18:0}$ (18.9%), and minor products include $C_{9:0}$ (2.6%), $C_{10:0}$ (4.5%), $C_{11:0}$ (2.3%), $C_{12:0}$ (4.9%), $C_{13:0}$ (2.2%), $C_{14:0}$ (6.0%), $C_{15:0}$ (2.8%), $C_{17:0}$ (3.4%), $C_{18:1\omega9c}$ (9.8%), and $C_{18:2\omega6,9c/C18:0ante}$ (2.8%). The major (>10%) fatty acids of NYU-BL-A4T consist of $C_{10:0}$ (19.3%), $C_{16:0}$ (31.4%), $C_{18:0}$ (12.1%), and $C_{18:2\omega6,9c/C18:0ante}$ (13.1%), minor products include $C_{9:0}$ (3.3%), $C_{12:0}$ (3.6%), $C_{14:0}$ (6.1%), $C_{16:1\omega7c/C16:1 \omega6c}$ (9.8%). $C_{18:2\omega6,9c/C18:0ante}$ (9.8%).

Strains NYU-BL-A3T and NYU-BL-A4T both stain Gram-positive, and are strictly anaerobic non-spore forming rods. These novel isolates from the murine gut were found to possess biochemical and chemotaxonomic traits consistent with organisms belonging to Erysipelotrichaceae, but could clearly be distinguished from their nearest phylogenetic relatives using the characteristics shown in Tables 3-5. In addition to its unique 16S rRNA gene sequence, NYU-BL-A3T can be distinguished from NYU-BL-A4T and other members of the Erysipelotrichaceae by its positive α-galactosidase, β-galactosidase, and β-glucosidase activity, and its inability to produce phospho-6-β-galactosidase, β-glucuronidase, pyroglutamic acid arylamidase, glycine arylamidase, leucyl glycine arylamidase, using the API rapid 32A system (Table 5). NYU-BL-A4T can be distinguished from the other members of the Erysipelotrichaceae family based on positive activity for phospho-β-galactosidase, β-glucosidase, β-glucoronidase, arginine arylamidase, leucine arylamidase, leucyl glycine arylamidase, proglutamic acid arylamidase, glycine arylamidase, and histidine arylamidase, and a negative reaction for β-galactosidase. F. rodentium strains from NYU have similar reactions to the type strain of F. rodentium, except 50% of NYU strains are weakly positive for α-galactosidase, and 100% are positive for β-glucosidase, whereas the type strain is negative, and the NYU strains are negative for arginine arylamidase and leucyl glycine arylamidase, and 66% of the strains are negative for D-raffinose, while the type strain of F. rodentium is positive.

The RapID-ANA II System is also very useful in the differentiation of the groups represented by strains NYU-BL-A3T and NYU-BL-A4T with the former failing to produce alkaline phosphatase, α-arabinosidase, arginine arylamidase, α-fucosidase, α-glucosidase, glycine arylamidase, indole, leucylglycine aminopeptidase, p-nitrophenyl-β-disaccharide, ortho-nitrophenyl-β-galactoside, phenylalanine arylamidase, proline arylamidase, and urease (Table 6). Furthermore, strain NYU-BL-A3T produces <5% $C_{10:0}$, a major component of the fatty acid profile of NYU-BL-A4T.

Based on phylogenetic, biochemical and chemotaxonomic criteria, two novel genera are proposed, *Ileibacterium valens* gen. nov., sp. nov. and *Dubosiella newyorkensis* gen. nov., sp. nov.

Description of *Ileibacterium* gen. nov.

I.le.i.bac.te'ri.um. N.L. neut. n. ileum the distal part of the small intestine; L. neut. n. bacterium a small rod; N.L. neut. n. *Ileibacterium* a rod from the ileum.

Cells are Gram-stain-positive, non-spore-forming, short bacilli or cocci. The organism is strictly anaerobic. Major fatty acids (>10%) are $C_{16:0}$, and $C_{18:0}$. The diagnostic diamino acid of the peptidoglycan is meso-DAP. Strains have been isolated from murine intestinal contents. The type species is *Ileibacterium valens*. Based on 16S rRNA gene sequencing, species are located in the radiation of the family Erysipelotrichaceae[21].

*Ileibacterium valens* sp. nov.

valens. va.lēns. L. pres. part. valens healthy; N.L. part. adj. valens healthy, strong, vigorous This strain was originally named *Ileibacterium lipovorans*. It was, however, renamed *Ileibacterium valens* because: 1) lipid-degredataion activity was not detected after performing a lipase test; 2) the population of this strain is associated with metabolic health, and 3) this strain vigorously responds to dietary changes increasing up to 10-fold following introduction of a high-fat, high sucrose diet.

In addition to the characteristics provided in the genus description, cells are may be short bacilli or cocci singly, in pairs and chains. When grown on Brucella agar supplemented with blood, gray colored colonies are formed and grow up to 0.5 mm in 24 hours, and 2-3 mm in 48-72 hours. The organism will grow in MTGE broth, but not in Brucella broth, Chopped Meat Medium Broth, or Thioglycolate broth. Growth is optimal at 37° C., weak growth occurs at 30° C. but not at 45° C. Using the API Rapid 32A test system (Biomereux), (Table 5), positive reactions are observed for α-galactosidase, β-galactosidase and β-glucosidase (1 strain weak). Negative reactions are obtained for N-acetyl-β-glucosaminidase, alanine arylamidase, alkaline phosphatase, α-arabinosidase, arginine arylamidase, arginine dihydrolase, phospho-6-β-galactosidase, β-glucuronidase, glycine arylamidase, glutamyl glutamic acid, α-fucosidase, glutamic acid decarboxylase, histidine arylamidase, indole, leucine arylamidase, leucyl glycine arylamidase, nitratephenylalanine arylamidase, proline arylamidase, pyroglutamic acid arylamidase, serine arylamidase, tyrosine arylamidase and urease. α-glucosidase is either negative or weakly positive. Variable reactions are obtained for D-mannose and D-raffinose. Using the RapID-ANA II System (Table 6), positive reactions was only obtained with α-galactosidase, positive or weakly positive reactions are obtained with β-glucosidase. Negative reactions were obtained with alkaline phosphatase, α-arabinosidase, arginine arylamidase, α-fucosidase, α-glucosidase, glycine arylamidase, indole, leucylglycine aminopeptidase, p-nitrophenyl-b-diasacharride, ortho-nitrophenyl-β-galactoside, phenylalanine arylamidase, proline arylamidase, and urease. Pyroglutamic acid arylamidase and serine arylamidase give negative or very weak reactions. A variable reaction is obtained for β-N-acetyl-α-glucosaminidase activity.

The type strain is NYU-BL-A3T (=DSM 33318), isolated from murine intestinal contents. The G+C of the DNA of the type strain is 41.1 mol %.

*Dubosiella* Gen. Nov.

Du.bo.s.iel'la. N.L. fem. dim. named after the late French-born American microbiologist Rene Dubos (1901-1982) for his numerous important contributions to the field of microbiology and ecology, and his early discoveries of antibiotics.

Cells are Gram-stain-positive, non-spore-forming, short bacilli and cocci. The organism is strictly anaerobic. Major fatty acids (>10%) are $C_{16:0}$, and $C_{18:0}$. The diagnostic diamino acid of the peptidoglycan is meso-DAP. Strains have been isolated from murine intestinal contents. The type species is *Dubosiella newyorkensis*. Based on 16S rRNA gene sequencing, species are located in the radiation of the family Erysipelotrichaceae (Stackebrandt, 2009).

*Dubosiella newyorkensis* gen. nov. sp. nov.

new.york.en'sis. N.L. fem. adj. newyorkensis of or belonging to the state of New York in the USA, where the first isolate was obtained.

In addition to the characteristics provided in the genus description, cells may be short bacilli or cocci, appearing singly, in pairs and in chains. When grown on *Brucella* agar supplemented with blood, gray-colored colonies are formed and grow up to 0.5 mm in 24 hours and 2-3 mm in 48-72 hours. The organism will grow in MTGE broth, but not in *Brucella* broth, Chopped Meat Medium Broth, or Thioglycolate broth. Growth is optimal at 37° C., weak growth occurs at 30° C. but not at 45° C. Using the API Rapid 32A test system (Table 5), positive reactions are observed for arginine arylamidase, 6-Phospho-β-galactosidase, β-glucosidase, β-glucuronidase, glycine arylamidase, histidine arylamidase, leucine arylamidase, leucyl glycine arylamidase and pyroglutamic acid arylamidase. Negative reactions are obtained for alanine arylamidase, alkaline phosphatase, α-arabinosidase, arginine dihydrolase, glutamyl glutamic acid, α-fucosidase, β-galactosidase, glutamic acid decarboxylase, indole, nitrate, phenylalanine arylamidase, proline arylamidase, serine arylamidase, tyrosine arylamidase, and urease. α-glucosidase is either negative or weakly positive. Variable reactions are obtained for N-acetyl-β-glucosaminidase, α-galactosidase, D-mannose, and D-raffinose. Using the rapid RapID-ANA II System (Table 6), positive reactions are obtained with β-N-acetyl-α-glucosaminidase, α-glucosidase, β-glucosidase, α-galactosidase, leucyl glycine aminopeptidase, glycine arylamidase, phenylalanine arylamidase, proline arylamidase. Negative reactions are obtained with alkaline phosphatase, α-arabinosidase, arginine arylamidase, α-fucosidase, indole, p-nitrophenyl-β-disaccharide, ortho-nitrophenyl-β-galactoside, and serine arylamidase, and urease. Pyroglutamic acid arylamidase is variable.

The type strain is NYU-BL-A4T (DSM 33317), isolated from murine intestinal contents. The G+C of the DNA of the type strain is 42.5 mol %.

Example 7. Strain-Specific Metabolic Associations

Figure 10A:
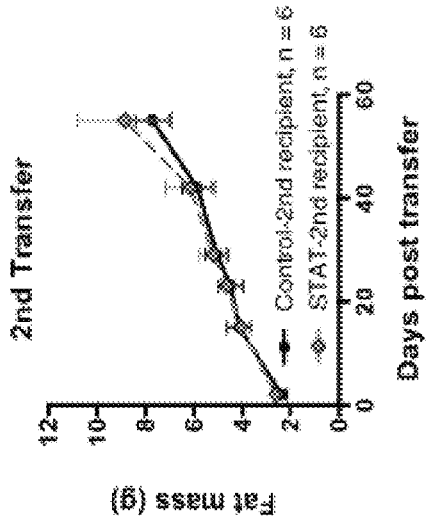
Figure 10B:
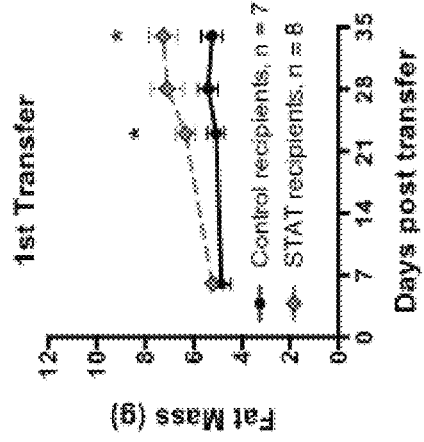
Figure 10C:
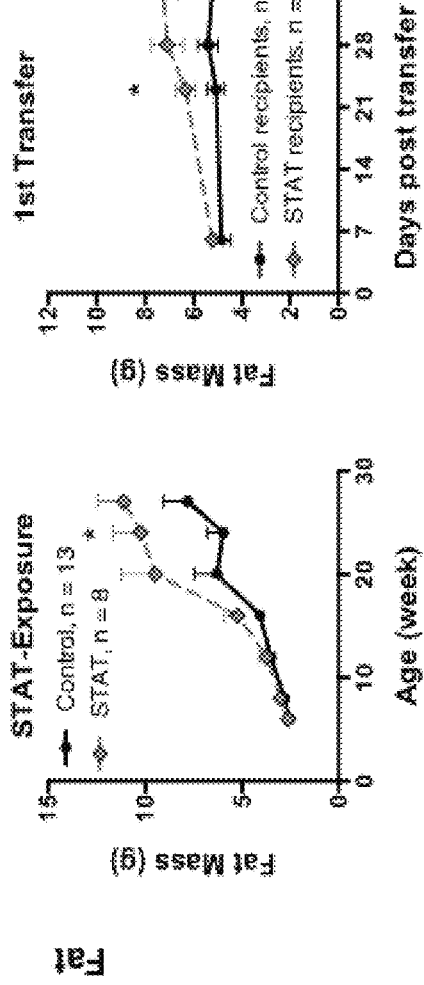
Figure 10D:
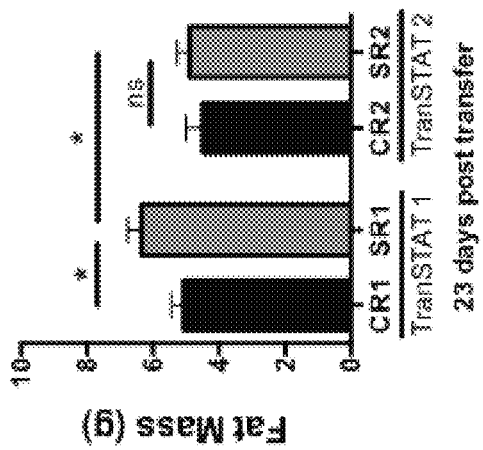
Figure 10E:
Figure 10E:
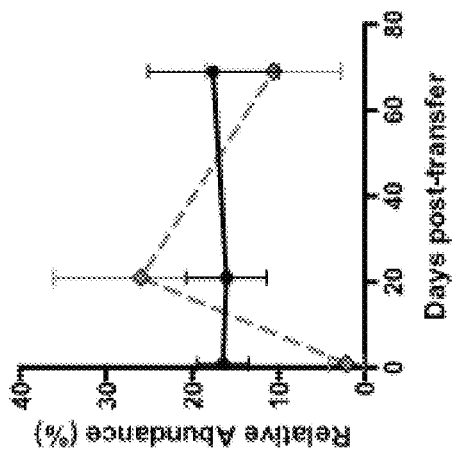
Figure 10F:
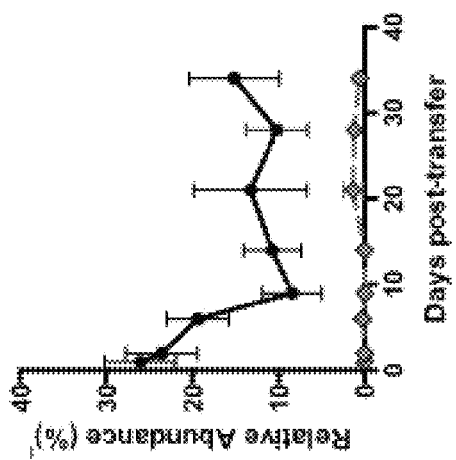
Figure 10G:
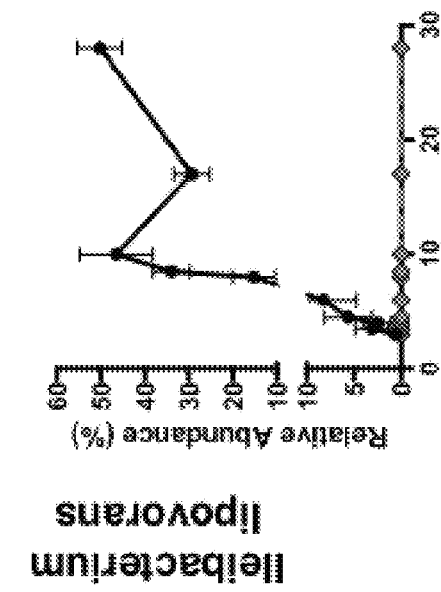
Figure 10K:
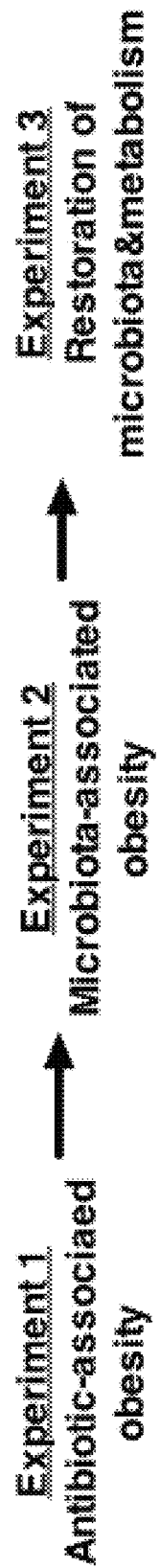
Figure 10K:
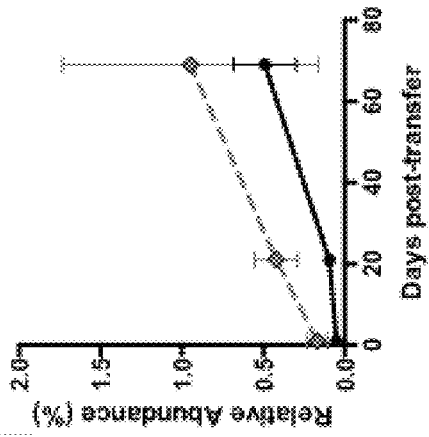
Figure 10L:
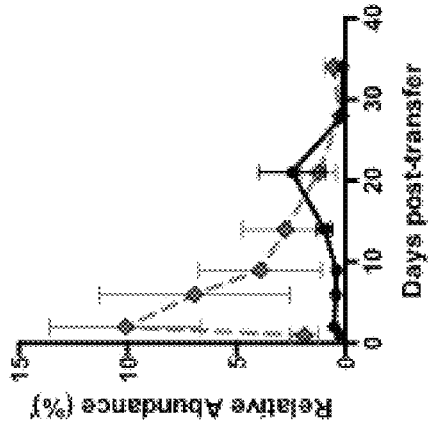
Figure 10M:
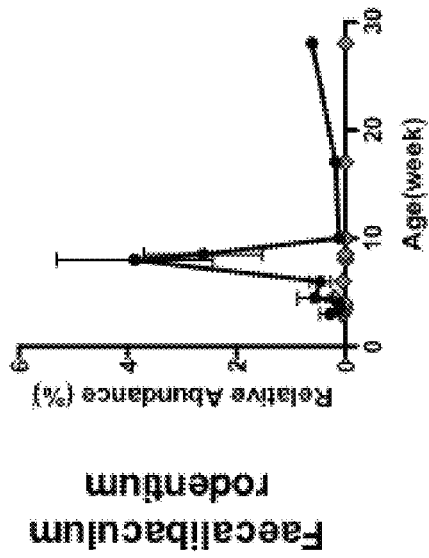

Obtaining cultured representatives that matched the sequencing *Allobaculum* OTUs demonstrated that there were actually unique and novel genera accounting for the inventors' previous sequencing data. The information from novel identification was used to go back and examine the prevalence of *Ileibacterium* valens, *Dubosiella newyorken-sis*, and *Faecalibaculum rodentium* in the models of antibiotic- and microbe-induced obesity. As expected, low levels of all three genera were detected in the model of antibiotic-induced obesity (FIG. 10A, 10E, 10H, 10K). In addition, germ-free mice colonized with microbiota that were deficient in *Ileibacterium* valens and *Dubosiella newyorkensis* (FIG. 10B, 10F, 10I) gained more fat and weight over time and had decreased intestinal defenses (FIG. 2), confirming their protective metabolic role. The third most prevalent ALO OTU, which corresponds to *Faecalibaculum*, was actually higher in STAT-microbiota recipients (FIG. 10L), providing evidence that it is not sufficient to restore metabolic or immunologic responses. In a third experiment, microbiota were transferred from the previously colonized germ-free mice into a second group of germ-free recipients. In this third experiment, no change in total, lean or fat mass was detected (FIG. 10C) and these mice had a similar fat mass to the lean controls in experiment 2 (FIG. 10D). In this experiment, the levels of *Ileibacterium* valens and *Dubosiella newyorkensis* increased to the same extent of control levels or surpassed control levels. That the microbiota populations and metabolic health were restored at the same time provides evidence that fat mass can be reduced by increasing these bacteria.

Figure 11:
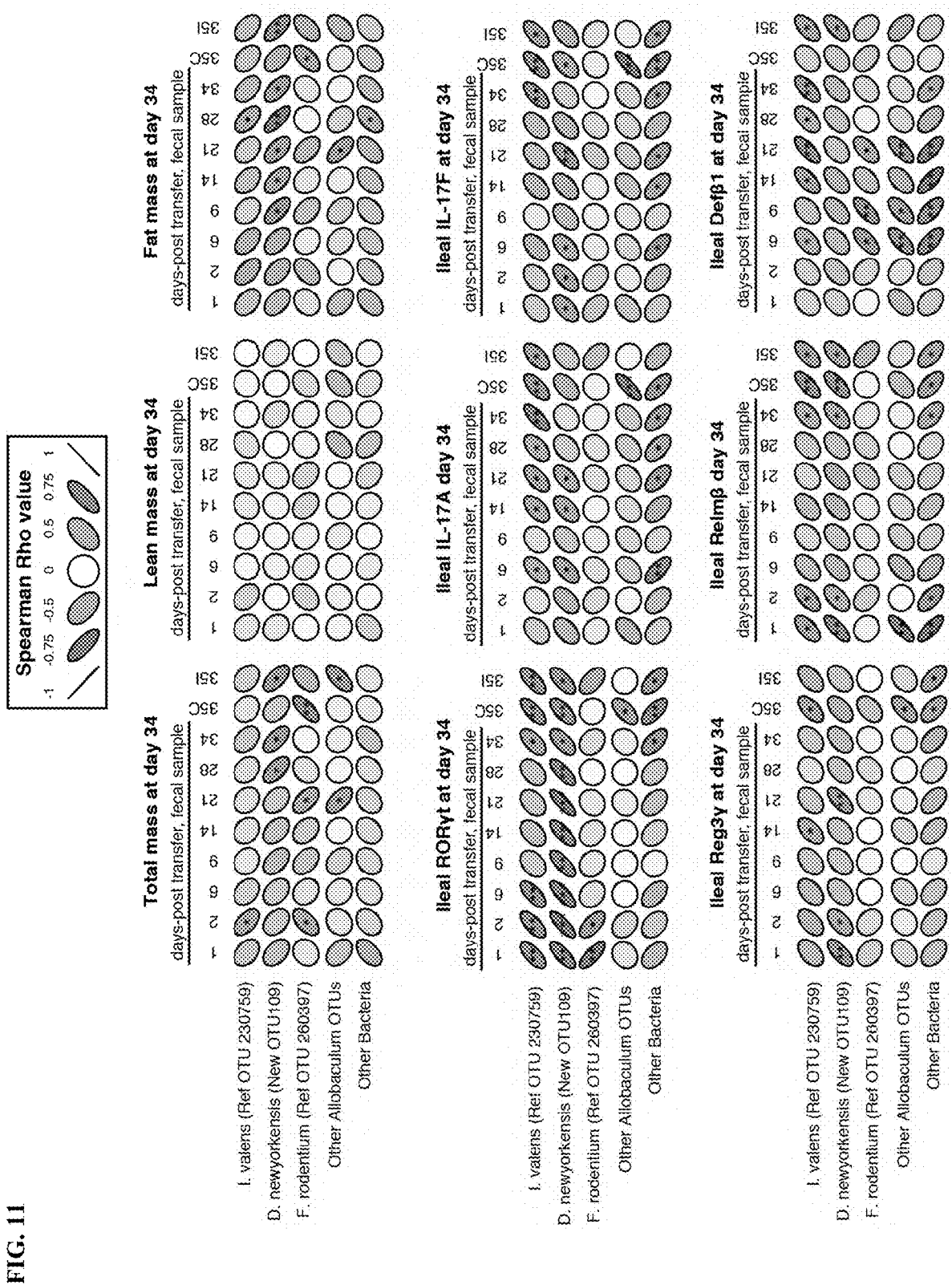
FIG. 11. Metabolic and immunologic correlations with novel Erysipelotrichacaee members. The levels of *Ileibacterium* and *Dubosiella* over time have a consistent negative correlation with total and fat mass, while they have a consistent and significant correlation with the expression of markers of ileal immune defense, including RORγT, IL-17A, IL-17F, RegIIIγ, Relmβ, and Defβ, spearman correlation Rho values are plotted as an ellipse and significance levels are noted with an *. *Faecalibaculum* and other *Allobaculum* OTUs have opposing relationships or no correlation, demonstrating the strain specific nature of the metabolic and immunologic relationships.

Next, metabolic relationships were examined with the top three ALO, which correspond to the cultured isolates. Originally, it was found that mis-identified *Allobaculum* populations over time had a significant negative correlation with fat mass (FIG. 3), suggesting protective metabolic relationships. However, examining relationships at the I level revealed different biological associations with the three different ALO OTUs (FIG. 11). Only ALO1 and 2 continued to have significant negative correlations with fat mass, while ALO3 had weak associations, and one significant positive correlation with fat. That relationships were detected immediately after microbiota transfer, preceding the development of elevated fat, suggests these bacteria induce metabolic changes. The differing relationships provide evidence that individual strains of bacteria within a single genus can have alternate metabolic effects.

The interaction between the ALO with a marker of intestinal defense was then examined. Several studies have demonstrated that intestinal barrier function is a critical component of metabolic health, and disruptions at the intestinal interface, including weakening of tight junctions[40], thinning of mucus layer[41], deletion of TLR5[42], or deletion of the inflammasome components, can lead to systemic inflammation and obesity. In the model of MIO, the inventors similarly demonstrate that microbiota disruption leads to decreased expression of intestinal Th17 cell markers and antimicrobial peptides. In this analysis, multiple significant positive correlations were detected with *Ileibacterium valens* and *Dubosiella newyorkensis*, but negative correlations or no strong correlation with *Faecalibaculum rodentium*, providing evidence that there are genus specific relationships with intestinal immunity. That high levels of *Ileibacterium valens* and *Dubosiella newyorkensis* to germ-free mice were administered in the controls, and then elicited changes in immune gene expression provides evidence that these two genera can alter intestinal immunity.

TABLE 1

Percent identity of top 3 Allobaculum OTUs with the Allobaculum reference strain and other genera in the family Erysipelotrichaceae.

| | NYU-BL-A3 | NYU-BL-A4 | NYU-BL-K8 |
|---|---|---|---|
| Reference OTU 230759 | 100.0% | 80.2% | 88.2% |
| New.ReferenceOTU109 | 80.2% | 100.0% | 86.3% |
| Reference OTU 260397 | 88.2% | 86.3% | 100.0% |
| Allobaculum_stercoricanis_DSM_13633T_(AJ417075) | 84.8% | 84.8% | 88.2% |
| Faecalibaculum_rodentium*_JCM_30274T_(KP881689) | 88.2% | 86.3% | 100.0% |
| Bulleidia_extructa_DSM_13220T_(AF220064) | 73.6% | 78.6% | 75.8% |
| Catenibacterium_mitsuokai_DSM_15897T_(AB030224) | 70.0% | 71.2% | 70.6% |
| Coprobacillus_catenaformis_JCM_10604T_(AB030219) | 75.3% | 74.2% | 73.6% |
| Eggerthia_catenaformis_DSM_20559T_(AJ621549) | 75.8% | 79.1% | 75.8% |
| Erysipelothrix_inopinata_DSM_14972T_(AJ550617) | 79.1% | 78.6% | 80.7% |
| Erysipelothrix_rhusiopathiae_ATCC_19414T_(AB034200) | 79.7% | 78.6% | 80.2% |
| Erysipelothrix_tonsillarum_ATCC_43339T_(AB055906) | 79.7% | 78.6% | 80.2% |
| Holdemania_filiformis_ATCC_51649T_(Y11466) | 81.2% | 79.7% | 81.2% |
| Kandleria_vitulina_DSM_20405T_(AB210825) | 76.4% | 74.2% | 75.8% |
| Solobacterium_moorei_JCM_10645T_(AB031056) | 71.2% | 74.7% | 72.4% |
| Turicibacter_sanguinensis_DSM_14220T_(AF349724) | 78.1% | 76.4% | 79.1% |
| Faecalicoccus_acidiformans_DSM_3983T_(HQ452864) | 85.3% | 84.8% | 87.2% |
| Faecalicoccus_pleomorphus_ATCC_29734T_(HQ452862) | 84.8% | 85.3% | 88.2% |
| Faecalitalea_cylindroides_ATCC_27803T_(L34617) | 83.8% | 86.7% | 88.2% |
| Holdemanella_biformis_DSM_3989T_(M59230) | 80.2% | 86.7% | 86.7% |
| Catenisphaera_adipataccumulans_DSM_25799T_(AB537978) | 85.3% | 85.8% | 87.7% |
| Ileibacterium_valens_NYU-BL-A3T_(KU744404) | 100.0% | 80.2% | 88.2% |
| Dubosiella_newyorkensis_NYU-BL-A4T_(KU744405) | 80.2% | 100.0% | 86.3% |
| Isolate NYU-BL-K8 | 88.2% | 86.3% | 100.0% |
| Escherichia_coli_ATCC_11775T_(X80725) | 73.0% | 68.2% | 68.8% |

TABLE 2

Closest taxonomic matches of recovered bacterial isolates.

| # Isolates per sample | | | | | BLAST | | | |
|---|---|---|---|---|---|---|---|---|
| Total | S1 | S2 | S3 | S4 | Class | Nearest Named Match | Sequence Coverage | Sequence Identity |
| 84 | 67 | — | 7 | 10 | Erysipelotricha | Allobaculum stercoricanis (Clade 1) | 99% | 88% |
| 18 | 7 | 4 | 5 | 2 | | Allobaculum stercoricanis (Clade 2) | 96% | 88% |
| 13 | — | 7 | 4 | 2 | | Faecalibaculum rodentium | 100% | 99% |
| 1 | — | — | 1 | — | | Coprobacillus cateniformis | 99% | 94% |
| 2 | — | — | 2 | — | | Clostridium cocleatum | 100% | 100% |
| 1 | — | — | 1 | — | Clostridia | Lachnoclostridium citronea/boltae | 97% | 93% |
| 2 | 1 | 1 | — | — | Bacilli | Enterococcus faecalis | 100% | 100% |
| 34 | 10 | 10 | 3 | 11 | | Lactobacillus animalis | 100% | 99% |
| 7 | — | 4 | 2 | 1 | | Lactobacillus johnsonii | 100% | 99% |
| 5 | — | — | 1 | 4 | | Lactobacillus reuteri | 100% | 99% |
| 2 | — | — | — | 2 | | Staphylococcus saprophyticus/xylosis | 100% | 99% |
| 1 | 1 | — | — | — | Actinobacteria | Enterorhabdus caecimuris | 97% | 97% |
| 2 | — | — | 2 | — | | Enterorhabdus musicola | 97% | 99% |
| 1 | — | — | 1 | — | | Parvibacter caecolia | 100% | 99% |
| 5 | 1 | 4 | — | — | | Olsonella umbonata | 98 | 93% |
| 9 | 7 | — | 2 | — | | Bifidobacterium pseudolongum | 100 | 99% |

S1 = sample 1, cecal contents from 18-week old female mouse receiving high fat diet (RFD);
S2 = sample 2, cecal contents from a pool of 3 pregnant mice.
S3 = sample 3, large intestinal contents of an adult female mouse on normal chow.
S4 = sample 4, small intestinal contents of an adult female mouse on normal chow.

TABLE 3

Characteristics that distinguish strains A3T and A4T from the type strains of related species in the family Erysipelotrichaceae.

| Characteristic API rapid 32A | 1 | 2 | 3 | 4[a] | 5[b] | 6[c] | 7[a] | 8[a] | 9[a] | 10[d] |
|---|---|---|---|---|---|---|---|---|---|---|
| β-glucosidase | + | + | + | + | − | − | − | − | − | − |
| α-Galactosidase | + | +(57) | w(50) | − | − | − | − | − | − | − |
| β-galactosidase | + | − | − | + | − | − | − | w | − | − |
| 6-phospho-β-galactosidase | − | + | − | − | − | − | − | − | − | − |
| β-glucuronidase | − | + | − | − | − | − | − | − | − | − |
| Arginine arylamidase | − | + | − | + | + | − | + | − | − | − |
| Pyroglutamic acid arylamidase | − | + | − | − | − | − | + | w | w | − |
| Glycine arylamidase | − | + | + | w | + | − | w | − | − | − |
| Histidine arylamidase | − | + | − | w | − | − | w | − | − | − |
| Leucyl glycine arylamidase | − | + | − | − | + | − | w | − | − | − |
| Leucine arylamidase | − | + | + | − | + | − | w | − | − | − |
| Major fatty acids | $C_{16:0}$, $C_{18:0}$, $C_{18:1\omega9c}$ | $C_{10:0}$, $C_{16:0}$, $C_{18:0}$, $C_{18:1\omega9c}$ | | $C_{10:0}$, $C_{16:0}$, $C_{18:0}$, $C_{18:1\omega9c}$ | $C_{10:0}$, $C_{16:0}$, $C_{18:0}$, $C_{18:1\omega9c}$, $C_{18:2\omega6,9c/18:0ante}$ | $C_{16:0}$, $C_{18:1\omega9c}$ | $C_{16:0}$, $C_{18:1\omega9c}$, iso-$C_{19:11}$, iso-$C_{17:1}$/anteiso-$C_{17:1}$ | $C_{16:0}$, $C_{16:0DMA}$, $C_{18:0}$, $C_{18:1\omega9c}$ | $C_{16:0}$, $C_{16:0DMA}$, $C_{18:0}$, $C_{18:1\omega9c}$, $C_{18:2\omega,12c}$ | $C_{14:0}$, $C_{14:0DMA}$, $C_{16:0}$, $C_{16:0DMA}$, $C_{18:0}$, $C_{18:0DMA}$ |
| G + C | 41.1 | 42.5 | 53.7 | 36.9 | 52.3 | 40.4 | 38.5 | 33.3 | 32.1 | 47.7 |

+ = positive, − = negative, w = weak, numbers in parentheses indicate how many strains are positive or weakly positive if less than 100%. Organisms numbers 2 and 3 are + and w for α-galactosidase, respectively. Data taken from [a]Verbarg et al., 2014, [b]Chang et al., 2015; [c]De Maesschalck et al., 2014, [d]Kanno et al., 2015.

Strains: 1, NYU-BL-A3T; 2, NYU-BL-A4T; 3, NYU-BL-K8; 4, *Allobaculum stercoricanis* DSM 13633T; 5, *Faecalibaculum rodentium* KCTC 15484T; 6, *Faecalicoccus acidiformans* LMG 27248T; 7, *Faecalicoccus pleomorphus* KCTC 3656T; 8, *Faecalitalea cylindroides* ATCC 27803T; 9, *Holdemanella biformis* KCTC 5969T; 10, *Catenisphaera adipataccumulans* DSM 25799T.

TABLE 4

Cellular fatty acid composition of strains NYU-BL-A3T, NYU-BL-A4T, and *A. stercoricanis*

| Fatty acid[a] | A3 [T] | A4 [T] | *Allobaculum stercoricanis* DSM 13633[T] |
|---|---|---|---|
| $C_{9:0}$ | 2.6 | 3.3 | 1.3 |
| $C_{10:0}$ | 4.5 | 19.3 | 9.8 |
| $C_{11:0}$ | 2.3 | — | — |
| $C_{12:0}$ | 4.9 | 3.6 | 2.7 |
| $C_{13:0}$ | 2.2 | — | — |
| $C_{14:0}$ | 6.0 | 6.1 | 5.8 |
| $C_{15:0}$ | 2.8 | — | 1.0 |
| $C_{16:1\omega7c/16:1\omega6c}$ | — | 1.4 | 1.5 |
| $C_{16:0}$ | 34.2 | 31.4 | 33.7 |
| $C_{17:0}$ | 3.4 | — | 1.0 |
| $C_{16:0\ 2OH}$ | — | — | — |
| $C_{18:0}$ | 18.9 | 12.0 | 12.0 |
| $C_{18:2\omega6,\ 9c/18:0\ ante}$ | 2.8 | 9.8 | 12.5 |
| $C_{18:1\omega9c}$ | 9.4 | 13.0 | 15.2 |
| $C_{18:1\omega7c}$ | — | — | 3.5 |

[a]Predominant products are shown in bold, values <1% are not shown.

TABLE 5

Biochemical Characterization of the 20 Allobaculum-like organisms (ALOs) by the API Rapid32

| API Rapid 32 assay | | Strain Group | A3 | Q5 | R1 | F16 | E8 | P1 | U3 | A4 | F15 | L1 | L3 | M1 | P2 | S4 | K8 | M7 | P3 | Q1 | R5 | S3 |
|---|---|---|---|---|---|---|---|---|---|---|---|---|---|---|---|---|---|---|---|---|---|---|
| | | | | | ALO 1 | | | | | | | | | ALO 2 | | | | | | ALO 3 | | |
| Urease | URE | | − | − | − | − | − | − | − | − | − | − | − | − | − | − | − | − | − | − | − | − |
| Arginine dihydrolase | ADH | | − | − | − | − | − | − | − | − | − | − | − | − | − | − | − | − | − | − | − | − |
| α-galactosidase | αGAL | | + | + | + | + | + | + | + | + | − | + | + | + | − | − | w | − | − | w | w | − |
| β-galactosidase | βGAL | | + | + | + | + | + | + | + | − | − | − | − | − | − | − | − | − | − | − | − | − |
| β-galactosidase-6-phosphate | βGP | | − | − | − | − | − | − | − | + | + | + | + | + | + | + | − | − | − | − | − | − |
| α-glucosidase | αGLU | | w | − | − | w | w | − | − | + | + | w | + | + | + | + | − | − | − | − | − | − |
| β-glucosidase | βGLU | | + | + | + | w | + | + | + | + | + | + | + | + | + | + | + | + | + | + | + | + |
| α-arabinosidase | αARA | | − | − | − | − | − | − | − | − | − | − | − | − | − | − | − | − | − | − | − | − |

TABLE 5-continued

Biochemical Characterization of the 20 Allobaculum-like organisms (ALOs) by the API Rapid32

| API Rapid 32 assay | Strain Group | A3 | Q5 | R1 | F16 ALO 1 | E8 | P1 | U3 | A4 | F15 | L1 | L3 | M1 ALO 2 | P2 | S4 | K8 | M7 | P3 ALO 3 | Q1 | R5 | S3 |
|---|---|---|---|---|---|---|---|---|---|---|---|---|---|---|---|---|---|---|---|---|---|
| β-glucuronidase | βGUR | – | – | – | – | – | – | – | + | + | + | + | + | + | + | – | – | – | – | – | – |
| β-N-Acetyl-α-glucosaminidase | βNAG | – | – | – | – | – | – | – | – | – | w | + | + | + | + | – | – | – | – | – | – |
| D-mannose | MNE | + | – | – | + | + | + | + | + | + | + | + | + | – | + | + | + | + | + | + | + |
| D-raffinose | RAF | + | – | – | + | + | + | – | – | – | + | + | + | – | – | + | + | – | – | – | – |
| Glutamic acid decarboxylase | GDC | – | – | – | – | – | – | – | – | – | – | – | – | – | – | – | – | – | – | – | – |
| α-fucosidase | αGUC | – | – | – | – | – | – | – | – | – | – | – | – | – | – | – | – | – | – | – | – |
| Nitrate reduction | NIT | – | – | – | – | – | – | – | – | – | – | – | – | – | – | – | – | – | – | – | – |
| Indole | IND | – | – | – | – | – | – | – | – | – | – | – | – | – | – | – | – | – | – | – | – |
| Alkaline phosphatase | PAL | – | – | – | – | – | – | – | – | – | – | – | – | – | – | – | – | – | – | – | – |
| Arginine arylamidase | ArgA | – | – | – | – | – | – | – | + | + | + | + | + | + | + | – | – | – | – | – | – |
| Proline arylamidase | ProA | – | – | – | – | – | – | – | – | – | – | – | – | – | – | – | – | – | – | – | – |
| Leucyl glycine arylamidse | LGA | – | – | – | – | – | – | – | + | + | + | + | + | + | + | – | – | – | – | – | – |
| Phenylalanine arylamidase | PheA | – | – | – | – | – | – | – | – | – | – | – | – | – | – | – | – | – | – | – | – |
| Leucine arylamidase | LeuA | – | – | – | – | – | – | – | + | + | + | + | + | + | + | + | + | + | w | w | w |
| Pyroglutamic acid arylamidase | PyrA | – | – | – | – | – | – | – | + | + | + | + | + | + | + | – | – | – | – | – | – |
| Tyrosine arylamidase | TyrA | – | – | – | – | – | – | – | – | – | – | – | – | – | – | – | – | – | – | – | – |
| Alanine arylamidase | AlaA | – | – | – | – | – | – | – | – | – | – | – | – | – | – | – | – | – | – | – | – |
| Glycine arylamidase | GlyA | – | – | – | – | – | – | – | + | + | + | + | + | + | + | + | + | + | w | w | w |
| Histidine arylamidaseα | HisA | – | – | – | – | – | – | – | + | + | + | + | + | + | + | – | – | – | – | – | – |
| Glutamyl glutamic acid arylamidase | GGA | – | – | – | – | – | – | – | – | – | – | – | – | – | – | – | – | – | – | – | – |
| Serine arylamidase | SerA | – | – | – | – | – | – | – | – | – | – | – | – | – | – | – | – | – | – | – | – |

TABLE 6

Biochemical characterization of the 20 Allobaculum-like organisms (ALO) by the Rapid ANAII

| RAPIS ANAII assay | Strain Group | A3 | Q5 | R1 | F16 ALO1 | E8 | P1 | U3 | A4 | F15 | L1 | L3 | M1 ALO2 | P2 | S4 | K8 | M7 | P3 ALO3 | Q1 | R5 | S3 |
|---|---|---|---|---|---|---|---|---|---|---|---|---|---|---|---|---|---|---|---|---|---|
| Urease | URE | – | – | – | – | – | – | – | – | – | – | – | – | – | – | – | – | – | – | – | – |
| p-nitrophenyl-β-diassacharride | BLTS | – | – | – | – | – | – | – | – | – | – | – | – | – | – | – | – | – | – | – | – |
| α-arabinosidase | αARA | – | – | – | – | – | – | – | – | – | – | – | – | – | – | – | – | – | – | – | – |
| ortho-Nitrophenyl-β-galactoside | ONPG | – | – | – | – | – | – | – | – | – | – | – | – | – | – | – | – | – | – | – | – |
| α-glucosidase | αGLU | – | – | – | – | – | – | – | + | + | + | + | + | + | + | – | – | – | – | – | – |
| β-glucosidase | βGLU | w | + | + | w | w | + | + | + | + | + | + | + | + | + | w | w | w | w | w | w |
| α-Galactosidase | αGAL | + | + | + | + | + | + | + | + | + | + | + | + | + | + | w | w | w | w | w | w |
| α-Fucosidase | αFUC | – | – | – | – | – | – | – | – | – | – | – | – | – | – | – | – | – | – | – | – |
| β-N-Acetyl-α-glucosaminidase | NAG | + | + | + | – | w | + | + | + | + | + | + | + | + | + | + | w | – | – | – | – |
| Alkaline phosphatase | PO4 | – | – | – | – | – | – | – | – | – | – | – | – | – | – | – | – | – | – | – | – |
| Leucylglycine aminopeptidase | LGY | – | – | – | – | – | – | – | + | + | + | + | + | + | + | + | + | + | + | + | + |
| Glycine arylamidase | GlyA | – | – | – | – | – | – | – | + | + | + | + | + | + | + | + | + | + | + | + | + |
| Proline arylamidase | ProA | – | – | – | – | – | – | – | – | – | – | – | – | – | – | – | – | – | – | – | – |
| Phenylalanine arylamidase | PheA | – | – | – | – | – | – | – | + | + | + | + | + | + | + | – | – | – | – | – | – |
| Arginine arylamidase | ArgA | – | – | – | – | – | – | – | + | + | + | + | + | + | + | + | + | + | + | + | + |
| Serine arylamidase | SerA | – | – | – | – | – | – | – | + | + | + | + | + | + | + | + | + | + | + | + | + |
| Pyroglutamic acid arylamidase | PYR | – | – | – | – | – | – | – | + | + | + | + | – | + | + | – | – | – | – | – | – |
| Indole | IND | – | – | – | – | – | – | – | – | – | – | – | – | – | – | – | – | – | – | – | – |

Example 8. Effect of Intestinal Colonization with *Ileibacterium* and/or *Dubosiella* on Diet-Induced Obesity (DIO)

Figure 12:
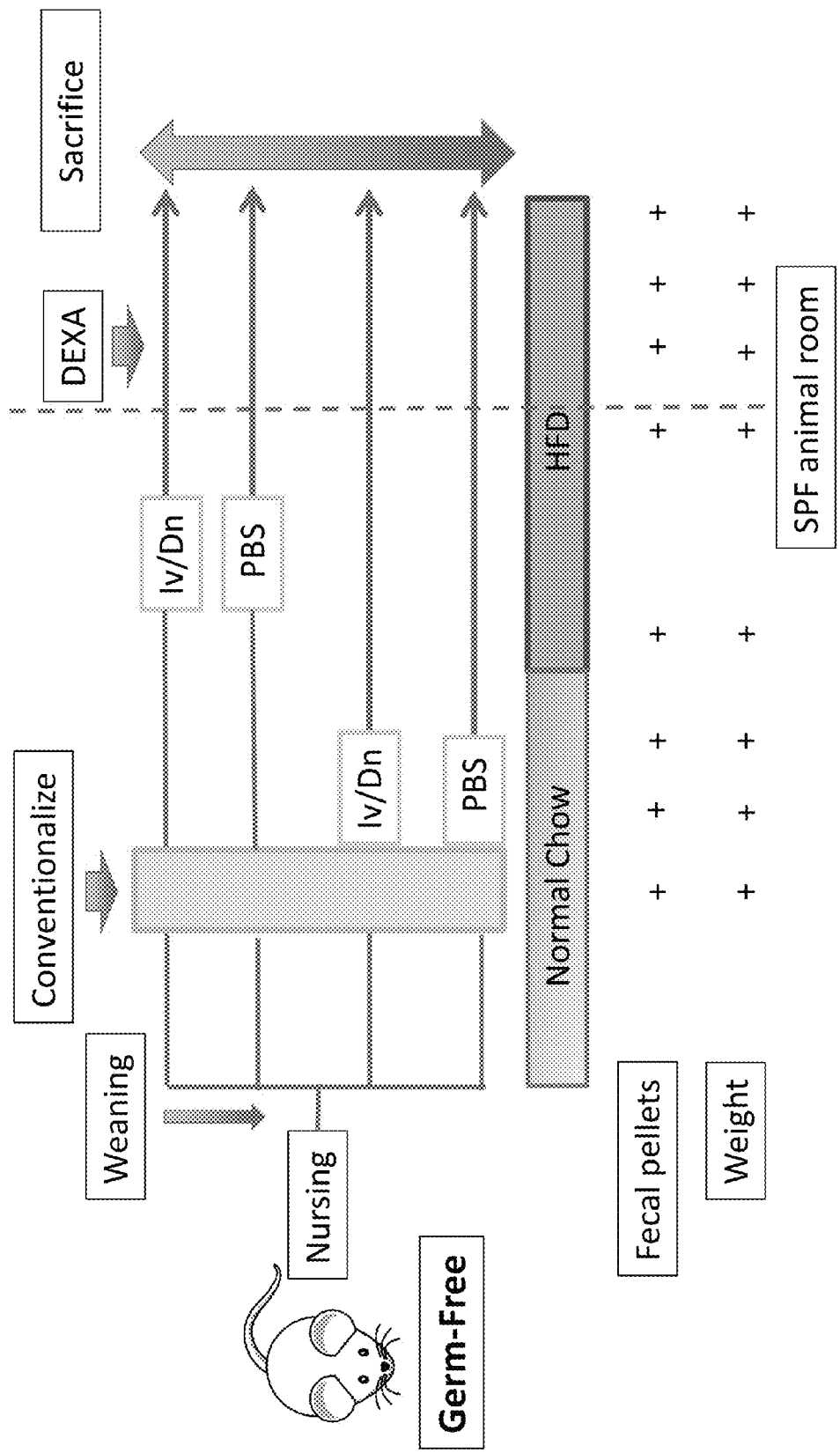
FIG. 12. Study design for testing the effect of intestinal colonization with bacteria of the genus *Ileibacterium* and/or *Dubosiella* on diet-induced obesity (DIO). Four groups of germ-free C57BL/6 mice are conventionalized with a Humanization Pool (HP) of fecal material from five healthy human adults. Within 3 days of the humanization, one group of mice each receives a pure culture of a representative of the genus *Ileibacterium* or *Dubosiella*, or both together. A second group is treated identically, but receives the vehicle only (i.e., without added organisms) by oral gavage as a control. The mice are fed as indicated, and fecal pellets are obtained to assess changes in the composition of their intestinal microbiome, and metabolic measurements obtained from blood, tissues, and by whole body analysis (e.g. DEXA scanning).

In order to assess whether introduction of *Ileibacterium* species and/or *Dubosiella* species can mitigate the effects of diet-induced obesity (DIO), germ-free mice are treated as indicated in FIG. 12. In particular, what is studied is whether the introduction of *Ileibacterium* species and/or *Dubosiella* species into the mouse model of DIO can mitigate the effects on the development of adiposity and abnormal gene expression in the intestinal wall. The effect of the timing of the exposure, i.e., before the initiation of a high-fat high calorie diet (e.g., HFD with 45% fat), or after the HFD has already begun, can also be assessed. Each of these can answer, for example: (i), does the presence of the introduced organism before the altered metabolism induced by DIO mitigate the effect; and (ii) after the DIO effects have begun, will the introduction of the organism still be effective in mitigating the abnormalities.

The study is conducted with Germ-free C57BL/6 mice (from the NYU Alexandria Germ Free Facility) that have been recently weaned and that are receiving sterilized normal chow (FIG. 12). 5-6 mice in each of four experimental groups can be used. A suspension of pooled fecal material from five healthy human adults in equal proportions by weight can be prepared. This suspension, diluted in pre-reduced phosphate buffered saline (PR-PBS), serves as the Humanization Pool (HP) that is given by oral gavage (100 microliters of suspension/mouse) to conventionalize (humanize) each mouse. The conventionalized mice are no longer germ-free but have a uniform humanized microbiota, and are kept in isolator cages so there will be no admixture with bacteria that are circulating in the conventional mouse facilities.

Within 3 days of humanization, one group of mice receives a pure culture of a representative of organisms in the genus *Ileibacterium* or *Dubosiella*, or both together (e.g., *Ileibacterium valens* and/or *Dubosiella newyorkensis*), which are grown as live cultures. Each of the mice will receive at least $10^8$ bacterial colony-forming units (cfu) each day for three days, by oral gavage, diluted in pre-reduced phosphate buffered saline (PR-PBS). A second group is treated identically, but receives PR-PBS only (without added organisms) by oral gavage as a control.

Within 48 hours, the diet of all mice in the study are changed from normal chow to HFD for the remainder of the study. Within 72 hours, mice in the two remaining groups receive either the same bacterial inoculum in PR-PBS, or PR-PBS alone, as before.

For all four groups of mice, fecal pellets are obtained to assess the changes in the composition of their intestinal microbiome. Metabolic parameters are assessed by examining the weight of the mice, measurement of metabolic markers in blood, including cholesterol, free fatty acids, and triglycerides, and hormones such as insulin and leptin, and by DEXA scanning. At sacrifice, cell populations and gene expression in the intestine are examined, as well as the composition of hepatic and adipose tissues, focusing on metabolic markers, and specific cellular populations and gene expression. At a systemic level, body weight and adiposity (by DEXA), and fat distribution are also examined.

In an alternative experimental variation, the mice are moved to a conventional specific-pathogen free (SPF) mouse room, and serial pre-mortem DEXA tests and other measurements are made.

The introduced organism can affect microbiome characteristics (such as alpha- and beta-diversity, as well as the representation of specific taxa) and host metabolic markers, as described above.

REFERENCES

1 Ogden, C. L., Carroll, M. D., Kit, B. K. & Flegal, K. M. Prevalence of Childhood and Adult Obesity in the United States, 2011-2012. *JAMA* 311, 806, doi:10.1001/jama.2014.732 (2014).
2 Turnbaugh, P. J. et al. An obesity-associated gut microbiome with increased capacity for energy harvest. *Nature* 444, 1027-1131, doi:10.1038/nature05414 (2006).
3 Cox, L. M. & Blaser, M. J. Pathways in microbe-induced obesity. *Cell Metab* 17, 883-894 (2013).
4 Coates, M. E., Fuller, R., Harrison, G. F., Lev, M. & Suffolk, S. F. A comparison of the growth of chicks in the Gustafsson germ-free apparatus and in a conventional environment, with and without dietary supplements of penicillin. *Br J Nutr* 17, 141-150 (1963).
5 Ley, R. E. et al. Evolution of Mammals and Their Gut Microbes. *Science* 320, 1647-1651 (2008).
6 Pantoja-Feliciano, I. G. et al. Biphasic assembly of the murine intestinal microbiota during early development. *ISME J7*, 1112-1115, doi:10.1038/ismej.2013.15 (2013).
7 Azad, M. B., Bridgman, S. L., Becker, A. B. & Kozyrskyj, A. L. Infant antibiotic exposure and the development of childhood overweight and central adiposity. *Int J Obes*, 1-9, doi:10.1038/ijo.2014.119 (2014).
8 Bailey, L. C. et al. Association of Antibiotics in Infancy With Early Childhood Obesity. *JAMA Pediatrics, doi:* 10.1001/jamapediatrics.2014.1539 (2014).
9 Ajslev, T. A., Andersen, C. S., Gamborg, M., Sorensen, T. I. A. & Jess, T. Childhood overweight after establishment of the gut microbiota: the role of delivery mode, pre-pregnancy weight and early administration of antibiotics. *Int J Obes* 35, 522-529, doi:10.1038/ijo.2011.27 (2011).
10 Blustein, J. et al. Association of caesarean delivery with child adiposity from age 6 weeks to 15 years. *Int J Obes* 37, 900-906, doi:10.1038/ijo.2013.49 (2013).
11 Trasande, L. et al. Infant antibiotic exposures and early-life body mass. *Int J Obes* 37, 16-23, doi:10.1038/ijo.2012.132 (2013).
12 Cox, L. M. & Blaser, M. J. Antibiotics in early life and obesity. *Nat Rev Endocrinol*, In Press (2014).
13 Hicks, L. A., Taylor, T. H. & Hunkler, R. J. U.S. Outpatient Antibiotic Prescribing, 2010. *New Engl J Med* 368, 1461-1462, doi:10.1056/NEJMc1212055 (2013).
14 Cho, I. et al. Antibiotics in early life alter the murine colonic microbiome and adiposity. *Nature* 488, 621-626 (2012).
15 Cox, L. M. et al. Altering the intestinal microbiota during a critical developmental window has lasting metabolic consequences. *Cell* 158, 705-721, doi:10.1016/j.cell.2014.05.052 (2014).
16 Ley, R. E., Peterson, D. A. & Gordon, J. I. Ecological and evolutionary forces shaping microbial diversity in the human intestine. *Cell* 124, 837-848, doi:10.1016/j.cell.2006.02.017 (2006).
17 Littman, D. R. & Pamer, E. G. Role of the Commensal Microbiota in Normal and Pathogenic Host Immune Responses. *Cell Host and Microbe* 10, 311-323, doi: papers3://publication/doi/10.1016/j.chom.2011.10.004 (2011).

18 Cho, I. & Blaser, M. J. The human microbiome: at the interface of health and disease. *Nat Rev Genet* 13, 260-270 (2012).
19 Chang, D.-H. et al. in *Antonie van Leeuwenhoek* Vol. 108 1309-1318 (2015).
20 Verbarg, S. et al. Erysipelothrix *inopinata* sp. nov., isolated in the course of sterile filtration of vegetable peptone broth, and description of Erysipelotrichaceae fam. nov. *Int J Sys Evol Microbiol* 54, 221-225 (2004).
21 Stackebrandt, E. in *Bergey's Manual of Systematic Bacteriology* Vol. 3 (eds Paul Vos et al.) 1299-1317 (Springer Science & Business Media, 2009).
22 Verbarg, S., Göker, M., Scheuner, C., Schumann, P. & Stackebrandt, E. in *The Prokaryotes* 79-105 (Springer, 2014).
23 Kanno, M. et al. *Catenisphaera adipataccumulans* gen. nov., sp. nov., a member of the family Erysipelotrichaceae isolated from an anaerobic digester. *Int J Sys Evol Microbiol* 65, 805-810 (2015).
24 De Maesschalck, C. et al. *Faecalicoccus acidiformans* gen. nov., sp. nov., isolated from the chicken caecum, and reclassification of *Streptococcus pleomorphus* (Barnes et al. 1977), *Eubacterium biforme* (Eggerth 1935) and *Eubacterium cylindroides* (Cato et al. 1974) as *Faecalicoccus pleomorphus* comb. nov., *Holdemanella biformis* gen. nov., comb. nov. and *Faecalitalea cylindroides* gen. nov., comb. nov., respectively, within the family Erysipelotrichaceae. *Int J Sys Evol Microbiol* 64, 3877-3884, doi:doi:10.1099/ijs.0.064626-0 (2014).
25 Gao, Z., Tseng, C.-h., Pei, Z. & Blaser, M. J. Molecular analysis of human forearm superficial skin bacterial biota. *Proc Natl Acad Sc* 104, 2927-2932, doi:10.1073/pnas.0607077104 (2007).
26 Schmieder, R. & Edwards, R. Quality control and preprocessing of metagenomic datasets. *Bioinformatics* 27, 863-864 (2011).
27 Caporaso, J. et al. QIIME allows analysis of high-throughput community sequencing data. *Nat Methods* 7, 335-336 (2010).
28 Altschul, S. F., Gish, W., Miller, W., Myers, E. W. & Lipman, D. J. Basic local alignment search tool. *J Molec Biol* 215, 403-410 (1990).
29 Yarza, P. et al. Uniting the classification of cultured and uncultured bacteria and archaea using 16S rRNA gene sequences. *Nat Rev Micro* 12, 635-645 (2014).
30 Thompson, J. D., Higgins, D. G. & Gibson, T. J. CLUSTAL W: improving the sensitivity of progressive multiple sequence alignment through sequence weighting, position-specific gap penalties and weight matrix choice. *Nucleic Acids Research* 22, 4673-4680 (1994).
31 Tamura, K., Stecher, G., Peterson, D., Filipski, A. & Kumar, S. MEGA6: Molecular Evolutionary Genetics Analysis Version 6.0. *Molecular Biology and Evolution* 30, 2725-2729, doi:papers3://publication/doi/10.1093/molbev/mst197 (2013).
32 Saitou, N. & Nei, M. The neighbor-joining method: a new method for reconstructing phylogenetic trees. *Molecular Biology and Evolution* 4, 406-425 (1987).
33 Jukes, T. H. & Cantor, C. R. Evolution of protein molecules. *Mammalian protein metabolism* 3, 132 (1969).
34 Felsenstein, J. Confidence limits on phylogenies: an approach using the bootstrap. *Evolution,* 783-791 (1985).
35 Bankevich, A. et al. SPAdes: A New Genome Assembly Algorithm and Its Applications to Single-Cell Sequencing. *J Comp Biol* 19, 455-477, doi:papers3://publication/doi/10.1089/cmb 0.2012.0021 (2012).
36 Gurevich, A., Saveliev, V., Vyahhi, N. & Tesler, G. QUAST: quality assessment tool for genome assemblies. *Bioinformatics* 29, 1072-1075, doi:10.1093/bioinformatics/btt086 (2013).
37 Tindall, B. J., Sikorski, J., Smibert, R. A. & Krieg, N. R. Phenotypic characterization and the principles of comparative systematics. (2007).
38 Kämpfer, P. & Kroppenstedt, R. M. Numerical analysis of fatty acid patterns of coryneform bacteria and related taxa. *Can. J. Microbiol.* 42, 989-1005 (1996).
39 Sasser, M. Identification of bacteria by gas chromatography of cellular fatty acids. (1990).
40 Cani, P. D. & Delzenne, N. M. The role of the gut microbiota in energy metabolism and metabolic disease. *Curr Pharm Des* 15, 1546-1558 (2009).
41 Everard, A. et al. Crosstalk between Akkermansia muciniphila and intestinal epithelium controls diet-induced obesity. *Proc Natl Acad Sci USA* 110, 9066-9071 (2013).
42 Vijay-Kumar, M. et al. Metabolic syndrome and altered gut microbiota in mice lacking Toll-like receptor 5. *Science* 328, 228-231, doi:10.1126/science.1179721 (2010).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A probiotic composition comprising (i) bacteria from one or more strains of the species *Ileibacterium* valens (*I. valens*) or a closely related operational taxonomic unit (OTU) which has at least 95% sequence identity to SEQ ID NO: 1 (NCBI GenBank Accession No. KU744404.1) over its entire length and (ii) a carrier and/or excipient and/or one or more prebiotic agents which stimulate growth and/or activity and/or preserve viability of one or more bacteria present in the composition.

2. The probiotic composition of claim 1, wherein the bacteria are from the strain NYU-BL-A3 *Ileibacterium valens*, which has been deposited on Aug. 11, 2016 with Leibniz Institute DSMZ-German Collection of Microorganisms and Cell Cultures, Inhoffenstr. 7 B, 38124 Braunschweig, Germany under Accession No. DSM 33318.

3. A probiotic composition comprising (i) bacteria from one or more strains of the species *Dubosiella newyorkensis* (*D. newy*) or a closely related operational taxonomic unit (OTU) which has at least 95% sequence identity to SEQ ID NO: 2 (NCBI GenBank Accession No. KU744405.1) over its entire length and (ii) a carrier and/or excipient and/or one or more prebiotic agents which stimulate growth and/or activity and/or preserve viability of one or more bacteria present in the composition.

4. The probiotic composition of claim 3, wherein the bacteria are from the strain NYU-BL-A4 *Dubosiella newyorkensis*, which has been deposited on Jun. 20, 2016 with Leibniz Institute DSMZ-German Collection of Microorganisms and Cell Cultures, Inhoffenstr. 7 B, 38124 Braunschweig, Germany under Accession No. DSM 33317.

5. The probiotic composition of claim 3, further comprising (iii) bacteria from one or more strains of the species *Ileibacterium* valens (*I. valens*) or a closely related OTU which has at least 95% sequence identity to SEQ ID NO: 1 (NCBI GenBank Accession No. KU744404.1) over its entire length.

6. The probiotic composition of claim 5, further comprising (iii) bacteria from the strain NYU-BL-A3 *Ileibacterium valens*, which has been deposited on Aug. 11, 2016 with Leibniz Institute DSMZ-German Collection of Microorganisms and Cell Cultures, Inhoffenstr. 7 B, 38124 Braunschweig, Germany under Accession No. DSM 33318.

* * * * *

SEQUENCE LISTING

```
<160> NUMBER OF SEQ ID NOS: 2

<210> SEQ ID NO 1
<211> LENGTH: 1459
<212> TYPE: DNA
<213> ORGANISM: Unknown
<220> FEATURE:
<223> OTHER INFORMATION: Erysipelotrichaceae bacterium NYU-BL-A3 16S
      ribosomal RNA gene

<400> SEQUENCE: 1
gtcaggatga acgctgtcgg catgcctaat acatgcaagt cgaacggtat ctttggatac      60
agtggcgaac gggtgagtaa cacgtaggga acctggccat acctggggga taatttctgg     120
```

```
aaacggaaac taataccgca tgggttttgc ttaagccttt aagcgaaatg aaagaagcgc    180
gagacgcttc ggggatggat ggtcctgcgc tgcattagct ggctggtgag gcaacggctc    240
accagggcga tgatgcatag ccggcctgag agggcggacg gccacactgg gactgagaca    300
cggcccagac tcctgcggga ggcagcagta gggaattttc gtcaatgggg gcaaccctga    360
acgagcaatg ccgcgtgagc gaagaaggtc ttcggattgt aaagctctgt tgccggggaa    420
aaaggaagga aagaggaaat gcttttcttt ggatggtacc cggccagaaa gtcacggcta    480
actacgtgcc agcagccgcg gtaatacgta ggtggcaagc gttatccgga atgattgggc    540
gtaaagggtg agcaggcggt tcttcaagtc atgagtgaaa ggcagaagct taacttctgt    600
tggctgatga gactggagaa cttgagtaca ggagagggcg gcggaactcc atgtgtagcg    660
gtaaaatgcg tagagatatg gaagaacacc agtggcgaag gcggccgcct ggactgaaac    720
tgacgctcag gcacgaaagc gtggggagca aataggatta gataccctag tagtccacgc    780
cgtaaacgat gaggagcagg tgtcgcaatg aaatgcggtg ccgaagccaa cgcaatgact    840
cctccgcctg gggagtatgc acgcaagtgt gaaactcaaa ggaattgacg ggggcccgca    900
caagcggtgg agtatgtggt ttaattcgaa gcaacgcgaa gaaccttacc aggccttgac    960
atgggaagcg aaggcttaga gataagctgg aggttatctt ccacacaggt ggtgcatggt   1020
tgtcgtcagc tcgtgtcgtg agatgttcag ttaagtctgg caacgagcgc aaccccttatg   1080 atatgttgct aacattgagt tgaggactca tatcagactg ccggtgacaa accggaggaa   1140
ggcggggatg acgtcaaatc atcatgcccc ttatggcctg ggctacacac gtactacaat   1200
ggcgtctaca gcgcgaagca aaccagtgat ggcaagcgaa ccgtcaaaag gcgtcttagt   1260
tcggattgaa gcctgcaacc cggcttcatg aaggcggaat cgctagtaat cgcggatcag   1320
catgccgcgg tgaatacgtt cccgggcctt gtacacaccg cccgtcaaac catggaagcc   1380
ggcaacgccc gaagccggcg gcataacccg caagggagtg agccgtcgaa ggcggggccg   1440
acgactgggg ttaagtcgt                                                1459
```

<210> SEQ ID NO 2
<211> LENGTH: 1460
<212> TYPE: DNA
<213> ORGANISM: Unknown
<220> FEATURE:
<223> OTHER INFORMATION: rysipelotrichaceae bacterium NYU-BL-A4 16S
    ribosomal RNA

<400> SEQUENCE: 2

```
caggatgaac gctggcggca tgcctaatac atgcaagtcg aacggatatc ttcggatatg     60
agtggcgaac gggtgagtaa cacgtaggga acctgcctgc atgagcggga gaacttctgg    120
aaacggaagc tgataccgga tgagcaaaga ggaggcatct tcttttggaa aaggggaca    180 agagtcccgc atgcagatgg acctgcggtg cattagctgg ttggagaggt aacggctcac    240
caaggcgacg atgcatagcc ggcctgagag gcggacggc cacactggga ctgagacacg    300
gcccagactc ctgcgggagg cagcagtagg gaattttcgt caatgggggg aaccctgaac    360
gagcaatgcc gcgtgagcga ggaaggtctt cggatcgtaa agctctgttg ccggggacaa    420
aaggcagaaa gagtggaaag cttttctgagt gatggtaccc ggcgaggaag tcacggctaa    480
ctacgtgcca gcagccgcgg taatacgtag gtggcgagcg ttatccggaa tgattgggcg    540
taaagggtgc gcaggcggcc gggcaagtcc gcagtaaaaa ctggaggctc aaccttcagg    600
ggctgcggaa actgtccggc tggagagcag gagaggacgg tggaactcca tgtgtagcgg    660
```

-continued

```
taaaatgcgt agatatatgg aagaacaccg gtggcgaagg cggccgtctg gcctgcatct    720
gacgctgagg cacgaaagcg tggggagcaa ataggattag ataccctagt agtccacgct    780
gtaaacgatg aggaccaagt gttggaggta aaacttcagt gctgcagtca acgcagtgag    840
tcctccgcct ggggagtatg cacgcaagtg tgaaactcaa aggaattgac gggggcccgc    900
acaagcggtg gagtatgtgg tttaattcga agcaacgcga agaaccttac caggccttga    960
cataggatgc gaagggatag agatatgccg gagggtatca tccatacagg tggtgcatgg   1020
ttgtcgtcag ctcgtgtcgt gagatgttca gttaagtctg gcaacgagcg caaccctcgt   1080
gatatgttac cagcagaaga tggggactca tatcagactg ccggtgagaa accggaggaa   1140
ggcggggatg acgtcaaatc atcatgcccc ttatggcctg ggctacacac gtactacaat   1200
ggcggccaca gagggcagcg actctgcaag gaggagcgaa tcccaaaaaa gccgtcccag   1260
ttcggatcgg agtctgcaac ccgactccgt gaagatggaa tcgctagtaa tcgcggatca   1320
gcatgccgcg gtgaatacgt tctcgggcct tgtacacacc gcccgtcaaa ccatgggagt   1380
gggcaatgcc cgaagccggt ggcgcaaccc gaaagggagc gagccgtcga aggcagggcc   1440
gatgactggg gttagtcgta                                                1460
```